US012651446B2

(12) United States Patent
Kobayashi et al.

(10) Patent No.: US 12,651,446 B2
(45) Date of Patent: Jun. 9, 2026

(54) INFORMATION PROCESSING DEVICE, INFORMATION PROCESSING METHOD, AND RECORDING MEDIUM

(71) Applicant: Anaut Inc., Tokyo (JP)

(72) Inventors: Nao Kobayashi, Tokyo (JP); Yuta Kumazu, Tokyo (JP); Seigo Senya, Tokyo (JP)

(73) Assignee: Anaut Inc., Tokyo (JP)

( * ) Notice: Subject to any disclaimer, the term of this patent is extended or adjusted under 35 U.S.C. 154(b) by 393 days.

(21) Appl. No.: 18/562,553

(22) PCT Filed: May 24, 2022

(86) PCT No.: PCT/JP2022/021185
§ 371 (c)(1),
(2) Date: Nov. 20, 2023

(87) PCT Pub. No.: WO2022/250031
PCT Pub. Date: Dec. 1, 2022

(65) Prior Publication Data
US 2024/0257509 A1      Aug. 1, 2024

(30) Foreign Application Priority Data

May 24, 2021      (JP) ................................. 2021-087141

(51) Int. Cl.
*G06V 10/00*          (2022.01)
*G06T 7/00*          (2017.01)
(Continued)

(52) U.S. Cl.
CPC .......... *G06V 10/809* (2022.01); *G06T 7/0012* (2013.01); *G06V 10/776* (2022.01);
(Continued)

(58) Field of Classification Search
CPC .... G06V 10/809; G06V 10/776; G06V 10/82; G06V 10/87; G06V 10/98;
(Continued)

(56) References Cited

U.S. PATENT DOCUMENTS

| 2006/0115146 A1 | 6/2006 | Ogura et al. |
| 2018/0271603 A1 | 9/2018 | Nir et al. |

(Continued)

FOREIGN PATENT DOCUMENTS

| JP | 2006-153742 A | 6/2006 |
| JP | 2020-89710 A | 6/2020 |

(Continued)

OTHER PUBLICATIONS

English translation of International Search Report for PCT Application No. PCT/JP2022/021185 mailed Aug. 16, 2022, 6 pages.

(Continued)

*Primary Examiner* — Van D Huynh
(74) *Attorney, Agent, or Firm* — Bret E. Field; Bozicevic, Field & Francis LLP

(57) ABSTRACT

An information processing device, includes one or more processors and a storage storing instructions causing any of the one or more processors to execute processing of executing computation by a first learning model in accordance with input of an operative field image, executing computation by a second learning model in accordance with the input of the operative field image, deriving an integrative recognition result for the operative field image based on a computation result based on the first learning model and the second learning model, and outputting information based on the derived recognition result.

25 Claims, 40 Drawing Sheets

(51) Int. Cl.

| | |
|---|---|
| *G06V 10/70* | (2022.01) |
| *G06V 10/776* | (2022.01) |
| *G06V 10/80* | (2022.01) |
| *G06V 10/82* | (2022.01) |
| *G06V 10/98* | (2022.01) |
| *G16H 50/20* | (2018.01) |

(52) U.S. Cl.
CPC .............. *G06V 10/82* (2022.01); *G06V 10/87* (2022.01); *G06V 10/98* (2022.01); *G16H 50/20* (2018.01); *G06T 2207/10068* (2013.01); *G06T 2207/20081* (2013.01); *G06T 2207/20084* (2013.01); *G06V 2201/031* (2022.01); *G06V 2201/034* (2022.01)

(58) Field of Classification Search
CPC ....... G06V 2201/031; G06V 2201/034; G06V 2201/03; G06T 7/0012; G06T 2207/10068; G06T 2207/20081; G06T 2207/20084; G06T 7/00; G16H 50/20; G16H 30/40; A61B 1/045
See application file for complete search history.

(56) References Cited

U.S. PATENT DOCUMENTS

| | | | | |
|---|---|---|---|---|
| 2020/0193236 | A1* | 6/2020 | Oosake ................ | G06V 10/454 |
| 2021/0015432 | A1* | 1/2021 | Konno ............... | A61B 5/02042 |
| 2021/0161363 | A1* | 6/2021 | Makino .................... | G06N 3/08 |
| 2021/0272284 | A1 | 9/2021 | Kamiyama | |
| 2022/0005190 | A1* | 1/2022 | N G ...................... | G06T 7/0012 |
| 2022/0082677 | A1 | 3/2022 | Kurashige et al. | |
| 2022/0198734 | A1* | 6/2022 | Kudo .................... | G06N 3/045 |
| 2022/0202284 | A1* | 6/2022 | Tachibana .......... | A61B 1/00006 |
| 2023/0230244 | A1* | 7/2023 | Kusu ................. | G06V 10/7796 382/128 |
| 2024/0156547 | A1* | 5/2024 | Luengo Muntion ... | A61B 34/25 |

FOREIGN PATENT DOCUMENTS

| | | |
|---|---|---|
| JP | 2020-156860 A | 10/2020 |
| JP | 2021-29979 A | 3/2021 |
| WO | WO2019/054045 A1 | 3/2019 |
| WO | WO2019/131742 A1 | 7/2019 |
| WO | WO2019/181432 A1 | 9/2019 |
| WO | WO2020/194662 A1 | 10/2020 |
| WO | WO2020/194942 A1 | 10/2020 |
| WO | WO2020194462 A1 | 10/2020 |
| WO | WO2020195807 A1 | 10/2020 |
| WO | WO2021/039298 A1 | 3/2021 |
| WO | WO2021053808 A1 | 3/2021 |
| WO | WO2021075418 A1 | 4/2021 |

OTHER PUBLICATIONS

Notice of Reasons for Refusal for Japanese Application No. 2023-173728 mailed Jan. 9, 2024, with its machine translation, 9 pages.
Office Action for Japanese Application No. 2024-025949 mailed Apr. 16, 2024, with its machine translation, 6 pages.

* cited by examiner

FIG. 10

Input image

Computation result
(Event)

| Scene | Preliminary information |
|---|---|
| Lymph node dissection of the upper border of pancreas in stomach cancer surgery. | Pancreas exist under lymph node. |
| ⋮ | ⋮ |

FIG. 23

| Scene | Name (blood vessel) | Name (nerve) |
|---|---|---|
| Sigmoid colon cancer surgery | Inferior mesenteric artery | inferior mesenteric nerve plexus |
| ⋮ | ⋮ | ⋮ |

FIG. 25

| Scene | Organ | Anatomic information |
|---|---|---|
| Surgery of stomach | Portal | The left gastric vein branches from the portal. |
| Surgery of stomach | Right gastric vein | The root of the right gastric vein is an inverted Y shape. |
| ⋮ | ⋮ | ⋮ |

FIG. 27

| Scene | Organ | Case |
|---|---|---|
| Sigmoid colon cancer surgery | Inferior mesenteric artery | Bleeding (2021.03.15 16:34) |
| Sigmoid colon cancer surgery | Inferior mesenteric artery | Bleeding (2021.03.19 10:26) |
| ⋮ | ⋮ | ⋮ |

FIG. 30

| Date and Time | Scene | Moving image file |
|---|---|---|
| 2021.4.10 13:50 | Start of surgery | —— |
| 2021.4.10 13:52 | Damage | MOV001.mpg |
| 2021.4.10 14:10 | Restoration | MOV002.mpg |
| ⋮ | ⋮ | ⋮ |
| 2021.4.10 14:28 | Damage | MOV00X.mpg |
| 2021.4.10 14:45 | Restoration | MOV00Y.mpg |
| 2021.4.10 15:10 | End of surgery | —— |

FIG. 35

| Confidence | Evaluation coefficient |
|:---:|:---:|
| 0~0.1 | 4 |
| 0.1~0.2 | 2 |
| 0.2~0.3 | 0 |
| 0.3~0.4 | -2 |
| 0.4~0.5 | -4 |
| 0.5~0.6 | -4 |
| 0.6~0.7 | -2 |
| 0.7~0.8 | 0 |
| 0.8~0.9 | 2 |
| 0.9~1 | 4 |

FIG. 36A

| Confidence | Pixel number ratio | Evaluation coefficient | Score |
|---|---|---|---|
| 0~0.1 | 80 | 4 | 320 |
| 0.1~0.2 | 0 | 2 | 0 |
| 0.2~0.3 | 0 | 0 | 0 |
| 0.3~0.4 | 0 | -2 | 0 |
| 0.4~0.5 | 0 | -4 | 0 |
| 0.5~0.6 | 0 | -4 | 0 |
| 0.6~0.7 | 0 | -2 | 0 |
| 0.7~0.8 | 0 | 0 | 0 |
| 0.8~0.9 | 0 | 2 | 0 |
| 0.9~1 | 20 | 4 | 80 |
| Total | 100 | — | 400 |

FIG. 36B

| Confidence | Pixel number ratio | Evaluation coefficient | Score |
|---|---|---|---|
| 0~0.1 | 30 | 4 | 120 |
| 0.1~0.2 | 20 | 2 | 40 |
| 0.2~0.3 | 10 | 0 | 0 |
| 0.3~0.4 | 10 | -2 | -20 |
| 0.4~0.5 | 10 | -4 | -40 |
| 0.5~0.6 | 6 | -4 | -24 |
| 0.6~0.7 | 4 | -2 | -8 |
| 0.7~0.8 | 4 | 0 | 0 |
| 0.8~0.9 | 4 | 2 | 8 |
| 0.9~1 | 2 | 4 | 8 |
| Total | 100 | — | 84 |

FIG. 36C

| Confidence | Pixel number ratio | Evaluation coefficient | Score |
|---|---|---|---|
| 0~0.1 | 40 | 4 | 160 |
| 0.1~0.2 | 20 | 2 | 40 |
| 0.2~0.3 | 10 | 0 | 0 |
| 0.3~0.4 | 6 | -2 | -12 |
| 0.4~0.5 | 4 | -4 | -16 |
| 0.5~0.6 | 2 | -4 | -8 |
| 0.6~0.7 | 4 | -2 | -8 |
| 0.7~0.8 | 4 | 0 | 0 |
| 0.8~0.9 | 4 | 2 | 8 |
| 0.9~1 | 6 | 4 | 24 |
| Total | 100 | — | 188 |

FIG. 39

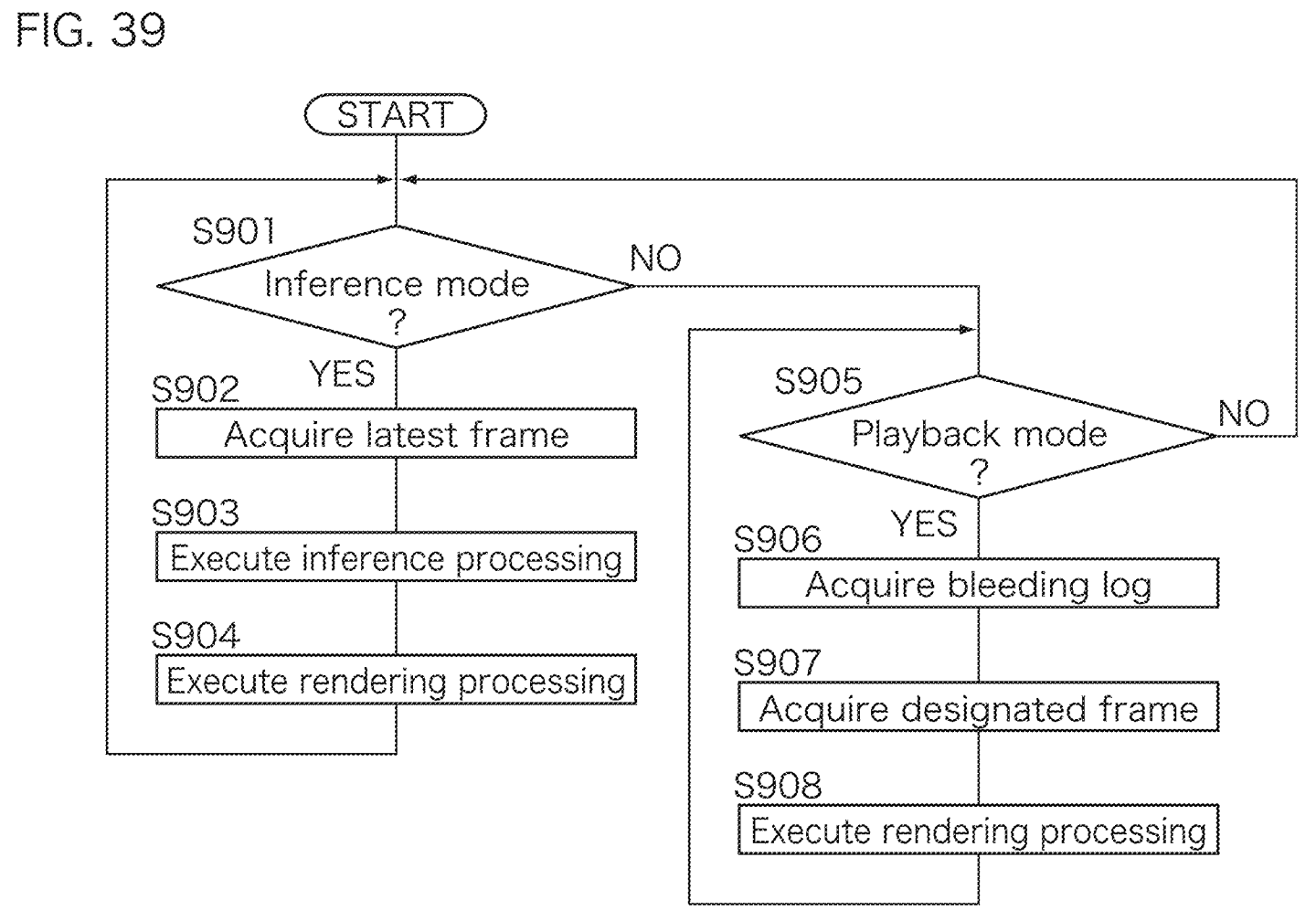

START

S901 Inference mode ? — NO → S905 Playback mode ? — NO →

YES (S901):

S902 Acquire latest frame

S903 Execute inference processing

S904 Execute rendering processing

YES (S905):

S906 Acquire bleeding log

S907 Acquire designated frame

S908 Execute rendering processing

INFORMATION PROCESSING DEVICE, INFORMATION PROCESSING METHOD, AND RECORDING MEDIUM

CROSS-REFERENCE TO RELATED APPLICATIONS

This application is the national phase under 35 U. S. C. § 371 of PCT International Application No. PCT/JP2022/021185 which has an International filing date of May 24, 2022 and designated the United States of America.

FIELD

The present application relates to an information processing device, an information processing method, and a recording medium.

BACKGROUND

In the medical field, since the pathology diagnosis requires specialized knowledge and experience, a part of the body tissue is excised, and diagnosis is performed outside the body with a microscope or the like.

On the other hand, recently, an invention has been proposed in which the pathology diagnosis is performed by directly observing the inside of the body with an endoscope or the like, and analyzing an observation image with a computer (for example, refer to Japanese Patent Laid-Open Publication No. 2006-153742).

In order to create a learning model for recognizing a lesion or the like from the observation image, the knowledge of a medical specialist is essential, but the specialty of a medical doctor is subdivided, and thus, single-class teaching data is often created.

In a learning model created with the single-class teaching data, only single-class inference can be performed.

SUMMARY

An object of the present application is to provide an information processing device, an information processing method, and a computer program deriving an integrative recognition result from computation results of a plurality of types of learning models.

An information processing device in one aspect of the present application, includes: a first computation unit executing computation by a first learning model, in accordance with input of an operative field image; a second computation unit executing computation by a second learning model, in accordance with the input of the operative field image; a derivation unit deriving an integrative recognition result for the operative field image based on a computation result output from the first computation unit and a computation result output from the second computation unit; and an output unit outputting information based on the derived recognition result.

An information processing method in one aspect of the present application, allows a computer to execute processing of: executing computation by a first learning model, in accordance with input of an operative field image; executing computation by a second learning model, in accordance with the input of the operative field image; deriving an integrative recognition result for the operative field image based on a computation result by the first learning model and a computation result by the second learning model; and outputting information based on the derived recognition result.

A recording medium in one aspect of the present application is a non-transitory computer readable recording medium storing a computer program, allows a computer to execute processing of: executing computation by a first learning model, in accordance with input of an operative field image; executing computation by a second learning model, in accordance with the input of the operative field image; deriving an integrative recognition result for the operative field image based on a computation result by the first learning model and a computation result by the second learning model; and outputting information based on the derived recognition result.

According to this application, it is possible to derive the integrative recognition result from the computation results of the plurality of types of learning models.

BRIEF DESCRIPTION OF THE DRAWINGS

FIG. 10 is a schematic view illustrating a configuration example of a third learning model.

FIG. 13 is a schematic view illustrating a configuration example of a fourth learning model.

FIG. 19 is a conceptual diagram illustrating an example of a preliminary information table.

FIG. 23 is a conceptual diagram illustrating an example of a proper name table.

FIG. 25 is a conceptual diagram illustrating an example of a structure table.

FIG. 27 is a conceptual diagram illustrating an example of a case table.

FIG. 30 is a conceptual diagram illustrating an example of a scene recording table.

FIG. 35 is a diagram illustrating an example of an evaluation coefficient table.

FIGS. 36A to 36C are a diagram illustrating an example of a score calculation result.

FIG. 39 is a flowchart illustrating a procedure of processing executed by a first computation unit.

DESCRIPTION OF EMBODIMENTS

Hereinafter, an aspect in which the present application is applied to an assistance system of a laparoscope surgery will be described in detail by using the drawings. Note that, the present application is not limited to the laparoscope surgery, and can be applied to the overall scopic surgery using an imaging device, such as a thoracoscope, a gastrointestinal endoscope, a cystoscope, an arthroscope, a robot-assisted endoscope, a surgical microscope, and an endoscope.

Embodiment 1

Figure 1:
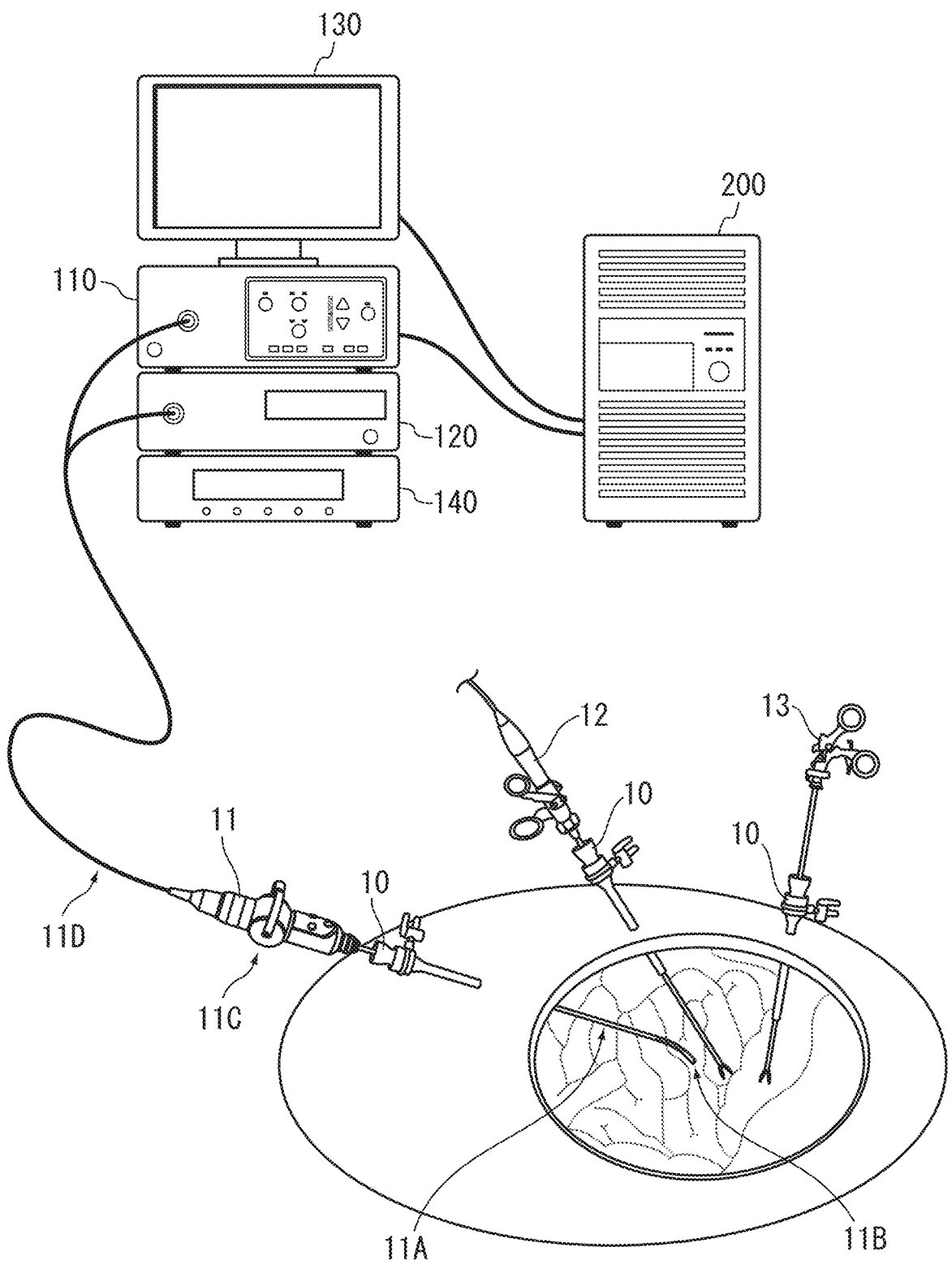
FIG. 1 is a schematic view illustrating a schematic configuration of a surgery assistance system according to Embodiment 1.

FIG. 1 is a schematic view illustrating a schematic configuration of a surgery assistance system according to Embodiment 1. In an laparoscope surgery, a plurality of opening instruments referred to as a trocar 10 are attached to the abdominal wall of a patient, and an instrument such as an laparoscope 11, an energy treatment tool 12, or forceps 13 is inserted into the body of the patient from the opening provided in the trocar 10, instead of performing a laparotomy. An operator performs a treatment such as excising an affected area by using the energy treatment tool 12 while observing an image (an operative field image) of the inside of the body of the patient, which is imaged by the laparoscope 11, in real-time. A surgical tool such as the laparoscope 11, the energy treatment tool 12, or the forceps 13 is retained by the operator, a robot, or the like. The operator is a healthcare worker involved in the laparoscopic surgery, and includes an operator, an assistant, a nurse, a medical doctor monitoring a surgery, and the like.

The laparoscope 11 includes an insertion portion 11A inserted into the body of the patient, an imaging device 11B built in the front edge portion of the insertion portion 11A, an operation portion 11C provided in the tail edge portion of the insertion portion 11A, and a universal cord 11D for the connection to a camera control unit (CCU) 110 or a light source device 120.

The insertion portion 11A of the laparoscope 11 includes a rigid tube. A bending portion is provided in the front edge portion of the rigid tube. A bending mechanism of the bending portion is a known mechanism incorporated in a general laparoscope, and is configured to bend, for example, in four directions of up, down, left, and right, by pulling a manipulation wire in conjunction with the operation via the operation portion 11C. Note that, the laparoscope 11 is not limited to a flexible scope including the bending portion as described above, and may be a rigid scope not including the bending portion, or may be an imaging device not including the bending portion or the rigid tube.

The imaging device 11B includes a solid state image sensor such as a CMOS (Complementary Metal Oxide Semiconductor), and a driver circuit including a timing generator (TG), an analog signal processing circuit (AFE), and the like. The driver circuit of the imaging device 11B imports signals of each color of RGB output from the solid state image sensor, in synchronization with a clock signal output from TG, performs required processing such as filter-out, amplification, and AD conversion, in AFE, and generates image data in a digital format. The driver circuit of the imaging device 11B transmits the generated image data to the CCU 110 through the universal cord 11D.

The operation portion 11C includes an angular lever, a remote switch, or the like, which is manipulated by the operator. The angular lever is a manipulation tool receiving a manipulation for bending the bending portion. Instead of the angular lever, a bending manipulation knob, a joystick, and the like may be provided. The remote switch, for example, includes a switch switching an observation image to moving image display or still image display, a zoom switch zooming in or out the observation image, and the like. A specific function set in advance may be allocated to the remote switch, or a function set by the operator may be allocated to the remote switch.

In addition, an oscillator including a linear resonant actuator, a piezoelectric actuator, or the like may be built in the operation portion 11C. In a case where an event to be reported to the operator manipulating the laparoscope 11 occurs, the CCU 110 may oscillate the operation portion 11C by operating the oscillator built in the operation portion 11C to notify the operator of the occurrence of the event.

In the insertion portion 11A, the operation portion 11C, and the universal cord 11D of the laparoscope 11, a transmission cable for transmitting a control signal output from the CCU 110 to the imaging device 11B, or the image data output from the imaging device 11B, a light guide guiding illumination light exiting from the light source device 120 to the front edge portion of the insertion portion 11A, and the like are arranged. The illumination light exiting from the light source device 120 is guided to the front edge portion of the insertion portion 11A through the light guide, and is applied to an operative field through an illumination lens provided in the front edge portion of the insertion portion 11A. Note that, in this embodiment, the light source device 120 is described as an independent device, but the light source device 120 may be built in the CCU 110.

The CCU 110 includes a control circuit controlling the operation of the imaging device 11B provided in the laparoscope 11, an image processing circuit processing the image data from the imaging device 11B, which is input through the universal cord 11D, and the like. The control circuit includes a CPU (Central Processing Unit), a ROM (Read Only Memory), a RAM (Random Access Memory), and the like, and outputs the control signal to the imaging device 11B and controls imaging start, imaging stop, zooming, or the like, in accordance with the manipulation of various switches provided in the CCU 110 or the manipulation of the operation portion 11C provided in the laparoscope 11. The image processing circuit includes a DSP (Digital Signal Processor), an image memory, and the like, and performs suitable processing such as color separation, color interpolation, gain correction, white balance adjustment, and gamma correction with respect to the image data input through the universal cord 11D. The CCU 110 generates a frame image for a moving image from the processed image data, and sequentially outputs each of the generated frame images to an information processing device 200 described below. The frame rate of the frame image, for example, is 30 FPS (Frames Per Second).

The CCU 110 may generate video data based on a predetermined standard such as an NTSC (National Television System Committee), a PAL (Phase Alternating Line), and DICOM (Digital Imaging and Communication in Medicine). By the CCU 110 outputting the generated video data to a display device 130, it is possible to display the operative field image (video) on a display screen of the display device 130 in real-time. The display device 130 is a monitor including a liquid crystal panel, an organic EL (Electro-Luminescence) panel, or the like. In addition, the CCU 110 may output the generated video data to a video recording device 140 such that the video data is recorded in the video recording device 140. The video recording device 140 includes a recording device such as an HDD (Hard Disk Drive) recording the video data output from the CCU 110, together with an identifier for identifying each surgery, a surgery date and time, a surgical site, a patient name, an operator name, and the like.

The information processing device 200 acquires the image data of the operative field image by the CCU 110, and inputs the acquired image data of the operative field image to each of a plurality of learning models to execute computation by each of the learning models. The information processing device 200 derives an integrative recognition result for the operative field image from computation results of the plurality of learning models, and outputs information based on the derived recognition result.

Figure 2:
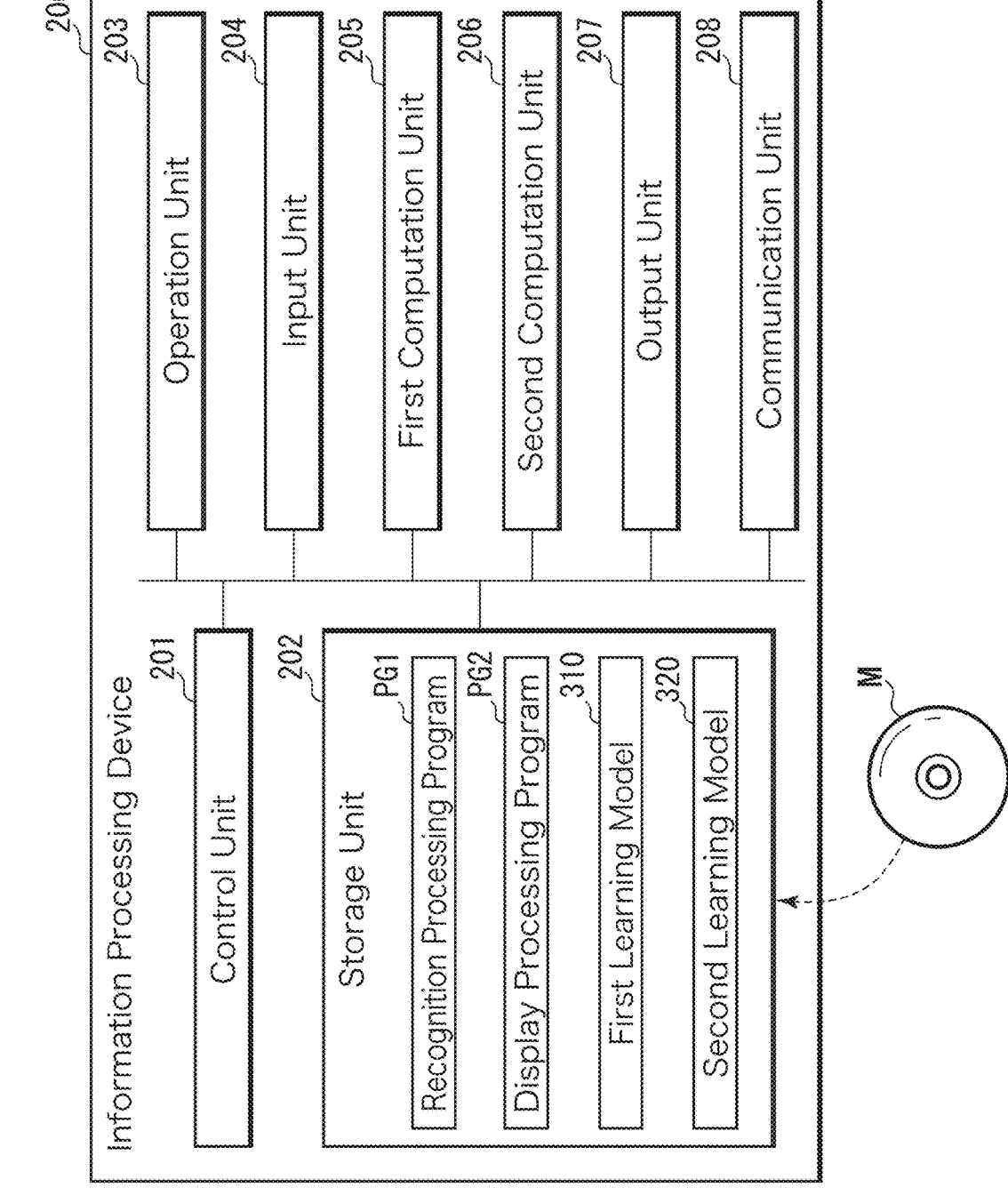
FIG. 2 is a block diagram illustrating an internal configuration of an information processing device.

FIG. 2 is a block diagram illustrating the internal configuration of the information processing device 200. The information processing device 200 is a dedicated or general-purpose computer including a control unit 201, a storage unit 202, an operation unit 203, an input unit 204, a first computation unit 205, a second computation unit 206, an output unit 207, a communication unit 208, and the like. The information processing device 200 may be a computer provided inside a surgery room, or may be a computer provided outside the surgery room. The information processing device 200 may be a server provided inside the hospital in which the laparoscopic surgery is performed, or may be a server provided outside the hospital. The information processing device 200 is not limited to a single computer, and may be a computer system including a plurality of computers or peripheral devices. The information processing device 200 may be a virtual machine that is virtually constructed by software.

The control unit 201, for example, includes a CPU, a ROM, a RAM, and the like. In the ROM provided in the control unit 201, a control program for controlling the operation of each hardware unit provided in the information processing device 200, and the like are stored. The CPU in the control unit 201 executes the control program stored in the ROM or various computer programs stored in the storage unit 202 described below, and controls the operation of each hardware unit to allow the entire device to function as the information processing device in this application. In the RAM provided in the control unit 201, data or the like used during the execution of the computation is transitorily stored.

In this embodiment, the control unit 201 includes the CPU, the ROM, and the RAM, but the configuration of the control unit 201 is any configuration, and may be a computation circuit or a control circuit including a GPU (Graphics Processing Unit), a DSP (Digital Signal Processor), an FPGA (Field Programmable Gate Array), a quantum processor, a volatile or non-volatile memory, and the like. In addition, the control unit 201 may have a function as a clock outputting date and time information, a timer measuring the elapsed time from when a measurement start instruction is applied to when a measurement end instruction is applied, a counter counting the number, or the like.

The storage unit 202 is a storage device such as a hard disk and a flash memory. In the storage unit 202, the computer program executed by the control unit 201, various data pieces acquired from the outside, various data pieces generated inside the device, and the like are stored.

The computer program stored in the storage unit 202 includes a recognition processing program PG1 for allowing the control unit 201 to execute processing for recognizing a recognition target included in the operative field image, a display processing program PG2 for allowing the control unit 201 to execute processing for displaying information based on a recognition result on the display device 130, and the like. Note that, the recognition processing program PG1 and the display processing program PG2 are not necessarily an independent computer program, and may be implemented as one computer program. Such programs, for example, are provided by a non-transitory recording medium M in which the computer program is readably recorded. The recording medium M is a portable memory such as a CD-ROM, a USB memory, and an SD (Secure Digital) card. The control unit 201 reads out a desired computer program form the recording medium M by using a reader that is not illustrated, and stores the read computer program in the storage unit 202. Alternatively, the computer program described above may be provided by communication. In this case, the control unit 201 may download a desired computer program through the communication unit 208, and may store the downloaded computer program in the storage unit 202.

The above computer program may be a single computer program or a group of programs composed of multiple computer programs. The above computer programs may partially use existing libraries. Each of the above computer programs may be executed on a single computer, or may be executed cooperatively by multiple computers.

The storage unit 202 includes a first learning model 310 and a second learning model 320. The first learning model 310 is a trained learning model that is trained to output information relevant to a first organ included in the operative field image, in accordance with the input of the operative field image. The first organ includes a peculiar organ such as the esophagus, the stomach, the large intestine, the pancreas, the spleen, the ureter, the lungs, the prostate, the uterus, the gallbladder, the liver, and the vas deferens, or a non-peculiar organ such as a connective tissue, fat, a nerve, a blood vessel, a muscle, and a membranous structure. The first organ is not limited to such specific organs, may be any structure in the body. Similarly, the second learning model 320 is a trained learning model that is trained to output information relevant to a second organ included in the operative field image, in accordance with the input of the operative field image. The second organ includes the peculiar organ or the non-peculiar organ described above. The second organ is not limited to such specific organs, and may be any structure in the body.

Note that, in the following description, in a case where it is not necessary to distinguish between the specific organ and the non-specific organ, the peculiar organ and the non-peculiar organ will also be simply referred to as an organ.

In Embodiment 1, the second organ that is the recognition target has features similar to those of the first organ, and an organ that may be falsely recognized as the first organ in recognition processing is selected. For example, in a case where a recognition target of the first learning model 310 is a loose connective tissue, a nerve tissue (or a membrane structure) is selected as a recognition target of the second learning model 320. A combination of the first organ and the second organ is not limited to (a) the loose connective tissue and the nerve tissue (or the membrane structure), and may be a combination such as (b) fat and the pancreas, (c) fat to be excised and fat to be preserved, (d) two of bleeding, a bleeding mark, and a blood vessel, (e) two of the ureter, the artery, and a membrane structure, (f) the stomach and the enteric canal, and (g) the liver and the spleen.

In Embodiment 1, a case will be described in which the first organ is a loose connective tissue, and the second organ is a nerve tissue. That is, the first learning model 310 is trained to output information relevant to the loose connective tissue included in the operative field image, in accordance with the input of the operative field image. Such a first learning model 310 is generated by training using the operative field image obtained by imaging the operative field, and ground truth data indicating a first organ portion (in Embodiment 1, a loose connective tissue portion) in the operative field image, as training data, and using a suitable learning algorithm. The ground truth data indicating the first organ portion is generated by the manual annotation of a specialist such as a medical doctor. The same applies to the second learning model 320.

The first and second learning models 310 and 320 may be generated inside the information processing device 200, or may be generated in an external server. In the latter case, the information processing device 200 may download the first and second learning models 310 and 320 generated in the external server by communication, and may store the downloaded first and second learning models 310 and 320 in the storage unit 202. In the storage unit 202, information of layers provided in the first and second learning models 310 and 320, information of nodes configuring each of the layers, and information of parameters or the like determined by training, such as a weight coefficient and a bias between the nodes, are stored as definition information of the first and second learning models 310 and 320.

The operation unit 203 includes a manipulation device such as a keyboard, a mouse, a touch panel, a non-contact panel, a stylus pen, and voice input using a microphone. The operation unit 203 receives the manipulation of the operator or the like, and outputs information relevant to the received manipulation to the control unit 201. The control unit 201 executes suitable processing, in accordance with the manipulation information input from the operation unit 203. Note that, in this embodiment, the information processing device 200 includes the operation unit 203, but the manipulation may be received through various devices such as the CCU 110 connected to the outside.

The input unit 204 includes a connection interface for connecting an input device. In this embodiment, the input device connected to the input unit 204 is the CCU 110. The image data of the operative field image that is imaged by the laparoscope 11 and processed by the CCU 110 is input to the input unit 204. The input unit 204 outputs the input image data to the control unit 201. In addition, the control unit 201 may store the image data acquired from the input unit 204 in the storage unit 202.

In the embodiment, a configuration is described in which the image data of the operative field image is acquired from the CCU 110 through the input unit 204, but the image data of the operative field image may be directly acquired from the laparoscope 11, or the image data of the operative field image may be acquired by an image processing device (not illustrated) detachably mounted on the laparoscope 11. In addition, the information processing device 200 may acquire the image data of the operative field image recorded in the video recording device 140.

The first computation unit 205 includes a processor, a memory, or the like. An example of the processor is a GPU (Graphics Processing Unit), and an example of the memory is a VRAM (Video RAM). In a case where the operative field image is input, the first computation unit 205 executes the computation of the first learning model 310 by the built-in processor, and outputs the computation result to the control unit 201. In addition, in accordance with the instruction from the control unit 201, the first computation unit 205 renders an image to be displayed on the display device 130 on the built-in memory, and outputs the image to the display device 130 through the output unit 207 to display a desired image on the display device 130.

As with the first computation unit 205, the second computation unit 206 includes a processor, a memory, or the like. The second computation unit 206 may be the same as the first computation unit 205, or may have computation capability lower than that of the first computation unit 205. In a case where the operative field image is input, the second computation unit 206 executes the computation of the second learning model 320 by the built-in processor, and outputs the computation result to the control unit 201. In addition, in accordance with the instruction from the control unit 201, the second computation unit 206 renders an image to be displayed on the display device 130 on the built-in memory, and outputs the image to the display device 130 through the output unit 207 to display a desired image on the display device 130.

The output unit 207 includes a connection interface for connecting an output device. In this embodiment, the output device connected to the output unit 207 is the display device 130. In a case where information to be reported to the operator or the like, such as the integrative recognition result derived from the computation results of the learning models 310 and 320, is generated, the control unit 201 outputs the generated information to the display device 130 by the output unit 207 to display the information on the display device 130. Alternatively, the output unit 207 may output the information to be reported to the operator or the like by a voice or a sound.

The communication unit 208 includes a communication interface for transmitting and receiving various data pieces. The communication interface provided in the communication unit 208 is a communication interface based on a wired or wireless communication standard that is used in Ethernet (Registered Trademark) or WiFi (Registered Trademark). In a case where data to be transmitted is input from the control unit 201, the communication unit 208 transmits the data to be transmitted to a designated destination. In addition, in a case where data transmitted from an external device is received, the communication unit 208 outputs the received data to the control unit 201.

Next, the operative field image input to the information processing device 200 will be described.

Figure 3:
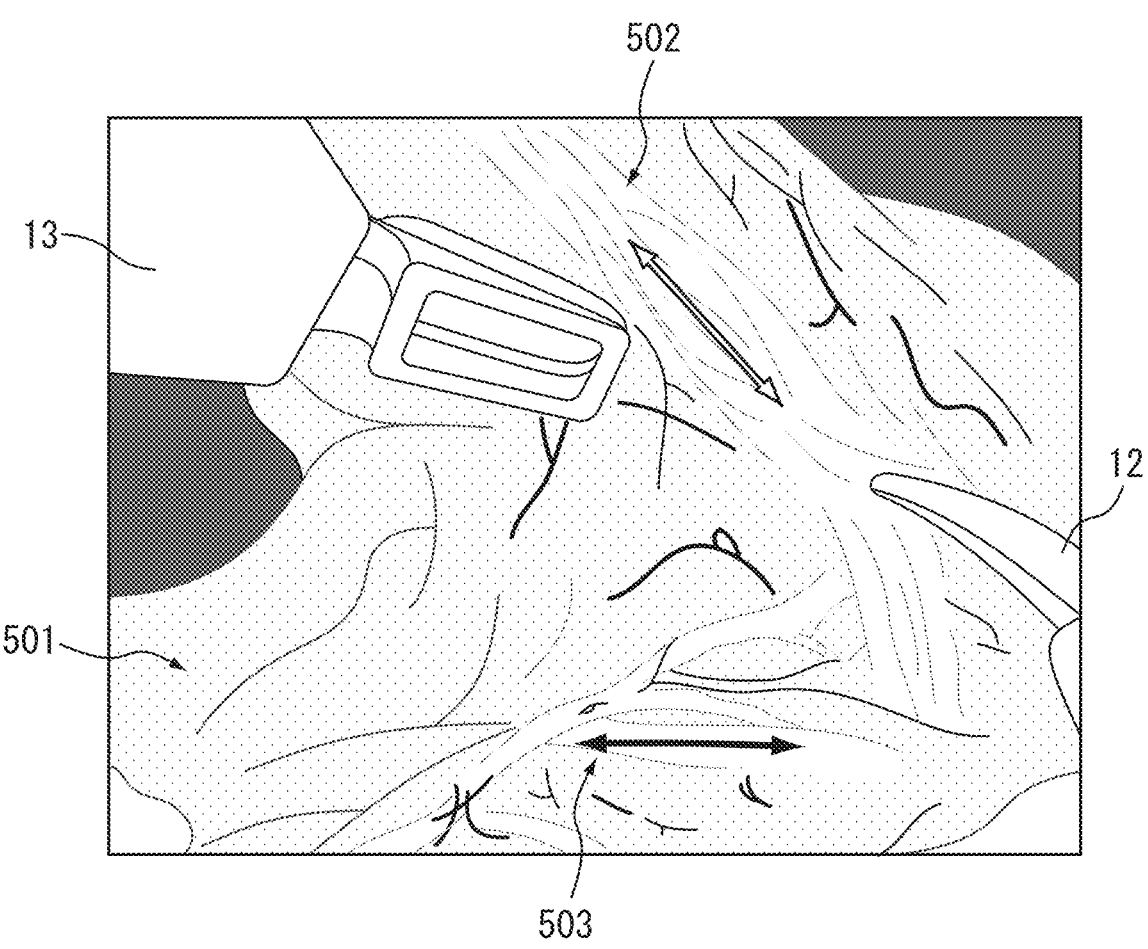
FIG. 3 is a schematic view illustrating an example of an operative field image.

FIG. 3 is a schematic view illustrating an example of the operative field image. The operative field image in this embodiment is an image obtained by imaging the inside of the abdominal cavity of the patient with the laparoscope 11. The operative field image is not necessarily a raw image output from the imaging device 11B of the laparoscope 11, and may be an image (a frame image) processed by the CCU 110 or the like.

The operative field imaged by the laparoscope 11 includes a tissue configuring the peculiar organ, the blood vessel, the nerve, or the like, a connective tissue existing between the tissues, a tissue including a lesion site such as a tumor, and a tissue of a membrane or a layer covering the tissue. The operator peels off the tissue including the lesion site by using the surgical tool such as the energy treatment tool 12 or the forceps 13 while grasping an anatomical structural relationship. The operative field image illustrated in FIG. 3 as an example represents a scene in which a suitable tension is applied to a loose connective tissue 502 by pulling a membrane covering an organ 501 using the forceps 13, and the loose connective tissue 502 is peeled off using the energy treatment tool 12. The loose connective tissue 502 is a fibrous connective tissue filling between tissues or organs, and has a comparatively small amount of fibers (elastic fibers) configuring the tissue. The loose connective tissue 502 is peeled off as necessary in the case of expanding the organ 501 or in the case of excising the lesion site. In the example of FIG. 3, it is illustrated that the loose connective tissue 502 runs in a vertical direction (in the direction of an open arrow in the drawing), and a nerve tissue 503 runs in a horizontal direction (in the direction of a black arrow in the drawing) to intersect with the loose connective tissue 502.

In general, both of the loose connective tissue and the nerve tissue appearing in the operative field image are a tissue that is white in color and runs linearly, and thus, it is often difficult to apparently distinguish the tissues. The loose connective tissue is a tissue that is peeled off as necessary, but in a case where a nerve is damaged in the process of pulling or peeling, a dysfunction may occur after the surgery. For example, a damage to the nervus hypogastricus in the large intestine surgery may cause dysuria. In addition, a damage to the nervus laryngeus recurrens in the esophagectomy or the pneumonectomy may cause dysphagia. Accordingly, it is useful for the operator when information relevant to a recognition result of the loose connective tissue and the nerve tissue can be provided to the operator.

The information processing device 200 according to Embodiment 1 executes the computation by the first learning model 310 and the computation by the second learning model 320 for the same operative field image, derives the integrative recognition result for the operative field image from two computation results, and outputs information based on the derived recognition result, and thus, provides information about the loose connective tissue and the nerve tissue to the operator.

Hereinafter, the configuration of the first learning model 310 and the second learning model 320 will be described.

Figure 4:
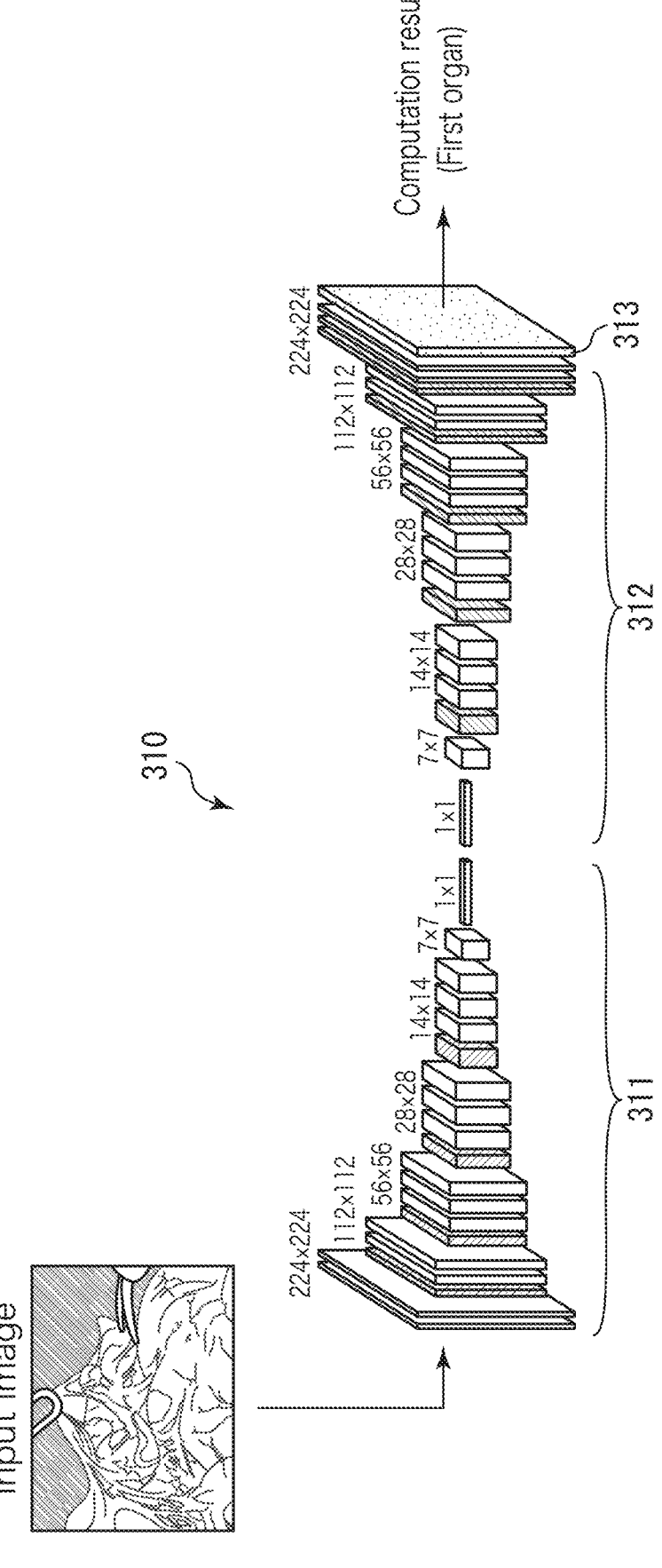
FIG. 4 is a schematic view illustrating a configuration example of a first learning model.

FIG. 4 is a schematic view illustrating a configuration example of the first learning model 310. The first learning model 310 is a learning model for performing image segmentation, and for example, is constructed by a neural network including a convolutional layer such as SegNet. The learning model 310 is not limited to SegNet, and may be constructed by using any neural network capable of performing image segmentation, such as an FCN (Fully Convolutional Network), a U-Net (U-Shaped Network), and a PSPNet (Pyramid Scene Parsing Network). In addition, the learning model 310 may be constructed by using a neural network for object detection such as YOLO (You Only Look Once) and an SSD (Single Shot Multi-Box Detector), instead of the neural network for image segmentation.

The computation by the first learning model 310 is executed in the first computation unit 205. In a case where the operative field image is input, the first computation unit 205 executes the computation, in accordance with the definition information of the first learning model 310 including trained parameters.

The first learning model 310, for example, includes an encoder 311, a decoder 312, and a softmax layer 313. The encoder 311 is configured by alternately arranging a convolutional layer and a pooling layer. The convolutional layer is multilayered into two to three layers. In the example of FIG. 4, the convolutional layer is illustrated without hatching, and the pooling layer is illustrated with hatching.

In the convolutional layer, convolutional computation between data to be input and filters each having a predetermined size (for example, 3×3, 5×5, or the like) is performed. That is, an input value input to a position corresponding to each element of the filter, and a weight coefficient set in advance in the filter are multiplied together for each element, a linear sum of multiplication values for each element is calculated. By adding a set bias to the calculated linear sum, the output of the convolutional layer is obtained. Note that, the result of the convolutional computation may be converted by an activating function. As the activating function, for example, a ReLU (Rectified Linear Unit) can be used. The output of the convolutional layer represents a feature map in which the features of the input data are extracted.

In the pooling layer, the amount of local statistics of the feature map output from the convolutional layer that is a higher layer connected to the input side is calculated. Specifically, a window having a predetermined size (for example, 2×2, 3×3) corresponding to the position of the higher layer is set, and the amount of local statistics is calculated from an input value in the window. As the amount of statistics, for example, the maximum value can be adopted. The size of a feature map output from the pooling layer is reduced (downsampled) in accordance with the size of the window. The example of FIG. 4 illustrates that an input image of 224 pixels×224 pixels is sequentially downsampled to feature maps of 112×112, 56×56, 28×28, . . . , 1×1 by sequentially repeating in the computation of the convolutional layer and the computation of the pooling layer in the encoder 311.

The output (in the example of FIG. 4, the feature map of 1×1) of the encoder 311 is input to the decoder 312. The decoder 312 is configured by alternately arranging a deconvolutional layer and a depooling layer. The deconvolutional layer is multilayered into two to three layers. In the example of FIG. 4, the deconvolutional layer is illustrated without hatching, and the depooling layer is illustrated with hatching.

In the deconvolutional layer, deconvolutional computation is performed with respect to the input feature map. The deconvolutional computation is computation for restoring the feature map before the convolutional computation, under presumption that the input feature map is the result of the convolutional computation using a specific filter. In such computation, when the specific filter is represented in a matrix, a feature map for output is generated by calculating a product between a transposed matrix with respect to the matrix and the input feature map. Note that, a computation result of the deconvolutional layer may be converted by the activating function such as ReLU.

The depooling layers provided in the decoder 312 are individually associated with the pooling layers provided in the encoder 311 on a one-to-one basis, and the associated pairs have substantially the same size. The depooling layer enlarges (upsamples) again the size of the feature map downsampled in the pooling layer of the encoder 311. The example of FIG. 4 illustrates that sequential upsampling to feature maps of $1 \times 1, 7 \times 7, 14 \times 14, \ldots, 224 \times 224$ is performed by sequentially repeating the computation of the convolutional layer and the computation of the pooling layer in the decoder 312.

The output (in the example of FIG. 4, the feature map of $224 \times 224$) of the decoder 312 is input to the softmax layer 313. The softmax layer 313 applies a softmax function to the input value from the deconvolutional layer connected to the input side to output the probability of a label for identifying a site at each position (pixel). The first learning model 310 according to Embodiment 1 may output a probability indicating whether each pixel corresponds to the loose connective tissue from the softmax layer 313, for the input of the operative field image. The computation result by the first learning model 310 is output to the control unit 201.

By extracting a pixel in which the probability of the label output from the softmax layer 313 is a threshold value or more (for example, 60% or more), an image (a recognition image) indicating the recognition result of the loose connective tissue portion is obtained. The first computation unit 205 may render the recognition image of the loose connective tissue portion in the built-in memory (VRAM), and may output the image to the display device 130 through the output unit 207 to display the recognition result of the first learning model 310 on the display device 130. The recognition image is an image having the same size as that of the operative field image, and is generated as an image to which a specific color is allocated to the pixel recognized as the loose connective tissue. It is preferable that the color allocated to the pixel of the loose connective tissue is a color that does not exist inside the human body such that the pixel is distinguished from the organ, the blood vessel, or the like. The color that does not exist inside the human body, for example, is a cold (blue) color such as blue and aqua. In addition, information indicating a permeation rate is applied to each of the pixels configuring the recognition image, an impermeable value is set for the pixel recognized as the loose connective tissue, and a permeable value is set for the other pixels. In a case where the recognition image generated as described above is displayed to be superimposed on the operative field image, it is possible to display the loose connective tissue portion on the operative field image, as a structure having a specific color.

Note that, in the example of FIG. 4, the image of 224 pixels×224 pixels is the input image to the first learning model 310, but the size of the input image is not limited to the above, and can be suitably set in accordance with the processing capability of the information processing device 200, the size of the operative field image obtained from the laparoscope 11, and the like. In addition, the input image to the first learning model 310 is not necessarily the entire operative field image obtained from the laparoscope 11, and may be a partial image generated by cutting out an attention region of the operative field image. Since the attention region including a treatment target is often positioned in the vicinity of the center of the operative field image, for example, a partial image obtained by cutting out the vicinity of the center of the operative field image into a rectangular shape such that the image is approximately half the original size may be used. By decreasing the size of the image input to the first learning model 310, it is possible to improve a recognition accuracy while increasing a processing rate.

Figure 5:
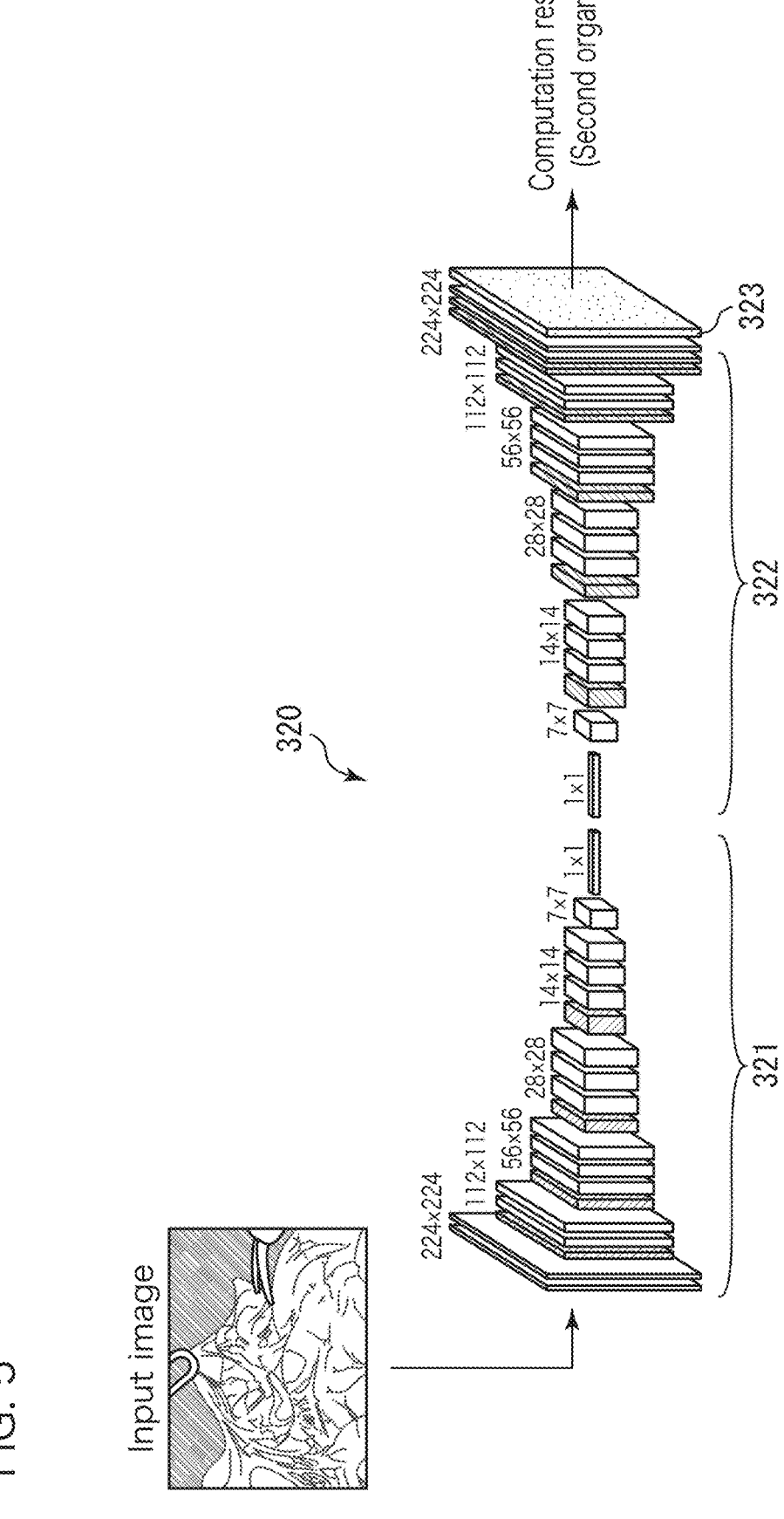
FIG. 5 is a schematic view illustrating a configuration example of a second learning model.

FIG. 5 is a schematic view illustrating a configuration example of the second learning model 320. The second learning model 320 includes an encoder 321, a decoder 322, and a softmax layer 323, and is configured to output information relevant to the nerve tissue portion included in the operative field image, for the input of the operative field image. Since the configuration of the encoder 321, the decoder 322, and the softmax layer 323 provided in the second learning model 320 is the same as that of the first learning model 310, the detailed description thereof will be omitted.

The computation by the second learning model 320 is executed in the second computation unit 206. In a case where the operative field image is input, the second computation unit 206 executes the computation, in accordance with the definition information of the second learning model 320 including trained parameters. The second learning model 320 according to Embodiment 1 may output a probability indicating whether each pixel corresponds to the nerve tissue from the softmax layer 323, for the input of the operative field image. The computation result by the second learning model 320 is output to the control unit 201.

By extracting a pixel in which the probability of a label output from the softmax layer 323 is a threshold value or more (for example, 60% or more), an image (a recognition image) indicating the recognition result of the nerve tissue portion is obtained. The second computation unit 206 may render the recognition image of the nerve tissue portion in the built-in memory (VRAM), and may output the image to the display device 130 through the output unit 207 to display recognition result of the second learning model 320 on the display device 130. The configuration of the recognition image indicating the nerve tissue is the same as that of the loose connective tissue, but it is preferable that a color allocated to the pixel of the nerve tissue is a color that is distinguished from the loose connective tissue (for example, a color such as green or yellow).

Hereinafter, the operation of the information processing device 200 will be described.

Figure 6:
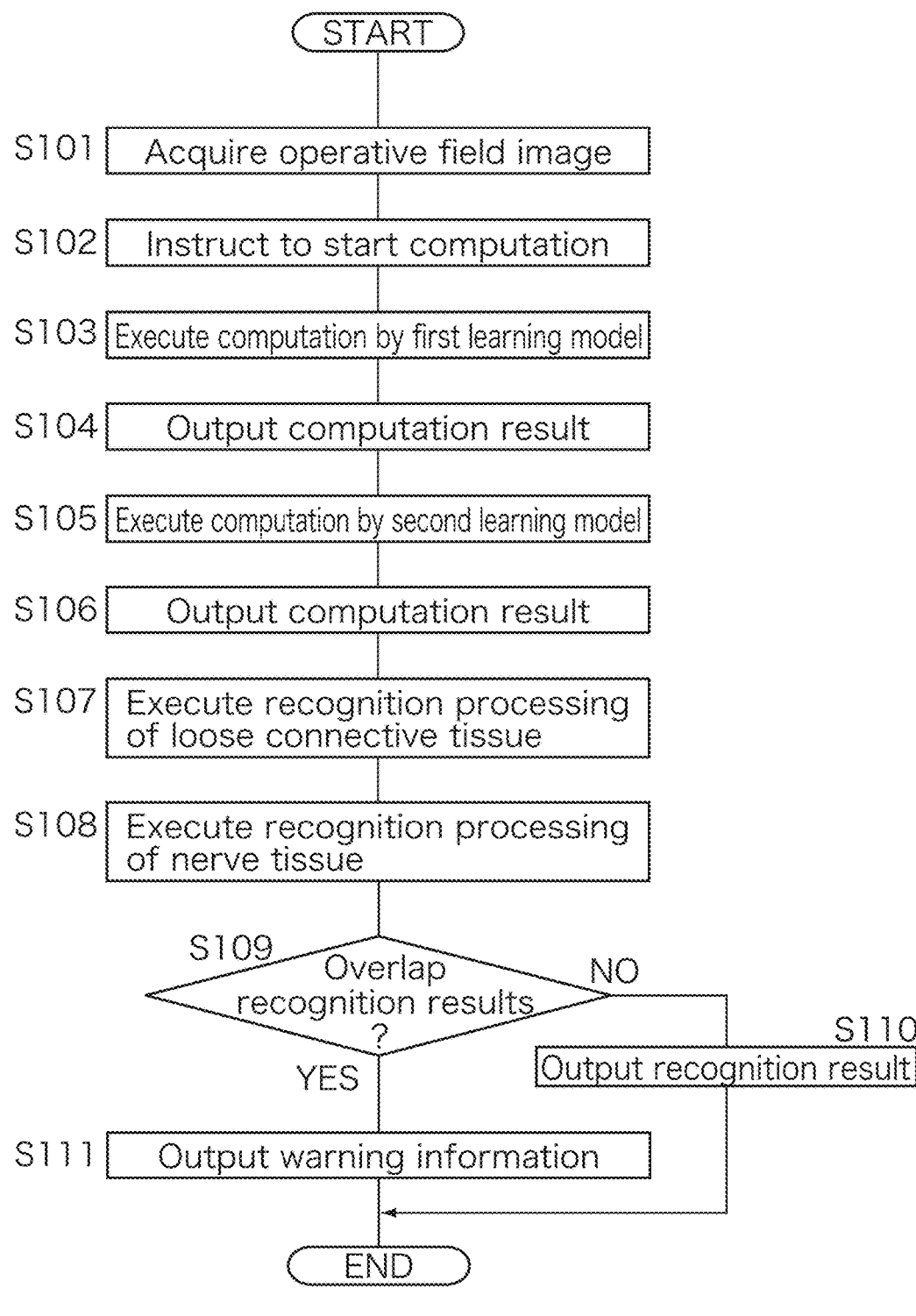
FIG. 6 is a flowchart illustrating a procedure of processing executed by an information processing device according to Embodiment 1.

FIG. 6 is a flowchart illustrating the procedure of the processing executed by the information processing device 200 according to Embodiment 1. The control unit 201 of the information processing device 200 performs the processing, in accordance with the following procedure, by reading out the recognition processing program PG1 and the display processing program PG2 from the storage unit 202 and executing the programs. In a case where the laparoscopic surgery is started, the operative field image obtained by imaging the operative field with the imaging device 11B of the laparoscope 11 is continually output to the CCU 110 through the universal cord 11D. The control unit 201 of the information processing device 200 acquires the operative field image in a frame unit that is output from the CCU 110 by the input unit 204 (step S101). The control unit 201 executes the following processing each time when the operative field image in the frame unit is acquired.

The control unit 201 sends the operative field image in the frame unit that is acquired through the input unit 204 to the first computation unit 205 and the second computation unit 206, and applies a computation start instruction to the first computation unit 205 and the second computation unit 206 (step S102).

In a case where the computation start instruction is applied from the control unit 201, the first computation unit 205 executes the computation by the first learning model 310 (step S103). That is, the first computation unit 205 generates the feature map from the input operative field image, and executes the computation by the encoder 311 in which the generated feature map is sequentially down-sampled, the computation by the decoder 312 in which the feature map input from the encoder 311 is sequentially upsampled, and the computation by the softmax layer 313 in which each pixel of the feature map finally obtained by the decoder 312 is identified. The first computation unit 205 outputs the computation result by the learning model 310 to the control unit 201 (step S104).

In a case where the computation start instruction is applied from the control unit 201, the second computation unit 206 executes the computation by the second learning model 320 (step S105). That is, the second computation unit 206 generates the feature map from the input operative field image, and executes the computation by the encoder 321 in which the generated feature map is sequentially down-sampled, the computation by the decoder 322 in which the feature map input from the encoder 321 is sequentially upsampled, and the computation by the softmax layer 323 in which each pixel of the feature map finally obtained by the decoder 322 is identified. The second computation unit 206 outputs the computation result by the learning model 320 to the control unit 201 (step S106).

In the flowchart of FIG. 6, for convenience, the computation by the first computation unit 205 is executed, and then, the computation by the second computation unit 206 is executed, but the computation by the first computation unit 205 and the computation by the second computation unit 206 may be implemented in a simultaneous and parallel manner.

The control unit 201 derives the integrative recognition result for the operative field image, based on the computation result by the first learning model 310 and the computation result by the second learning model 320. Specifically, the control unit 201 executes the following processing.

The control unit 201 executes the recognition processing of the loose connective tissue, with reference to the computation result by the first learning model 310 (step S107). By extracting the pixel in which the probability of the label output from the softmax layer 313 of the first learning model 310 is the threshold value or more (for example, 60% or more), the control unit 201 is capable of recognizing the loose connective tissue included in the operative field image.

The control unit 201 executes the recognition processing of the nerve tissue, with reference to the computation result by the second learning model 320 (step S108). By extracting the pixel in which the probability of the label output from the softmax layer 323 of the second learning model 320 is the threshold value or more (for example, 60% or more), the control unit 201 is capable of recognizing the nerve tissue included in the operative field image.

The control unit 201 determines whether the recognition result of the loose connective tissue overlaps with the recognition result of the nerve tissue (step S109). In this step, it is checked whether a specific structure included in the operative field image is recognized as the loose connective tissue on the one hand and is recognized as the nerve tissue on the other hand. Specifically, in a case where one pixel in the operative field image is recognized as the loose connective tissue on the one hand and is recognized as the nerve tissue on the other hand, the control unit 201 determines that the recognition results overlap with each other. In addition, it may be determined that the recognition results overlap with each other by comparing a region in the operative field image recognized as the loose connective tissue with a region in the operative field image recognized as the nerve tissue. For example, in a case where the overlap between the recognition results is a predetermined ratio or more (for example 40% or more) at an area ratio, it may be determined that the recognition results overlap with each other, and in a case where the overlap is less than the predetermined ratio, it may be determined that the recognition results do not overlap with each other.

In a case where it is determined that the recognition results do not overlap with each other (S109: NO), the control unit 201 outputs the recognition result of the loose connective tissue and the recognition result of the nerve tissue (step S110). Specifically, the control unit 201 displays the recognition image of the loose connective tissue to be superimposed on the operative field image by applying the instruction to the first computation unit 205, and displays the recognition image of the nerve tissue to be superimposed on the operative field image by applying the instruction to the second computation unit 206. In accordance with the instruction from the control unit 201, the first computation unit 205 and the second computation unit 206 render the recognition images of the loose connective tissue and the nerve tissue in the built-in VRAM, respectively, and output the recognition images to the display device 130 through the output unit 207, and thus, display the recognition images of the loose connective tissue and the nerve tissue to be superimposed on the operative field image.

Figure 7:
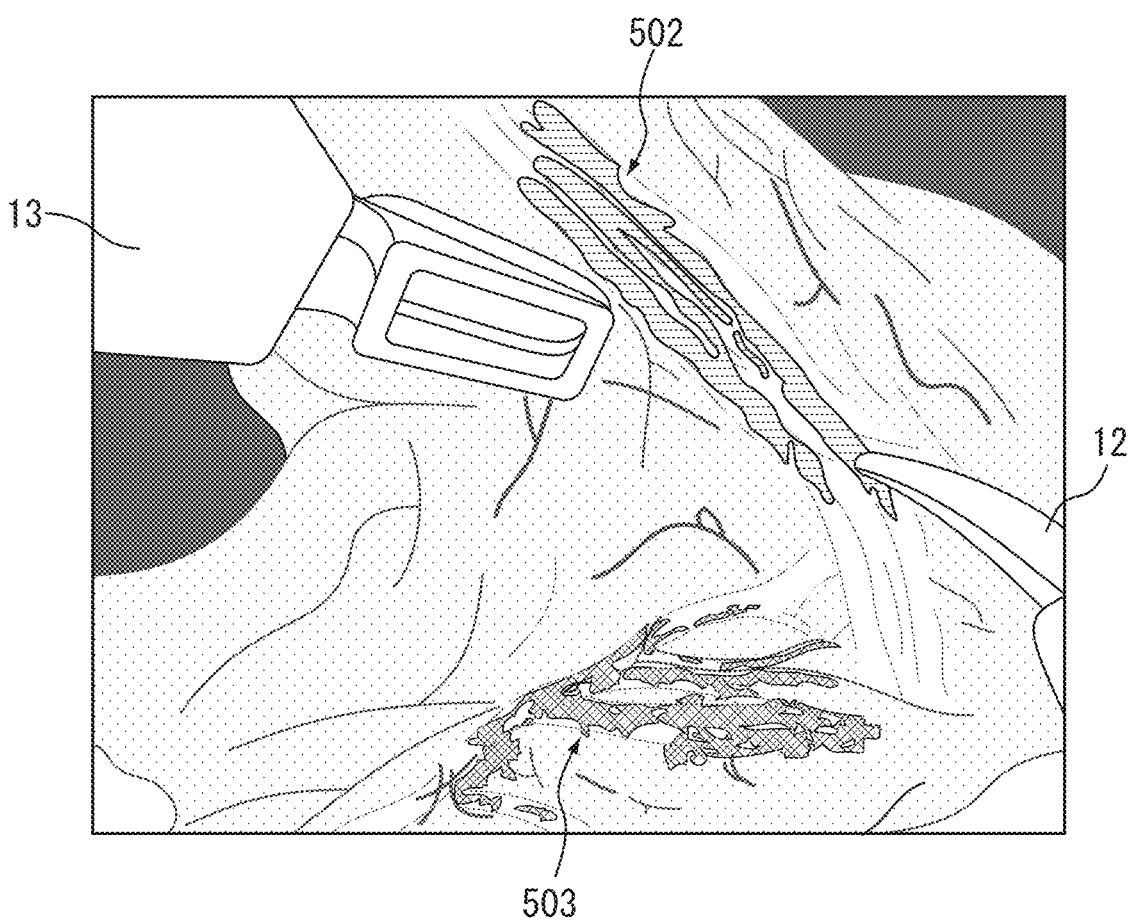
FIG. 7 is a schematic view illustrating a display example of a recognition result in Embodiment 1.

FIG. 7 is a schematic view illustrating a display example of the recognition result in Embodiment 1. In the display example of FIG. 7, for convenience of preparing drawings, a portion recognized as the loose connective tissue 502 is illustrated as a region with hatching, and a portion recognized as the nerve tissue 503 is illustrated as a region with another hatching. In practice, the pixel recognized as the loose connective tissue 502, for example, is displayed in a blue color, and the pixel recognized as the nerve tissue 503, for example, is displayed in a green color. The operator is capable of distinguishing and recognizing the loose connective tissue 502 and the nerve tissue 503 by browsing the recognition results displayed on the display device 130, and for example, is capable of peeling off the loose connective tissue 502 with the energy treatment tool 12 while grasping the presence of the nerve tissue 503 that should not be damaged.

In this embodiment, both of the loose connective tissue recognized based on the computation result of the first computation unit 205 and the nerve tissue recognized based on the computation result of the second computation unit 206 are displayed, but only one thereof may be displayed. In addition, the tissue to be displayed may be selected by the operator, or may be switched by the manipulation of the operator.

In step S109 of the flowchart illustrated in FIG. 6, in a case where it is determined that the recognition results overlap with each other (S109: YES), the control unit 201 outputs the warning information indicating that similar structures are recognized (step S111).

Figure 8:
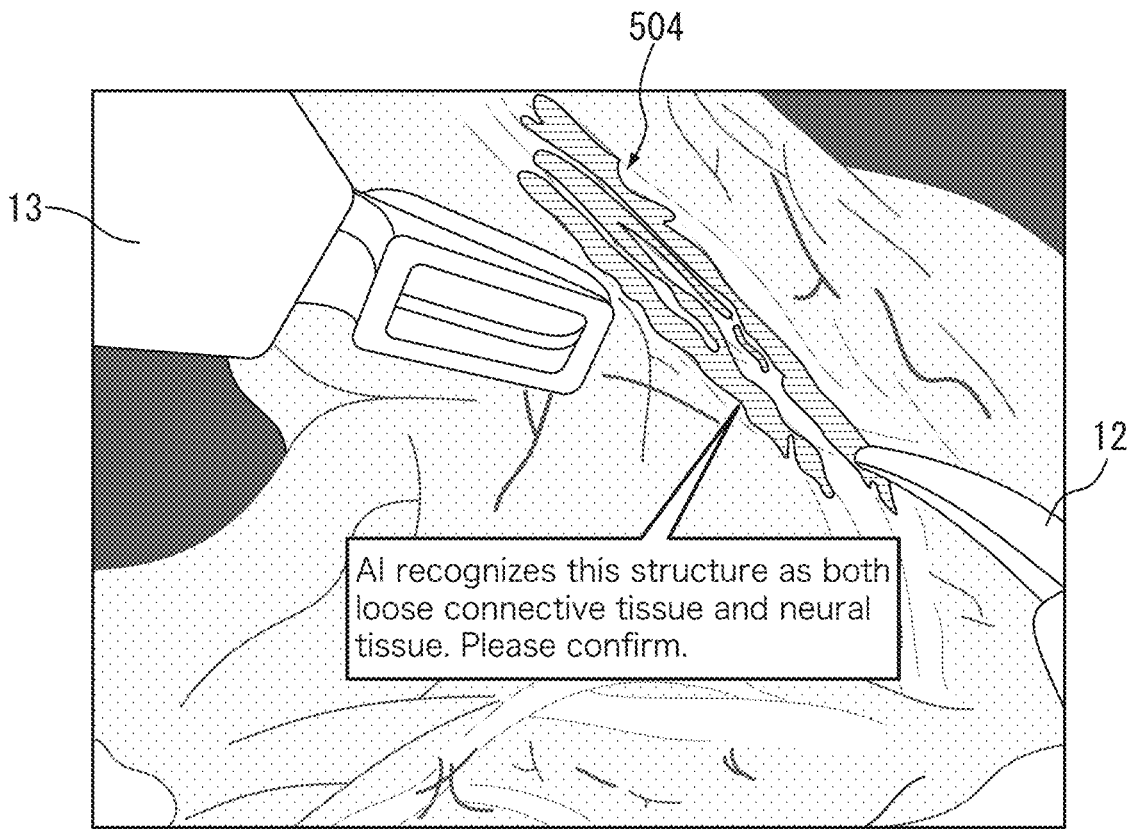
FIG. 8 is a schematic view illustrating a display example of warning information in Embodiment 1.

FIG. 8 is a schematic view illustrating a display example of the warning information in Embodiment 1. FIG. 8 illustrates the display example of the warning information in a case where a structure 504 included in the operative field image is recognized as the loose connective tissue based on the computation result of the first computation unit 205 and is recognized as the nerve tissue based on the computation result of the second computation unit 206. The first learning model 310 used by the first computation unit 205 is trained to output the information relevant to the loose connective tissue, in accordance with the input of the operative field image, and the second learning model 320 used by the second computation unit 206 is trained to output the information relevant to the nerve tissue, in accordance with the input of the operative field image, but the loose connective tissue and the nerve tissue have apparently similar features, and thus, in a case where the recognition processing is independently performed by using two learning models 310 and 320 described above, the recognition results may overlap with each other. In a case where the recognition results overlap with each other, and only one recognition result thereof is presented to the operator, a pixel that is actually the loose connective tissue may be falsely recognized as the nerve tissue, or a pixel that is actually the nerve tissue may be falsely recognized as the loose connective tissue. In a case where the recognition results overlap with each other, the control unit 201 is capable of urging the check of the operator by displaying the warning information as illustrated in FIG. 8.

In the example illustrated in FIG. 8, the control unit 201 displays character information indicating a warning to be superimposed on the operative field image, but the character information indicating the warning may be displayed outside the display region of the operative field image, or the character information indicating the warning may be displayed in another display device (not illustrated). The control unit 201 may display a figure indicating the warning, or may perform warning by the output of a voice or a sound, instead of displaying the character information indicating the warning.

Modification Example 1-1

In a case where the recognition result of the loose connective tissue by the first learning model 310 and the recognition result of the nerve tissue by the second learning model 320 overlap with each other, the control unit 201 of the information processing device 200 may stop the output of the information based on the recognition result.

Modification Example 1-2

In a case where the recognition result of the loose connective tissue by the first learning model 310 and the recognition result of the nerve tissue by the second learning model 320 overlap with each other, the control unit 201 of the information processing device 200 may select the recognition result with a higher confidence, and may output information based on the selected recognition result. The confidence of the recognition result by the first learning model 310 is calculated based on the probability output from the softmax layer 313. For example, the control unit 201 may calculate the confidence by obtaining the average of probability values for each pixel recognized as the loose connective tissue. The same applies to the confidence of the recognition result by the second learning model 320. For example, in a case where as a result of recognizing the structure 504 illustrated in FIG. 8 by the first learning model 310, the structure is recognized as the loose connective tissue by a confidence of 95%, and as a result of recognizing the same structure 504 by the second learning model 320, the structure is recognized as the nerve tissue by a confidence of 62%, the control unit 201 may the recognition result that the structure 504 is the loose connective tissue to the operator.

Modification Example 1-3

Figure 9:
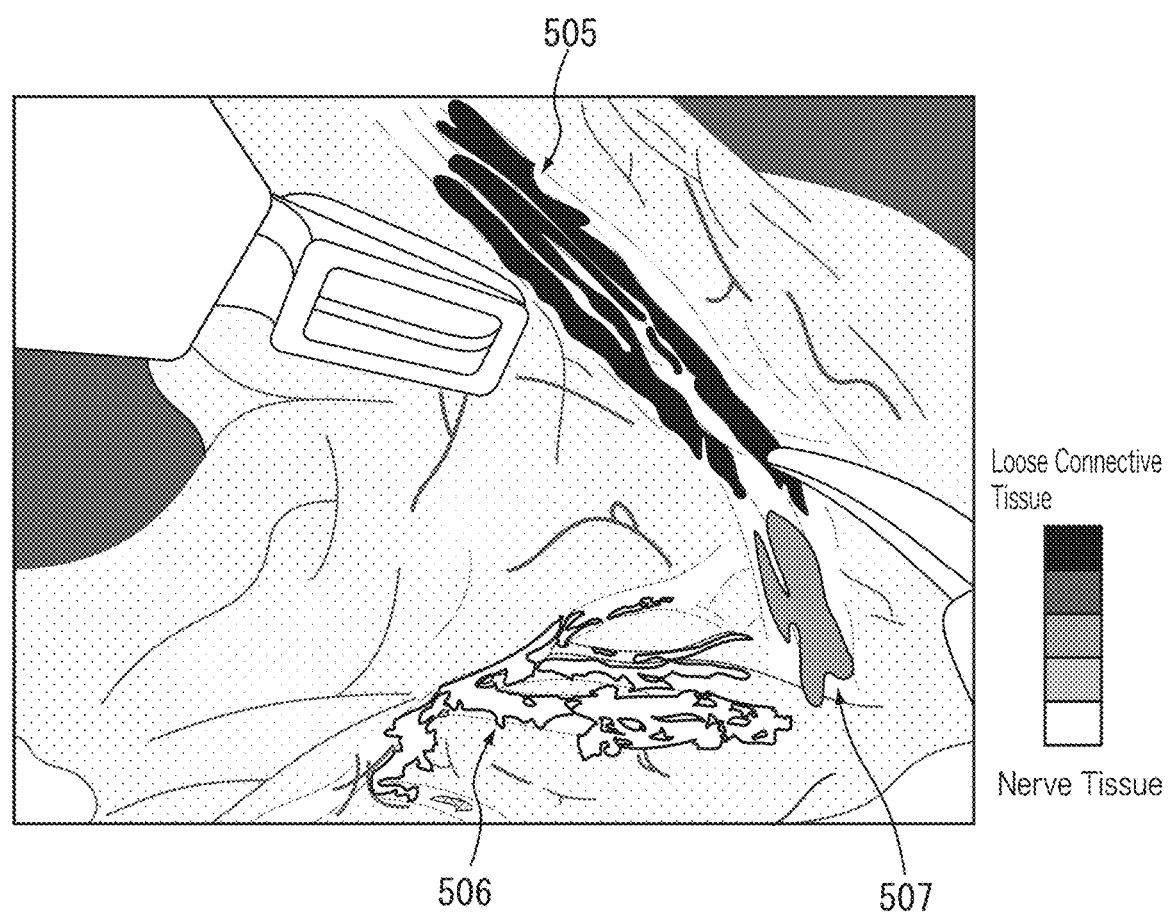
FIG. 9 is a schematic view illustrating a display example of a recognition result according to a confidence.

In a case where the recognition result of the loose connective tissue by the first learning model 310 and the recognition result of the nerve tissue by the second learning model 320 overlap with each other, the control unit 201 of the information processing device 200 may derive the recognition result according to the confidence, and may display the recognition result in a display mode according to the confidence. FIG. 9 is a schematic view illustrating a display example of the recognition result according to the confidence. For example, in a case where as a result of recognizing a structure 505 included in the operative field image by the first learning model 310, the structure is recognized as the loose connective tissue by a confidence of 95%, and as a result of recognizing the same structure 505 by the second learning model 320, the structure is not recognized as the nerve tissue, the control unit 201 presents the structure 505, for example, to the operator by coloring the structure with a blue color (in the drawing, a black color). Similarly, in a case where as a result of recognizing a structure 506 included in the operative field image by the second learning model 320, the structure is recognized as the nerve tissue by a confidence of 90%, and as a result of recognizing the same structure 506 by the first learning model 310, the structure is not recognized as the loose connective tissue, the control unit 201 presents the structure 506, for example, to the operator by coloring the structure with a green color (in the drawing, a white color). On the other hand, as a result of recognizing a structure 507 included in the operative field image by the first learning model 310, the structure is recognized as the loose connective tissue by a confidence of 60%, and as a result of recognizing the same structure 507 by the second learning model 320, the structure is recognized as the nerve tissue by a confidence of 60%, the control unit 201 presents the structure 507, for example, to the operator by coloring the structure with an intermediate color between a blue color and a green color (in the drawing, a grey color). Instead of changing the color in accordance with the confidence, a configuration may be adopted in which a colorfulness, a transparence, or the like is changed.

Modification Example 1-4

In a case where there are the structure recognized as the loose connective tissue and the structure recognized as the nerve tissue, in the operative field image, the control unit 201 of the information processing device 200 may derive information such as a suitable positional relationship between the both structures, a distance to a feature point, a distance to another structure, and the area of another structure from a relationship between the both structures.

As described above, in Embodiment 1, it is possible to acquire the integrative recognition result for the organ included in the operative field, based on the computation result by the first learning model 310 and the computation result by the second learning model 320. In a case where the recognition results for the similar structures overlap with each other, the information processing device 200 performs the warning or stops the output of the information, and thus, it is possible to avoid presenting a result that may be obtained by false recognition to the operator.

Embodiment 2

In Embodiment 2, a configuration will be described in which the integrative recognition result is derived by combining organ recognition with event recognition.

The information processing device 200 according to Embodiment 2 includes a first learning model 310 for recognizing an organ and a third learning model 330 for recognizing an event. The organ recognized by the first learning model 310 is not limited to the loose connective tissue, and may be an organ set in advance. The event recognized by the third learning model 330 is an event such as bleeding, a damage, and a pulsation. The other configuration of the information processing device 200 is the same as that in Embodiment 1, and thus, the description thereof will be omitted.

Figure 10:
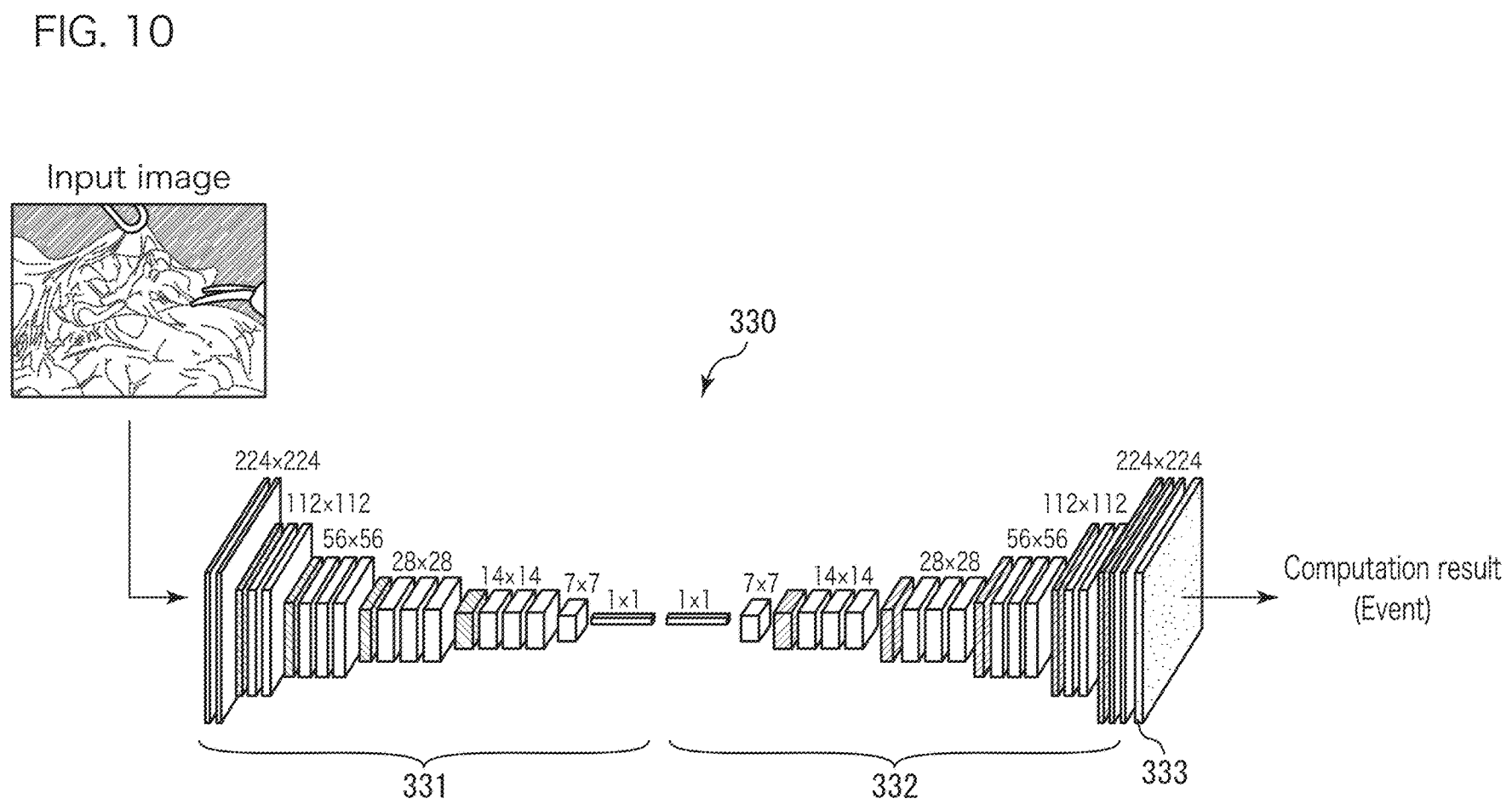

FIG. 10 is a schematic view illustrating a configuration example of the third learning model 330. The third learning model 330 includes an encoder 331, a decoder 332, and a softmax layer 333, and is configured to output information relevant to an event that occurs in the operative field image for the input of the operative field image. The information relevant to the event output from the third learning model 330 is information relevant to the event such as the bleeding, the damage (a burned-out site by the energy treatment tool 12), and the pulsation. The third learning model 330 is not limited to the learning model for the image segmentation or the object detection, and may be a learning model according to CNN (Convolutional Neural Networks), RNN (Recurrent Neural Networks), an LSTM (Long Short Term Memory), a GAN (Generative Adversarial Network), or the like.

Computation by the third learning model 330 is executed in the second computation unit 206. In a case where the operative field image is input, the second computation unit 206 executes the computation, in accordance with definition information of the third learning model 330 including trained parameters. The third learning model 330 may output a probability indicating whether there is an event from the softmax layer 333, for the input of the operative field image. A computation result by the third learning model 330 is output to the control unit 201. In a case where the probability of a label output from the softmax layer 333 is a threshold value or more (for example, 60% or more), the control unit 201 determines that there is an event in the operative field image. The control unit 201 may determine the occurrence of the event in a pixel unit of the operative field image, or may determine the occurrence of the event by using the operative field image as a unit.

Figure 11:
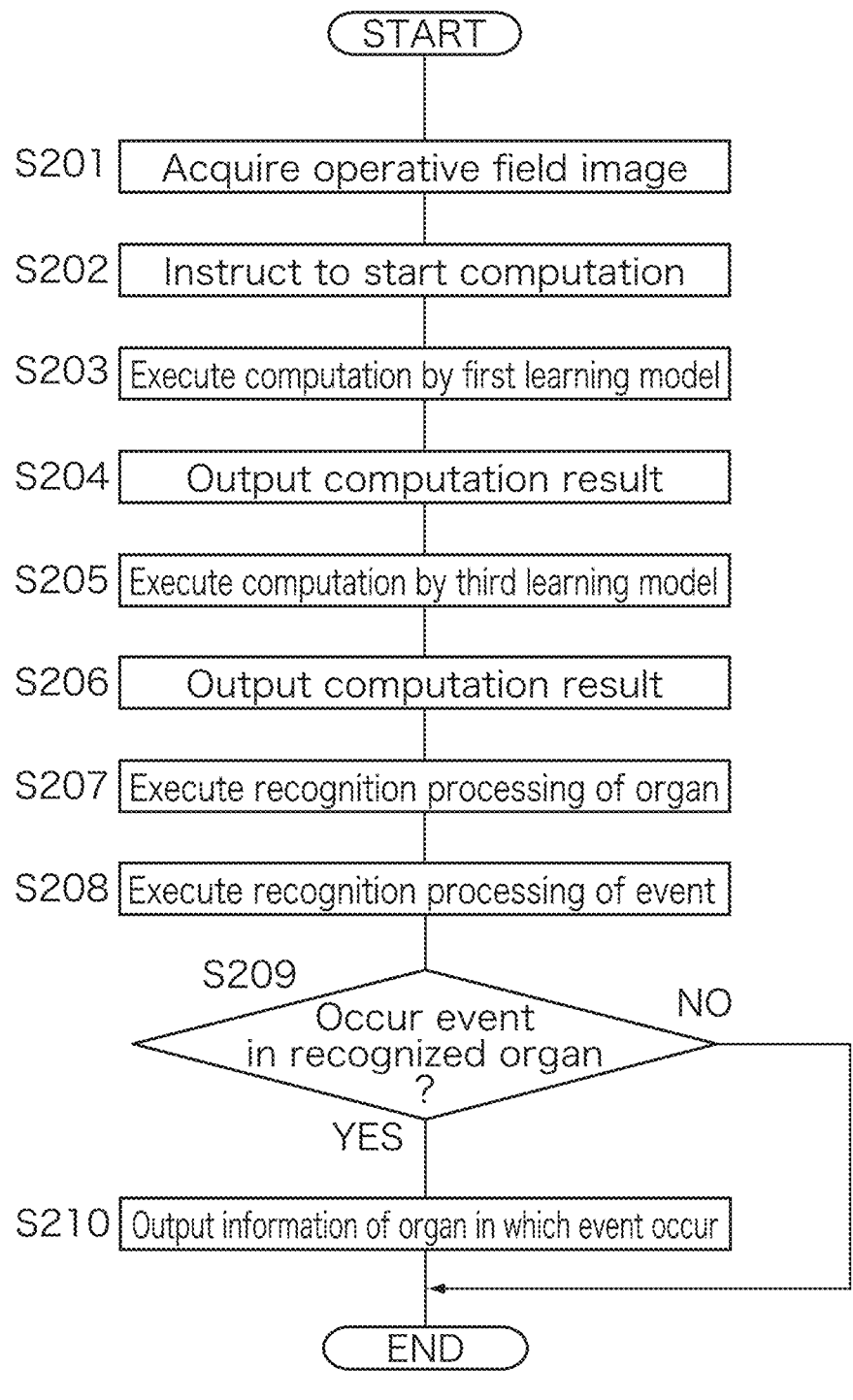
FIG. 11 is a flowchart illustrating a procedure of processing executed by an information processing device according to Embodiment 2.

FIG. 11 is a flowchart illustrating the procedure of the processing executed by the information processing device 200 according to Embodiment 2. The information processing device 200 executes the procedure of steps S201 to S206 as with Embodiment 1, each time when the operative field image is acquired. The control unit 201 of the information processing device 200 acquires the computation result by the first learning model 310 and the computation result by the third learning model 330, and derives the integrative recognition result for the operative field image, based on the computation results. Specifically, the control unit 201 executes the following processing.

The control unit 201 executes the recognition processing of the organ, with reference to the computation result by the first learning model 310 (step S207). By extracting the pixel in which the probability of the label output from the softmax layer 313 of the first learning model 310 is the threshold value or more (for example, 60% or more), the control unit 201 is capable of recognizing the organ included in the operative field image.

The control unit 201 executes the recognition processing of the event, with reference to the computation result by the third learning model 330 (step S208). By extracting a pixel in which the probability of the label output from the softmax layer 333 of the third learning model 330 is the threshold value or more (for example, 60% or more), the control unit 201 is capable of determining the occurrence of the event for each of the pixels.

The control unit 201 determines whether there is an event in the organ recognition in step S207 (step S209). The control unit 201 compares the pixel recognized as the organ in step S207 with the pixel recognized that there is an event in step S208, and in a case where the both pixels are coincident with each other, determines that there is an event in the recognized organ.

In a case where it is determined that there is no event in the recognized organ (S209: NO), the control unit 201 ends the processing according to this flowchart. Note that, the control unit 201 may individually display without associating a recognition result of the organ with the event, or may individually display without associating a recognition result of the event with the organ.

In a case where it is determined that there is an event in the recognized organ (S209: YES), the control unit 201 outputs information of the organ in which an event occurs (step S210). The control unit 201, for example, may display the name of the organ in which an event occurs as the character information to be superimposed on the operative field image. Instead of displaying the name of the organ to be superimposed on the operative field image, the name of the organ in which an event occurs may be displayed outside the operative field image, or may be output by a sound or a voice.

Figure 12:
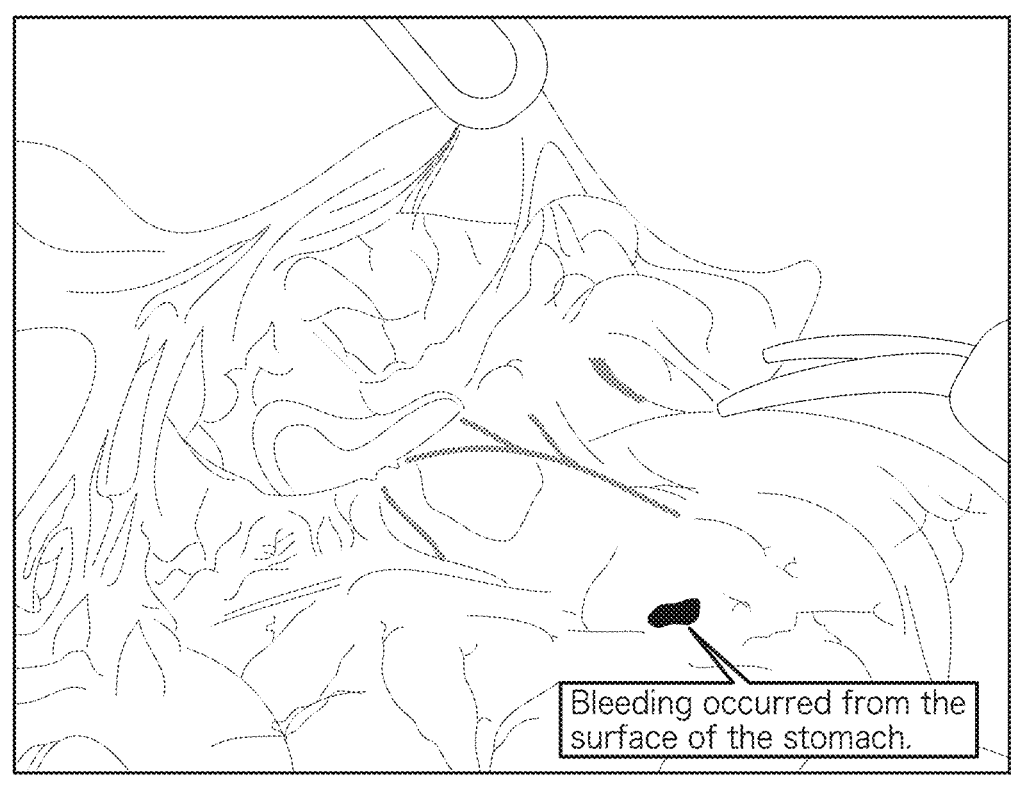
FIG. 12 is a schematic view illustrating a display example of a recognition result in Embodiment 2.

FIG. 12 is a schematic view illustrating a display example of the recognition result in Embodiment 2. The display example of FIG. 12 illustrates an example in which the character information indicating that bleeding occurs from the surface of the stomach is displayed to be superimposed on the operative field image. The control unit 201 may display information of not only an organ in which bleeding occurs, but also an organ damaged by the energy treatment tool 12 or the like, or may display information of an organ in which a pulsation occurs. When displaying the information of the organ such as a blood vessel in which a pulsation occurs, for example, the organ may be displayed by blinking, in synchronization with the pulsation. The synchronization is not necessarily completely coincident with the pulsation, and may be periodic display close to the pulsation.

In a case where bleeding from a specific organ (for example, an important blood vessel) is recognized, the control unit 201 may continually acquire data of vital signs (a beat, a blood pressure, breathing, and a body temperature) of the patient continuously detected by a sensor that is not illustrated, and may display the acquired data on the display device 130. In addition, in a case where the bleeding from the specific organ (for example, the important blood vessel) is recognized, the control unit 201 may notify the recognition result to the external device through the communication unit 208. The external device that is a notification destination may be a terminal carried by an anesthesiologist, or may be an in-hospital server that generally controls evens in the hospital, or the like.

In addition, in a case where the bleeding from the organ is recognized, the control unit 201 may change the threshold value used in the organ recognition, or may stop the organ recognition. Further, in a case where the bleeding from the organ is recognized, it may be difficult to perform the organ recognition, and thus, the control unit 201 may switch to a learning model (not illustrated) improved for bleeding, and may continuously perform the organ recognition by the learning model.

In addition, in a case where there is a risk of anemia for the bleeding, the control unit 201 may automatically estimate the amount of bleeding or a bleeding rate, and may suggest blood transfusion. The control unit 201 is capable of estimating the amount of bleeding by calculating a bleeding area on the image, and is capable of estimating the bleeding rate by calculating a time change in the bleeding area.

As described above, in Embodiment 2, it is possible to present the integrative recognition result obtained by combining the learning model 310 for the organ recognition with the learning model 320 for the event recognition to the operator.

Embodiment 3

In Embodiment 3, a configuration will be described in which the integrative recognition result is derived by combining the organ recognition with device recognition.

The information processing device 200 according to Embodiment 3 includes the first learning model 310 for recognizing the organ and a fourth learning model 340 for recognizing a device. The organ recognized by the first learning model 310 is not limited to the loose connective tissue, and may be an organ set in advance. The device recognized by the fourth learning model 340 is a surgical tool used during the surgery, such as the energy treatment tool 12 and the forceps 13. The other configuration of the information processing device 200 is the same as that in Embodiment 1, and thus, the description thereof will be omitted.

Figure 13:
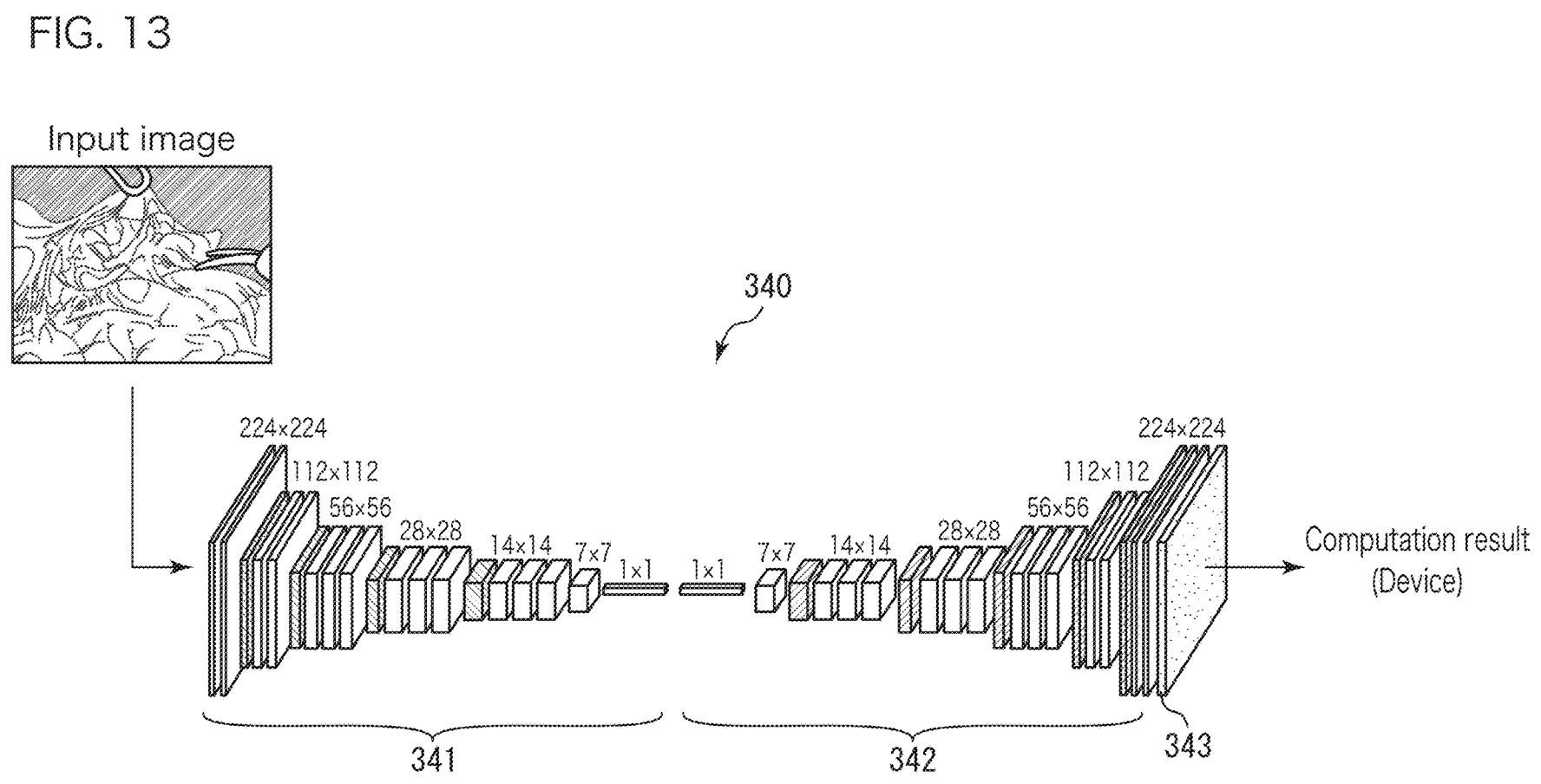

FIG. 13 is a schematic view illustrating a configuration example of the fourth learning model 340. The fourth learning model 340 includes an encoder 341, a decoder 342, and a softmax layer 343, and is configured to output information relevant to a device included in the operative field image for the input of the operative field image. The information relevant to the device output from the fourth learning model 340 is information relevant to the surgical tool used during the surgery, such as the energy treatment tool 12 and the forceps 13. The fourth learning model 340 is not limited to the learning model for the image segmentation or the object detection, and may be a learning model according to CNN, RNN, LSTM, GAN, or the like. A plurality of fourth learning models 340 may be prepared in accordance with the type of device.

Computation by the fourth learning model 340 is executed in the second computation unit 206. In a case where the operative field image is input, the second computation unit 206 executes the computation in accordance with definition information of the fourth learning model 340 including trained parameters. The fourth learning model 340 may output a probability indicating whether each pixel corresponds to a specific device from the softmax layer 343, for the input of the operative field image. A computation result by the fourth learning model 340 is output to the control unit 201. In a case where the probability of a label output from the softmax layer 343 is a threshold value or more (for example, 60% or more), the control unit 201 determines that the specific device included in the operative field image is recognized.

Figure 14:
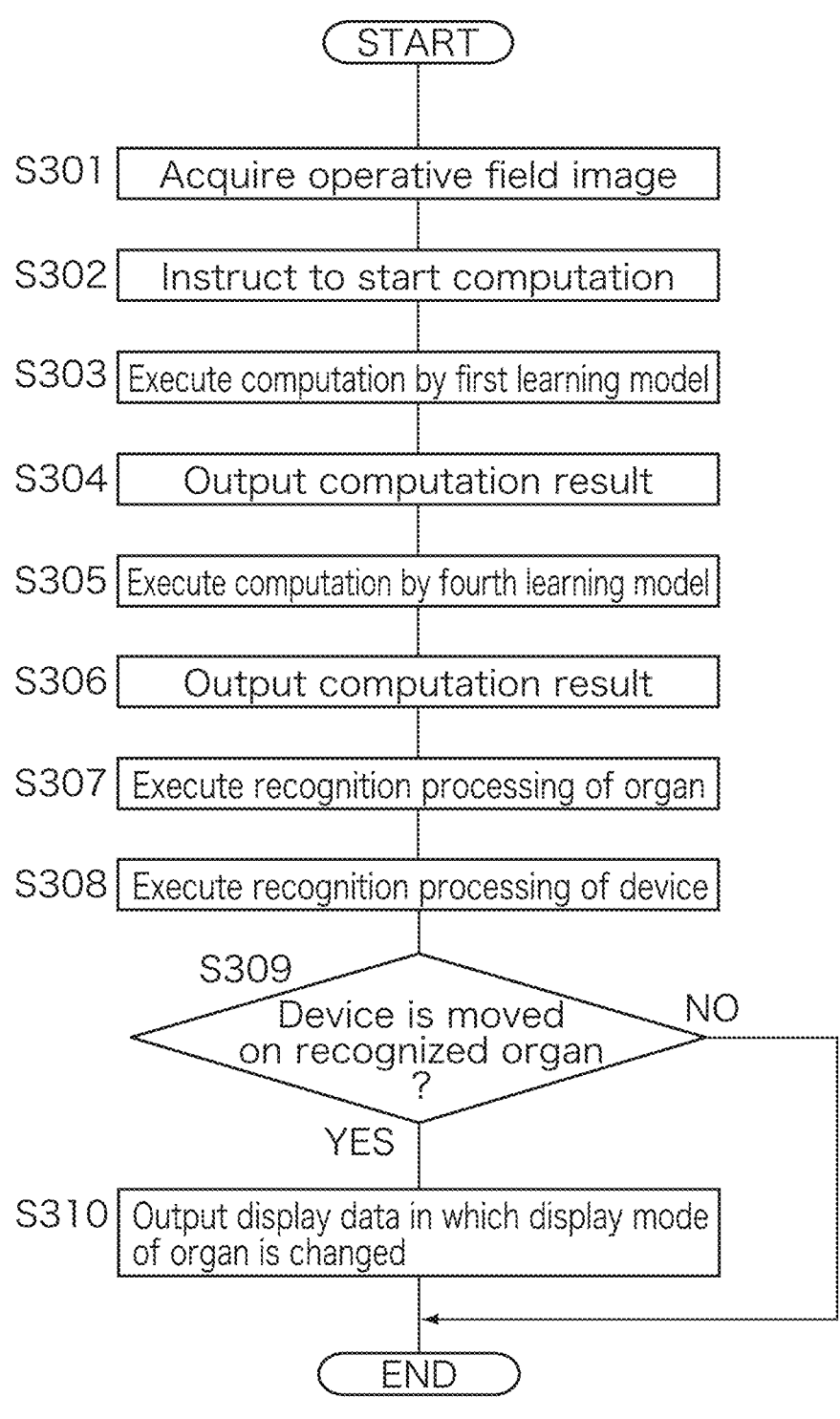
FIG. 14 is a flowchart illustrating a procedure of processing executed by an information processing device according to Embodiment 3.

FIG. 14 is a flowchart illustrating the procedure of the processing executed by the information processing device 200 according to Embodiment 3. The information processing device 200 executes the procedure of steps S301 to S306 as with Embodiment 1, each time when the operative field image is acquired. The control unit 201 of the information processing device 200 acquires the computation result by the first learning model 310 and the computation result by the fourth learning model 340, and derives the integrative recognition result for the operative field image, based on the computation results. Specifically, the control unit 201 executes the following processing. Note that, in the storage unit 202, information of the organ and the device recognized in the recent (for example, one frame before) operative field image are stored.

The control unit 201 executes the recognition processing of the organ, with reference to the computation result by the first learning model 310 (step S307). By extracting the pixel in which the probability of the label output from the softmax layer 313 of the first learning model 310 is the threshold value or more (for example, 60% or more), the control unit 201 is capable of recognizing the organ included in the operative field image.

The control unit 201 executes the recognition processing of the device, with reference to the computation result by the fourth learning model 340 (step S308). By extracting a pixel in which the probability of the label output from the softmax layer 343 of the fourth learning model 340 is the threshold value or more (for example, 60% or more), the control unit 201 is capable of recognizing the device included in the operative field image.

The control unit 201 determines whether the device is moved on the organ recognized in step S307 (step S309). The control unit 201 reads out the information of the organ and the device recognized in the recent operative field image from the storage unit 202, compares the read information of the organ and the device with information of an organ and a device newly recognized, and detects a change in a relative position, and thus, is capable of determining whether the device is moved on the organ.

In a case where it is determined that the device is not moved on the organ (S309: NO), the control unit 201 ends the processing according to this flowchart. Note that, the control unit 201 may display the recognition result of the organ regardless of the device, or may display the recognition result of the device regardless of the organ.

In a case where it is determined that the device is moved on the organ (S309: YES), the control unit 201 generates display data in which the display mode of the organ is changed, and outputs the display data to the display device 130 through the output unit 207 (step S310). The control unit 201 may change the display mode by changing the display color, the colorfulness, and the transparence of the organ, or may change the display mode by displaying the organ by blinking. The organ of which the display mode is changed is displayed on the display device 130. In a case where the device is moved on the organ, the information processing device 200 may falsely recognize the organ, and thus, it is possible to urge the determination of the operator by displaying the organ by changing the display mode. Note that, the control unit 201 may instruct the first computation unit 205 to change the display mode, and may change the display mode by the processing of the first computation unit 205.

Modification Example 3-1

In a case where it is determined that the device is moved (is not stopped) on the organ, the control unit 201 of the information processing device 200 may stop the recognition processing of the organ. In a case where the recognition processing of the organ is stopped, the control unit 201 may continuously perform the recognition processing of the device, and may restart the recognition processing of the organ at a timing when it is determined that the device is stopped.

Modification Example 3-2

In a case where it is determined that the device is moved (is not stopped) on the organ, the control unit 201 of the information processing device 200 may stop output processing of the recognition result of the organ. In this case, the computation by the first learning model 310 and the fourth learning model 340, the recognition processing of the organ based on the computation result of the first learning model 310, and the recognition processing of the device based on the computation result of the fourth learning model 340 are continuously executed, and the display of the recognition image indicating the recognition result of the organ is stopped. The control unit 201 may restart the output processing at a timing when it is determined that the device is stopped.

Modification Example 3-3

The control unit 201 of the information processing device 200 may derive the information of the organ that is processed by the device, based on the recognition processing of the organ and the recognition processing of the device. The control unit 201 is capable of deriving the information of the organ that is processed by the device by comparing a pixel recognized as the organ in step S307 with a pixel recognized as the device in step S308. The control unit 201 may output the information of the organ that is processed by the device, and may display the information, for example, on the display device 130.

Modification Example 3-4

The control unit 201 of the information processing device 200 may acquire dimensional information of the recognized device, and may derive dimensional information of the recognized organ, based on the acquired dimensional information of the device.

Figure 15:
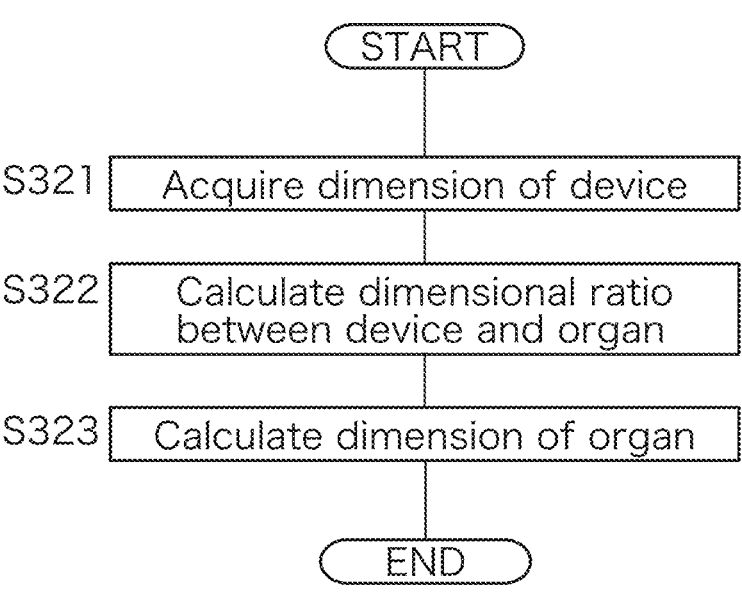
FIG. 15 is a flowchart illustrating a derivation procedure of dimensional information.

FIG. 15 is a flowchart illustrating a derivation procedure of the dimensional information. The control unit 201 acquires the dimensional information of the recognized device (step S321). The dimensional information of the device may be stored in advance in the storage unit 202 of the information processing device 200, or may be stored in the external device. In the former case, the control unit 201 may acquire the dimensional information by reading out desired information from the storage unit 202, and in the latter case, the control unit 201 may acquire the dimensional information by accessing the external device. Note that, the dimensional information is not necessarily the dimension of the entire device, and may be the dimension of a part of the device (for example, a knife-point portion).

The control unit 201 calculates a ratio between the dimension of image information of the device portion indicated by the acquired dimensional information and the dimension of the recognized organ on the image (step S322).

The control unit 201 calculates the dimension of the organ, based on the dimensional information of the device acquired in step S321, and the dimensional ratio calculated in step S322 (step S323). The control unit 201 may output the calculated dimensional information of the organ, and may display the information, for example, on the display device 130.

Modification Example 3-5

The control unit 201 of the information processing device 200 may derive information of the organ damaged by the device, based on the recognition processing of the organ and the recognition processing of the device. For example, in a case where the device on the organ is recognized, and it is determined that a part of the organ is discolored, the control unit 201 determines that the organ damage due to the device is detected. The device on the organ is recognized by the same procedure as the procedure illustrated in the flowchart of FIG. 14. In addition, the discoloration of the organ is recognized by a temporal change in a pixel value. In a case where the organ damage due to the device is detected, the control unit 201 outputs information indicating that the organ damage due to the device is detected, and displays the information, for example, on the display device 130.

Modification Example 3-6

The control unit 201 of the information processing device 200 may derive information indicating whether the device used on the organ is suitable, based on the recognition processing of the organ and the recognition processing of the device. The storage unit 202 of the information processing device 200 includes a definition table in which a relationship between the type of organ and a device that can be used (or a device that is not to be used) on each organ is defined. In the definition table, for example, it is defined that sharp forceps are not to be used on the enteric canal. The control unit 201 recognizes the organ and the device from the operative field image, and determines whether the device used on the organ is suitable, with reference to the definition table described above. In a case where it is determined that the device is not suitable (for example, in a case where the sharp forceps are used on the enteric canal), the control unit 201 outputs information indicating that an unsuitable device is used, and displays the information, for example, on the display device 130. In addition, the control unit 201 may issue a warning by a voice or a warning sound.

Modification Example 3-7

In a case where the device is recognized, the control unit 201 of the information processing device 200 may output manipulation assistance information of the device, and may display the information, for example, on the display device 130. The manipulation assistance information of the device is use instructions of the device, and may be stored in the storage unit 202 of the information processing device 200 or the external device.

As described above, in Embodiment 3, it is possible to present the integrative recognition result obtained by combining the learning model 310 for the organ recognition with the learning model 340 for the device recognition to the operator.

Embodiment 4

In Embodiment 4, a configuration will be described in which the integrative recognition result is derived by combining the organ recognition with scene recognition.

The information processing device 200 according to Embodiment 4 includes the first learning model 310 for recognizing the organ and a fifth learning model 350 for recognizing a scene. The organ recognized by the first learning model 310 is not limited to the loose connective tissue, and may be an organ set in advance. The first learning model 310 may be prepared for each type of organ to respond to various organs. The scene recognized by the fifth learning model 350, for example, is a characteristic scene indicating a characteristic scene of the surgery. The other configuration of the information processing device 200 is the same as that in Embodiment 1, and thus, the description thereof will be omitted.

Figure 16:
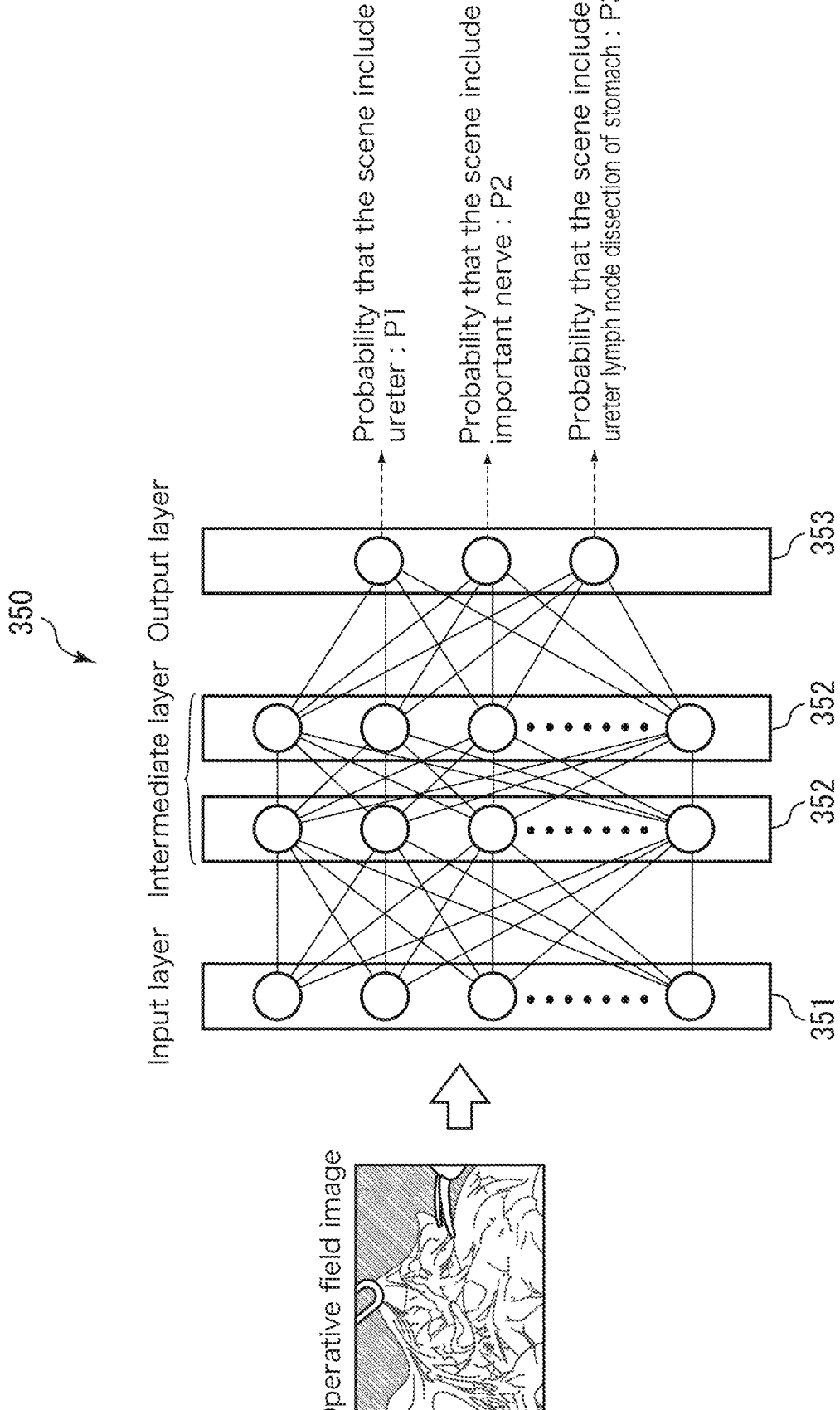
FIG. 16 is a schematic view illustrating a configuration example of a fifth learning model.

FIG. 16 is a schematic view illustrating a configuration example of the fifth learning model 350. The fifth learning model 350 includes an input layer 351, an intermediate layer 352, and an output layer 353, and is configured to output information relevant to a scene represented by the operative field image for the input of the operative field image. The information relevant to the scene output from the fifth learning model 350 is information such as a probability that the scene includes a specific organ such as a blood vessel, an important nerve, a peculiar organ (the ureter, the spleen, or the like), a probability that in the scene, a characteristic manipulation is performed in a specific surgery such as vascular interruption and lymph node dissection, and a probability that in the scene, a characteristic manipulation (vascular ligation, intestinal interruption, anastomosis, and the like) is performed by using a specific surgery device (a vascular clip, an automatic anastomosis device, and the like). The fifth learning model 350, for example, is constructed by CNN. Alternatively, fifth the learning model 350 may be a learning model constructed by RNN, LSTM, GAN, or the like, and may be the learning model for the image segmentation or the object detection.

Computation by the fifth learning model 350 is executed in the second computation unit 206. In a case where the operative field image is input, the second computation unit 206 executes the computation, in accordance with definition information of the fifth learning model 350 including trained parameters. The fifth learning model 350 outputs a probability corresponding to a specific scene from each node configuring the output layer 353, for the input of the operative field image. A computation result by the fifth learning model 350 is output to the control unit 201. The control unit 201 performs the scene recognition by selecting a scene having the highest probability among the probabilities of each of the scenes output from the output layer 353.

Figure 17:
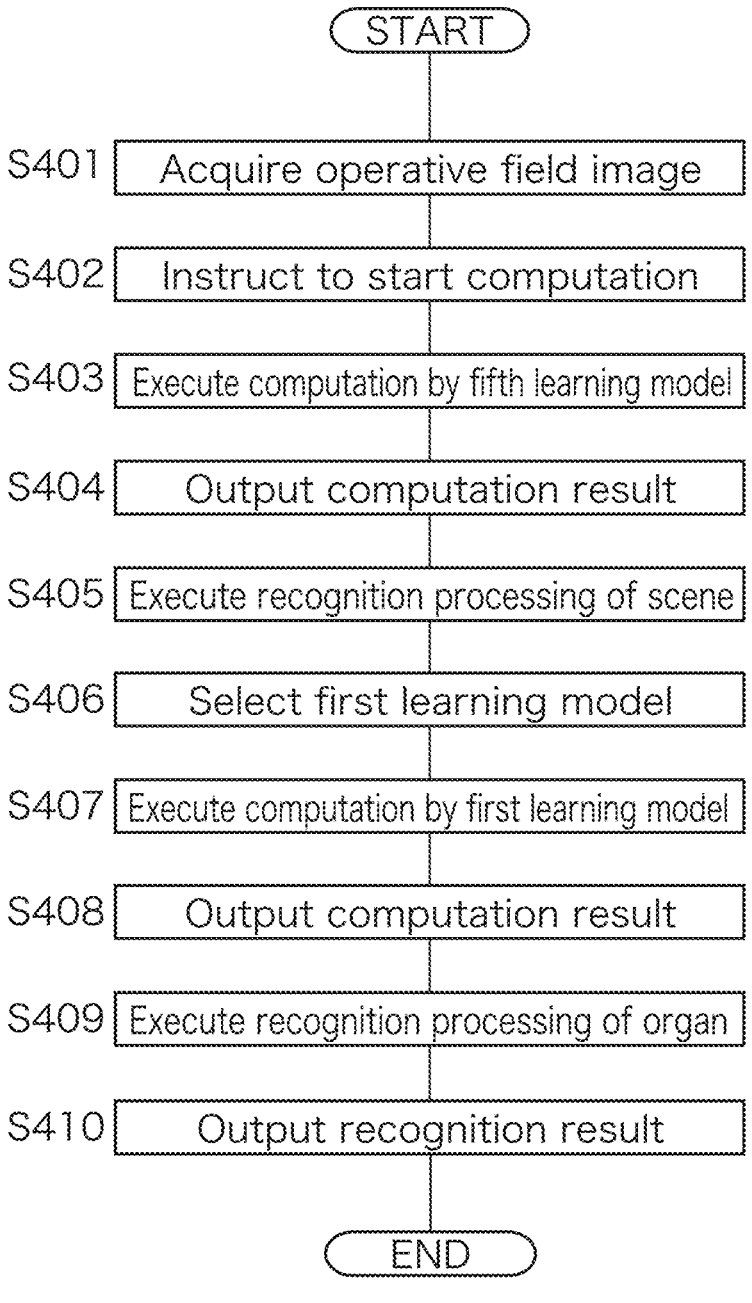
FIG. 17 is a flowchart illustrating a procedure of processing executed by an information processing device according to Embodiment 4.

FIG. 17 is a flowchart illustrating the procedure of the processing executed by the information processing device 200 according to Embodiment 4. The control unit 201 of the information processing device 200 acquires the operative field image in the frame unit output from the CCU 110 by the input unit 204 (step S401). The control unit 201 executes the following processing, each time when the operative field image in the frame unit is acquired.

The control unit 201 sends the operative field image in the frame unit that is acquired through the input unit 204 to the first computation unit 205 and the second computation unit 206, and applies the computation start instruction to the second computation unit 206 (step S402).

In a case where the computation start instruction is applied from the control unit 201, the second computation unit 206 executes the computation by the fifth learning model 350 (step S403). That is, the first computation unit 205 executes each computation in the input layer 351, the intermediate layer 352, and the output layer 353 configuring the fifth learning model 350, and outputs the probability corresponding to the specific scene from each node of the output layer 353. The second computation unit 206 outputs the computation result by the fifth learning model 350 to the control unit 201 (step S404).

The control unit 201 executes the recognition processing of the scene, based on the computation result by the second computation unit 206 (step S405). That is, the control unit 201 specifies a scene represented by the current operative field image by selecting the scene having the highest probability among the probabilities of each of the scenes output from the output layer 353.

The control unit 201 selects the learning model for the organ recognition, in accordance with the specified scene (step S406). For example, in a case where the scene recognized in step S405 is a scene including the ureter, the control unit 201 selects a learning model for ureter recognition. In addition, in a case where the scene recognized in step S405 is a lymph node dissection scene of the upper border of the pancreas in a stomach cancer surgery, the control unit 201 selects a learning model for lymphaden recognition, a learning model for pancreas recognition, a learning model for stomach recognition, and the like. In addition, in a case where the scene recognized in step S405 is a scene of performing ligation by using a vascular clip, the control unit 201 selects a learning model for blood vessel recognition, a learning model for a surgery device, and the like. The control unit 201 is capable of selecting the learning model for the organ recognition, in accordance with not only the ureter, the lymphaden, the pancreas, and the stomach, but also the specified scene. Hereinafter, the learning model for the organ recognition that is selected in step S406 is set to the first learning model 310. The control unit 201 applies the computation start instruction to the first computation unit 205, together with the information of the selected first learning model 310.

In a case where the computation start instruction is applied from the control unit 201, the first computation unit 205 executes the computation by the first learning model 310 (step S407). That is, the first computation unit 205 generates a feature map from the input operative field image, and executes the computation by the encoder 311 in which the generated feature map is sequentially downsampled, the computation by the decoder 312 in which the feature map input from the encoder 311 is sequentially upsampled, and the computation by the softmax layer 313 in which each pixel of the feature map finally obtained by the decoder 312 is identified. The first computation unit 205 outputs the computation result by the learning model 310 to the control unit 201 (step S408).

The control unit 201 executes the recognition processing of the organ, with reference to the computation result by the first learning model 310 (step S409). By extracting the pixel in which the probability of the label output from the softmax layer 313 of the first learning model 310 is the threshold value or more (for example, 60% or more), the control unit 201 is capable of recognizing the organ included in the operative field image.

The control unit 201 outputs the recognition result of the organ (step S410). Specifically, the control unit 201 displays the recognition image of the organ to be superimposed on the operative field image by applying the instruction to the first computation unit 205. In accordance with the instruction from the control unit 201, the first computation unit 205 renders the recognition image of the organ in the built-in VRAM, outputs the recognition image to the display device 130 through the output unit 207 to display the recognition image of the organ to be superimposed on the operative field image. In addition, an instruction for the end of the computation of the first learning model or the start of another learning model may be applied by using a learning model that recognizes the end of the specific scene.

Modification Example 4-1

In a case where the information processing device 200 is configured to perform the recognition processing of the specific organ (that is, in the case of including only one first learning model 310), the organ recognition processing is not performed until the scene including the specific organ is recognized.

Figure 18:
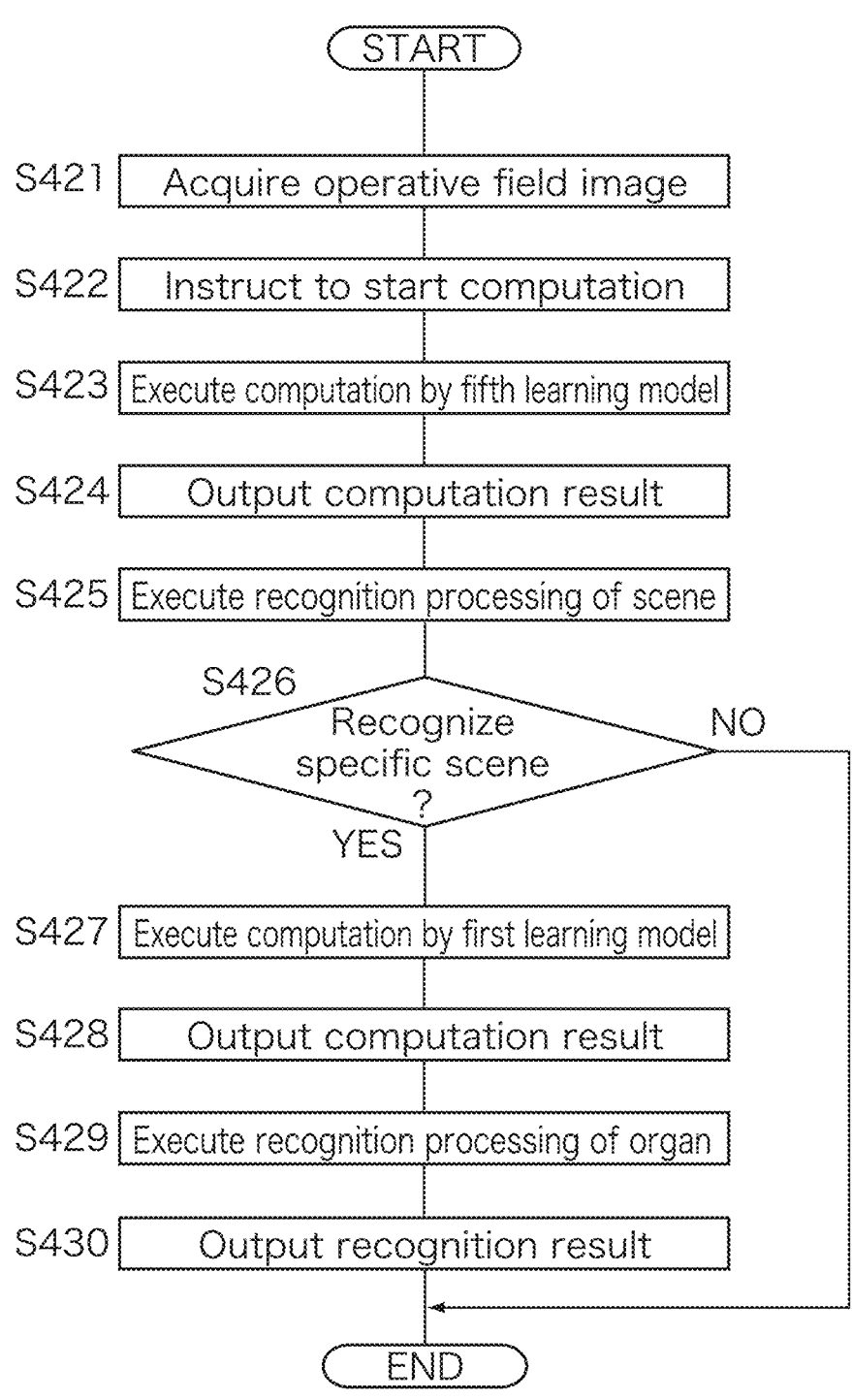
FIG. 18 is a flowchart illustrating a processing procedure in Modification Example 4-1.

FIG. 18 is a flowchart illustrating a processing procedure in Modification Example 4-1. In the same procedure as the procedure illustrated in FIG. 17, the control unit 201 of the information processing device 200 executes the scene recognition processing, each time when the operative field image is acquired (steps S421 to S425).

The control unit 201 determines whether the specific scene by the scene recognition processing is recognized (step S426). The control unit 201, for example, may determine whether it is a scene set in advance, such as the scene including the ureter, the lymph node dissection scene, and the scene of performing the ligation by using the vascular clip. In a case where it is determined that the specific scene is not recognized (S426: NO), the control unit 201 ends the processing according to this flowchart. On the other hand, in a case where it is determined that the specific scene is recognized (S426: YES), the control unit 201 applies the computation start instruction to the first computation unit 205.

In a case where the computation start instruction is applied from the control unit 201, the first computation unit 205 executes the computation by the first learning model 310 (step S427), and outputs the computation result by the learning model 310 to the control unit 201 (step S428).

The control unit 201 executes the recognition processing of the organ, with reference to the computation result by the first learning model 310 (step S429). By extracting the pixel in which the probability of the label output from the softmax layer 313 of the first learning model 310 is the threshold value or more (for example, 60% or more), the control unit 201 is capable of recognizing the organ included in the operative field image.

The control unit 201 outputs the recognition result of the organ (step S430). Specifically, the control unit 201 displays the recognition image of the organ to be superimposed on the operative field image by applying the instruction to the first computation unit 205. In accordance with the instruction from the control unit 201, the first computation unit 205 renders the recognition image of the organ in the built-in VRAM, and outputs the recognition image to the display device 130 through the output unit 207 to display the recognition image of the organ to be superimposed on the operative field image.

Modification Example 4-2

The control unit 201 of the information processing device 200 may acquire preliminary information, in accordance with the recognition result of the scene recognition processing, and may perform the organ recognition processing, with reference to the acquired preliminary information. FIG. 19 is a conceptual diagram illustrating an example of a preliminary information table. In the preliminary information table, the preliminary information is registered in accordance with the scene of the surgery. In a case where the lymph node dissection of the upper border of the pancreas is performed in the stomach cancer surgery, the pancreas exists under the lymph node. In the preliminary information table, for example, the preliminary information indicating that the pancreas exists under the lymphaden is registered regarding the lymph node dissection scene of the upper border of the pancreas in the stomach cancer surgery. In the preliminary information table, not only the information illustrated in FIG. 19, but also various preliminary information pieces according to various scenes are registered. The preliminary information table may be prepared in the storage unit 202 of the information processing device 200, or may be prepared in the external device.

Figure 20:
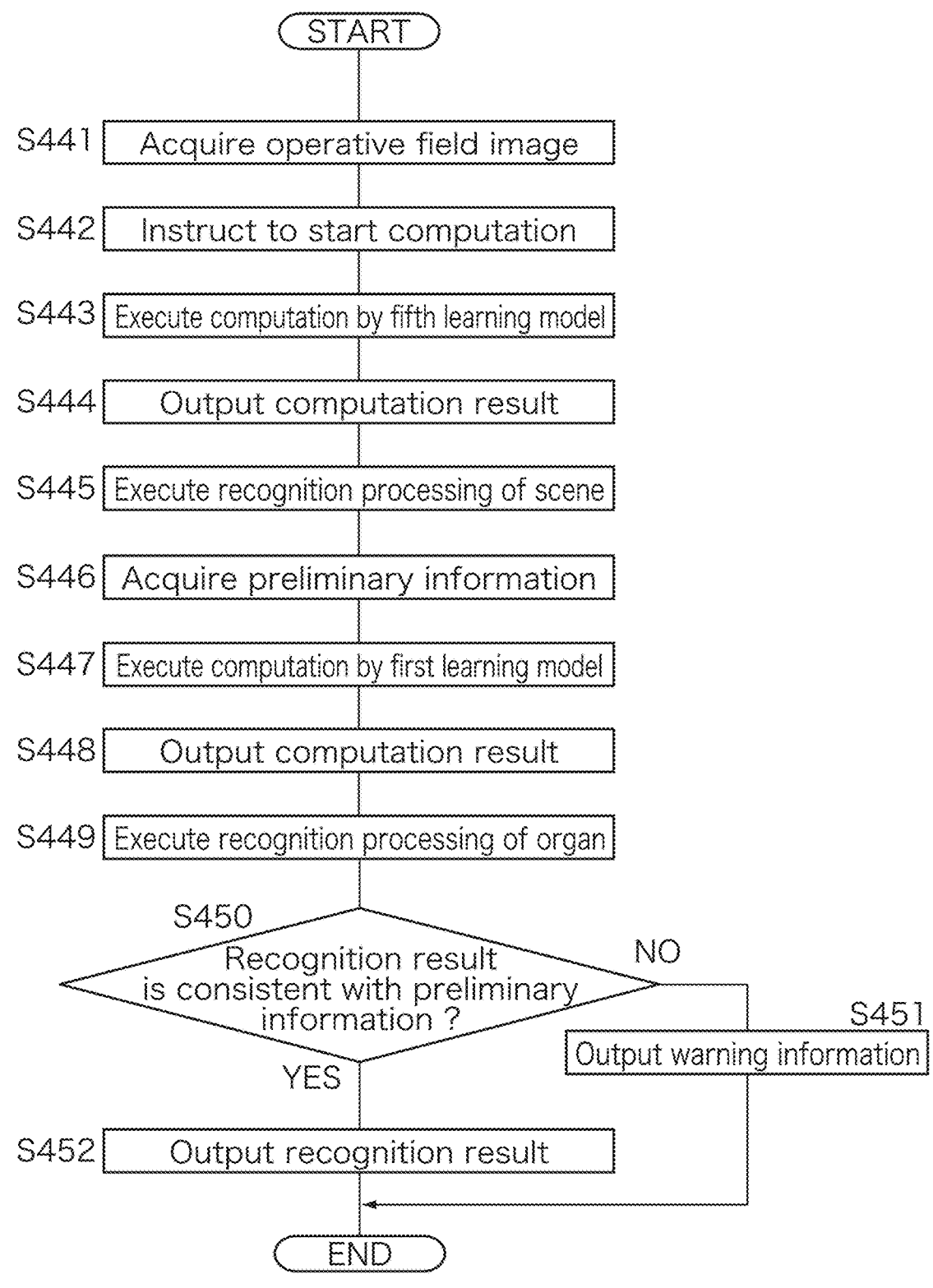
FIG. 20 is a flowchart illustrating a processing procedure in Modification Example 4-2.

FIG. 20 is a flowchart illustrating a processing procedure in Modification Example 4-2. In the same procedure as the procedure illustrated in FIG. 17, the control unit 201 of the information processing device 200 executes the scene recognition processing, each time when the operative field image is acquired (steps S441 to S445).

The control unit 201 accesses the storage unit 202 or the external device, and acquires the preliminary information, in accordance with the recognized scene (step S446). After the preliminary information is acquired, the control unit 201 applies the computation start instruction to the first computation unit 205.

In a case where the computation start instruction is applied from the control unit 201, the first computation unit 205 executes the computation by the first learning model 310 (step S447), and outputs the computation result by the first learning model 310 to the control unit 201 (step S448).

The control unit 201 executes the recognition processing of the organ, with reference to the computation result by the first learning model 310 (step S449). By extracting the pixel in which the probability of the label output from the softmax layer 313 of the first learning model 310 is the threshold value or more (for example, 60% or more), the control unit 201 is capable of recognizing the organ included in the operative field image.

The control unit 201 determines whether the recognition result of the organ is consistent with the preliminary information (step S450). For example, in the lymph node dissection scene of the upper border of the pancreas in the stomach cancer surgery, in a case where the pancreas existing on the lymphaden is recognized even though the preliminary information indicating that the pancreas exists under the lymphaden is obtained, the control unit 201 is capable of determining that the recognition result of the organ is not consistent with the preliminary information.

In a case where it is determined that the recognition result of the organ is not consistent with the preliminary information (S450: NO), the control unit 201 outputs the warning information (step S451). The control unit 201 outputs the character information indicating that the recognition result of the organ is not consistent with the preliminary information from the output unit 207, and displays the information to be superimposed in the display region of the operative field image. The control unit 201 may display the character information indicating the warning outside the display region of the operative field image, or may display the character information indicating the warning on another display device (not illustrated). The control unit 201 may display the figure indicating the warning, or may perform the warning by the output of a voice or a sound, instead of displaying the character information indicating the warning.

In this embodiment, in a case where the recognition result of the organ is not consistent with the preliminary information, the warning information is output, but in a case where the recognition result of the organ is not consistent with the preliminary information, there is a possibility of false recognition, and thus, the output processing of the recognition result of the organ may be stopped. In this case, the computation by the first learning model 310 and the fifth learning model 350, the recognition processing of the organ based on the computation result of the first learning model 310, and the recognition processing of the scene based on the computation result of the fifth learning model 350 are continuously executed, but the display of the recognition image indicating the recognition result of the organ is stopped. In addition, the control unit 201 may stop the recognition processing of the organ, instead of stopping the output processing.

In a case where it is determined that the recognition processing of the organ is consistent with the preliminary information (S450: YES), the control unit 201 outputs the recognition result of the organ (step S452). Specifically, the control unit 201 displays the recognition image of the organ to be superimposed on the operative field image by applying the instruction to the first computation unit 205. In accordance with the instruction from the control unit 201, the first computation unit 205 renders the recognition image of the organ in the built-in VRAM, and outputs the recognition image to the display device 130 through the output unit 207 to display the recognition image of the organ to be superimposed on the operative field image.

In the flowchart of FIG. 20, the preliminary information is referred to after the recognition processing of the organ is executed, but the preliminary information may be referred to when executing the recognition processing of the organ. For example, in a case where the preliminary information indicating that the pancreas exists under the lymphaden is obtained, the control unit 201 may generate mask information to exclude the upper portion of the lymphaden from the recognition target, and may apply the computation start instruction to the first computation unit 205, together with the generated mask information. The first computation unit 205 may apply a mask to the operative field image, and may execute the computation by the first learning model 310, based on a partial image of a region other than the masked region.

Modification Example 4-3

Figure 21:
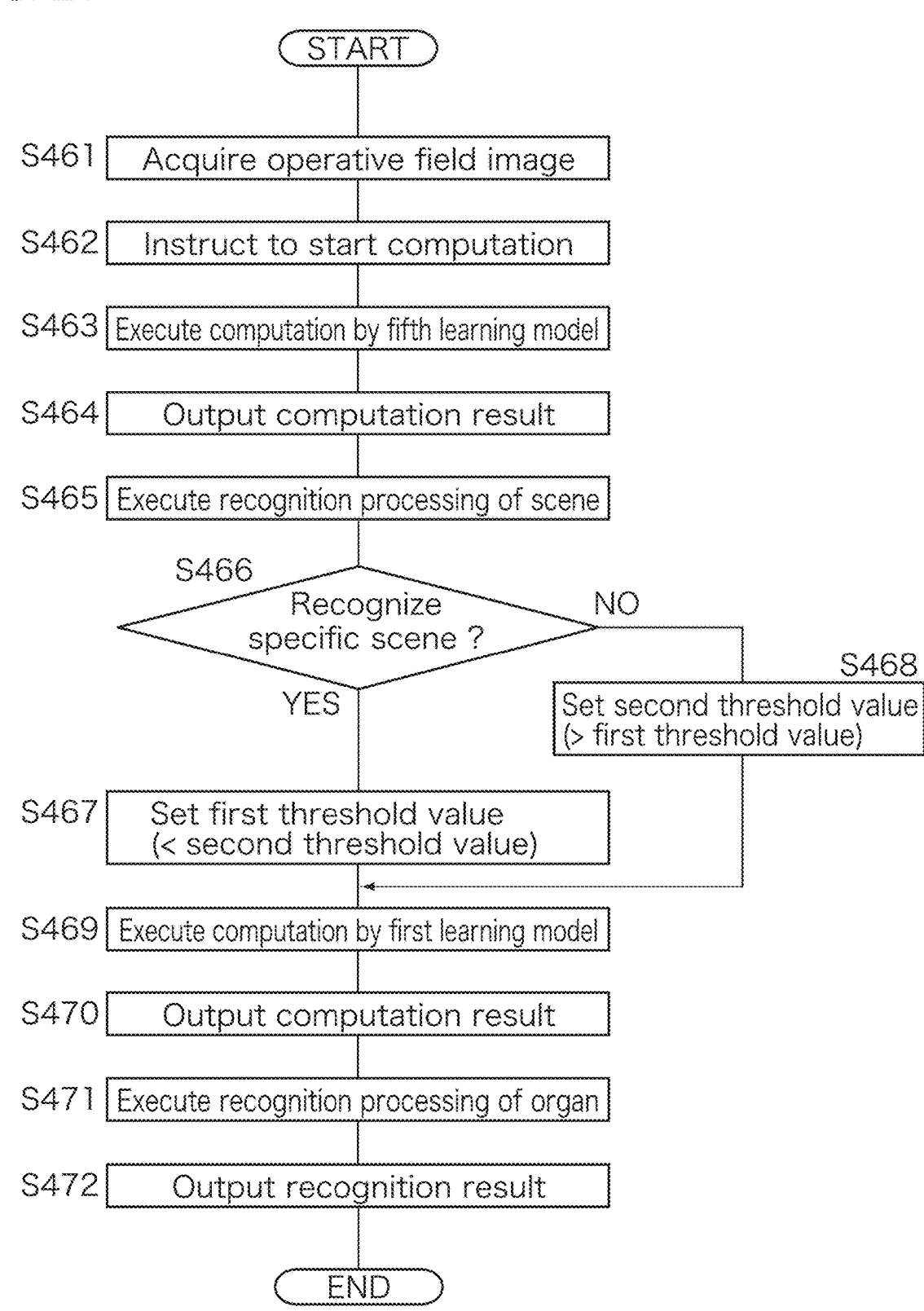
FIG. 21 is a flowchart illustrating a processing procedure in Modification Example 4-3.

The control unit 201 of the information processing device 200 may change the threshold value used in the organ recognition, in accordance with the recognized scene. FIG. 21 is a flowchart illustrating a processing procedure in Modification Example 4-3. In the same procedure as the procedure illustrated in FIG. 17, the control unit 201 of the information processing device 200 executes the scene recognition processing, each time when the operative field image is acquired (steps S461 to S465).

The control unit 201 determines whether the specific scene is recognized by the scene recognition processing (step S466). The control unit 201, for example, may determine whether it is the scene set in advance, such as the scene including the ureter and the lymph node dissection scene.

In a case where it is determined that the specific scene is recognized (S466: YES), the control unit 201 sets the threshold value used in the organ recognition to a relatively low first threshold value (<second threshold value) (step S467). That is, the control unit 201 sets the threshold value such that the organ that is the recognition target is likely to be detected. After the threshold value is set, the control unit 201 applies the computation start instruction to the first computation unit 205.

On the other hand, in a case where it is determined that the specific scene is not recognized (S466: NO), the control unit 201 sets the threshold value used in the organ recognition to a relatively high second threshold value (>first threshold value) (step S468). That is, the control unit 201 sets the threshold value such that the organ that is the recognition target is less likely to be detected. After the threshold value is set, the control unit 201 applies the computation start instruction to the second computation unit 206.

In a case where the computation start instruction is applied from the control unit 201, the first computation unit 205 executes the computation by the first learning model 310 (step S469), and outputs the computation result by the learning model 310 to the control unit 201 (step S470).

The control unit 201 executes the recognition processing of the organ, with reference to the computation result by the first learning model 310 (step S471). By comparing the probability of the label output from the softmax layer 313 of the first learning model 310 with the threshold value (the first threshold value or the second threshold value) set in step S467 or step S468, and extracting a pixel of the threshold value or more, the control unit 201 is capable of recognizing the organ included in the operative field image.

The control unit 201 outputs the recognition result of the organ (step S472). Specifically, the control unit 201 displays the recognition image of the organ to be superimposed on the operative field image by applying the instruction to the first computation unit 205. In accordance with the instruction from the control unit 201, the first computation unit 205 renders the recognition image of the organ in the built-in VRAM, and outputs the recognition image to the display device 130 through the output unit 207 to display the recognition image of the organ to be superimposed on the operative field image.

Modification Example 4-4

Figure 22:
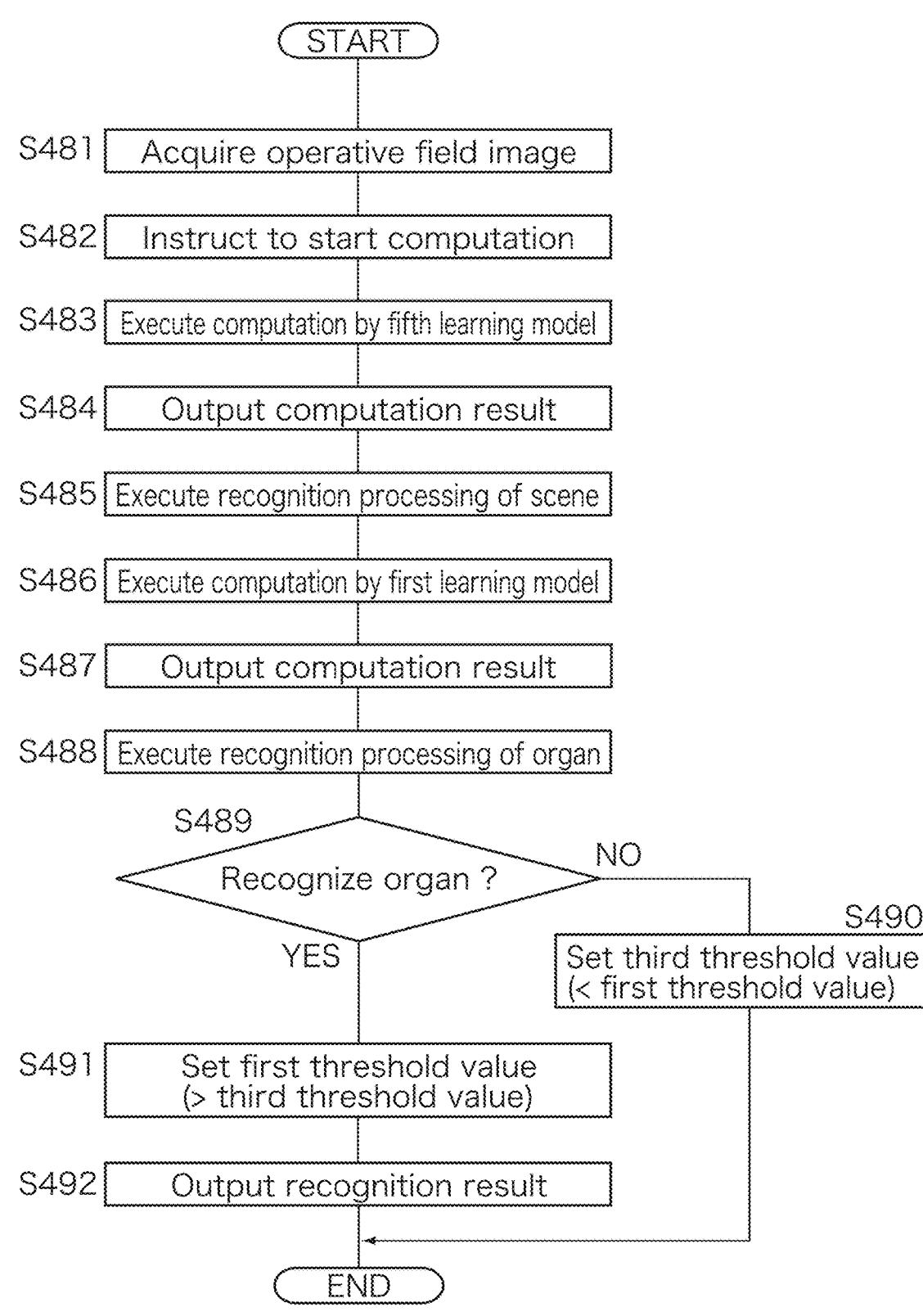
FIG. 22 is a flowchart illustrating a processing procedure in Modification Example 4-4.

The control unit 201 of the information processing device 200 may change the threshold value between a period until a target organ is recognized and a period after the target organ is recognized. FIG. 22 is a flowchart illustrating a processing procedure in Modification Example 4-4. In the same procedure as the procedure illustrated in FIG. 17, the control unit 201 of the information processing device 200 executes the scene recognition processing and the organ recognition processing, each time when the operative field image is acquired (steps S481 to S488). Note that, in the threshold value used in the organ recognition processing, a third threshold value (<First Threshold Value) is set in advance.

The control unit 201 determines whether the organ is recognized by the organ recognition processing in step S488 (step S489). For example, in a case where the number of pixels determined that the probability of the label output from the softmax layer 313 of the first learning model 310 is the third threshold value or more (for example, 30% or more) is a predetermined number or more, the control unit 201 is capable of determining that the organ is recognized from the operative field image.

In a case where it is determined that the organ is not recognized (S489: NO), the control unit 201 sets the third threshold value (step S490). That is, the control unit 201 maintains the threshold value set in advance. By maintaining the threshold value at a relatively low value until the organ is recognized, the organ is likely to be detected, and it is possible to allow the information processing device 200 to function as a sensor for organ detection.

In a case where it is determined that the organ is recognized (S489: YES), the control unit 201 sets the first threshold value higher than the third threshold value (step S491). That is, in a case where the recognition of the organ is started, the control unit 201 changes the threshold value used in the organ recognition to the first threshold value (>Third Threshold Value) from the third threshold value, and thus, is capable of improving the recognition accuracy of the organ.

The control unit 201 outputs the recognition result of the organ (step S492). Specifically, the control unit 201 displays the recognition image of the organ to be superimposed on the operative field image by applying the instruction to the first computation unit 205. In accordance with the instruction from the control unit 201, the first computation unit 205 renders the recognition image of the organ in the built-in VRAM, and outputs the recognition image of the organ in the display device 130 through the output unit 207 to display the recognition image of the organ to be superimposed on the operative field image.

Modification Example 4-5

The control unit 201 of the information processing device 200 may derive the proper name of the organ recognized by the computation result of the first learning model 310, based on information of the scene recognized by the scene recognition. FIG. 23 is a conceptual diagram illustrating an example of a proper name table. In the proper name table, the proper name of the organ that is associated with the scene of the surgery is registered. For example, in a sigmoid colon cancer surgery scene, inferior mesenteric artery or inferior mesenteric nerve plexus often appears. In the proper name table, the inferior mesenteric artery and the inferior mesenteric nerve plexus are registered as the proper name of the organ, regarding the sigmoid colon cancer surgery scene. The proper name table may be prepared in the storage unit 202 of the information processing device 200, or may be prepared in the external device.

Figure 24:
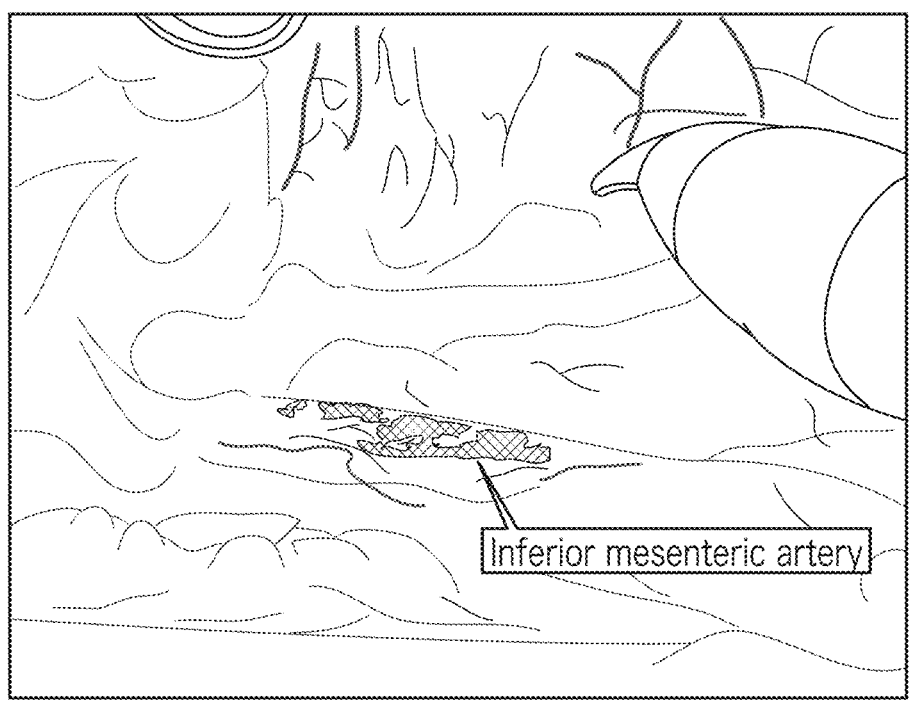
FIG. 24 is a schematic view illustrating a display example of an organ name.

In accordance with the scene recognized by the scene recognition, the control unit 201 accesses the storage unit 202 or the external device, and reads out the proper name of the organ registered in the proper name table, and thus, is capable of presenting the proper name of the organ specified by the organ recognition to the operator. FIG. 24 is a schematic view illustrating a display example of an organ name. In a case where the sigmoid colon cancer surgery scene is recognized by the scene recognition and a blood vessel is recognized by the first learning model 310 for the blood vessel recognition, the control unit 201 estimates that the blood vessel is the inferior mesenteric artery, with reference to the proper name table. The control unit 201 may display the character information indicating that the proper name of the recognized blood vessel is the inferior mesenteric artery on the display device 130. In addition, the control unit 201 may display the proper name on the display device 130 only in a case where the instruction of the operator is received through the operation unit 203 or the like.

Note that, in a case where the sigmoid colon cancer surgery scene is recognized by the scene recognition and a nerve is recognized by using the first learning model 310 for the nerve recognition, the control unit 201 may estimate the nerve as the inferior mesenteric nerve plexus, with reference to the proper name table, and may display the proper name on the display device 130.

Modification Example 4-6

The control unit 201 of the information processing device 200 may derive information of the structure, based on the information of the scene recognized by the scene recognition and the information of the organ recognized by the organ recognition. The information of the structure derived in Modification Examples 4-6 is the information of the organ recognized by the organ recognition, information of a lesion site such as a cancer or a tumor, and the like.

The control unit 201 derives the information of the structure, with reference to a structure table. FIG. 25 is a conceptual diagram illustrating an example of the structure table. In the structure table, information of a known structure for each scene is registered. The information of the structure, for example, is textbook information of the organ, and includes information such as the name, the position, and the running direction of the organ. For example, with reference to the structure table illustrated in FIG. 25, in a case where the portal is recognized in the surgery of the stomach, the control unit 201 is capable of presenting information indicating that the left gastric vein branches from the portal to the operator. Similarly, in a case where the right gastric vein is recognized in the surgery of the stomach, the control unit 201 is capable of presenting information indicating that the root of the right gastric vein is an inverted Y shape to the operator.

The structure table may be prepared for each patient. In the structure table for each patient, information of a lesion site for each patient that is obtained in advance by using another medical image or examination means is registered. For example, the information of the lesion site obtained in advance by a CT (Computed Tomography) image, an MRI (Magnetic Resonance Imaging) image, an ultrasonic tomographic image, an optical coherence tomographic image, an angiographic image, and the like is registered. In the case of using such a medical image, the information of the lesion site inside the organ that does not appear in the observation image (the operative field image) of the laparoscope 11 can be obtained. When the scene or the organ is recognized, the control unit 201 of the information processing device 200 is capable of presenting the information of the lesion site that does not appear in the operative field image, with reference to the structure table.

Figure 26A:
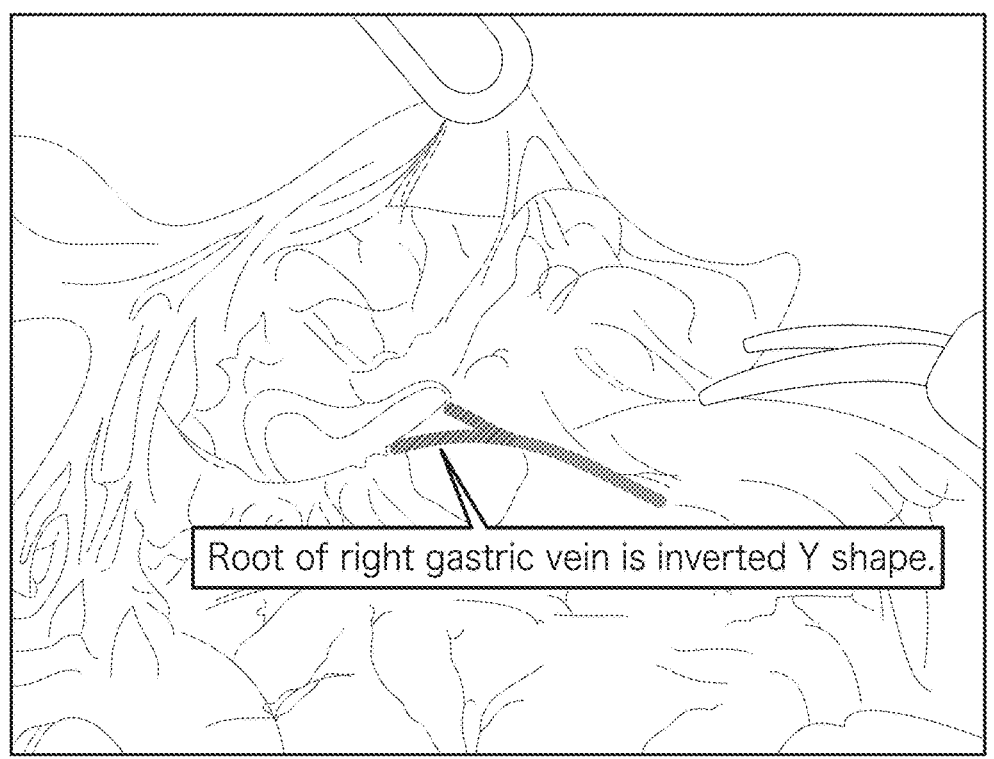
FIGS. 26A and 26B are a schematic view illustrating a display example of a structure.
Figure 26B:
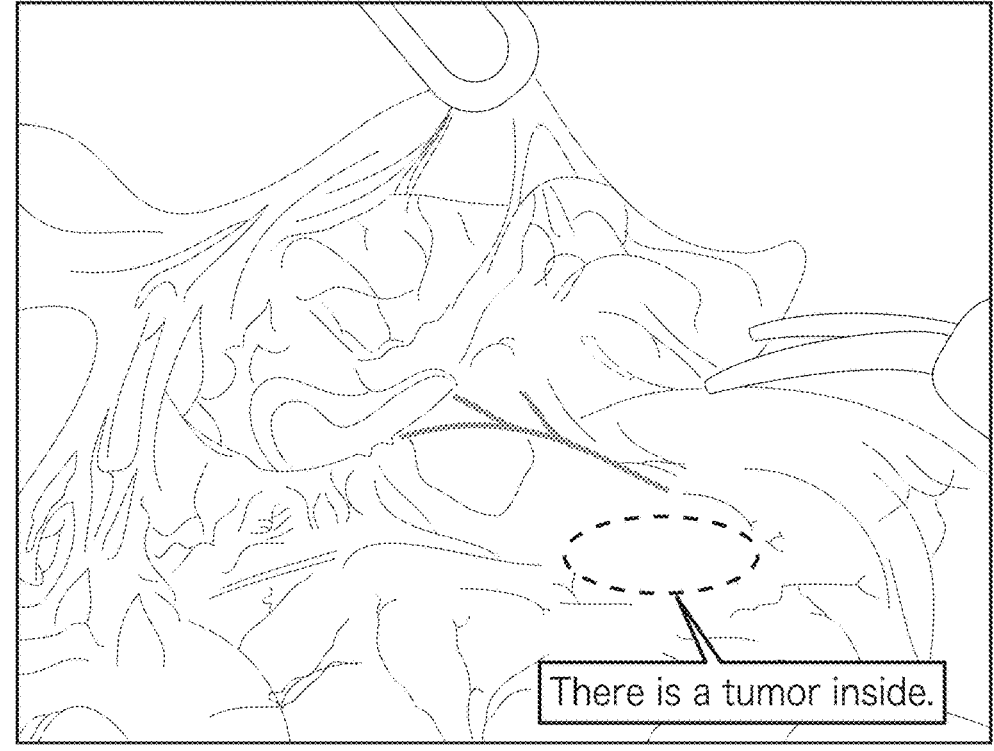

FIGS. 26A and 26B are a schematic view illustrating a display example of the structure. FIG. 26A illustrates a display example in a case where the right gastric vein is recognized in the surgery of the stomach. The control unit 201 recognizes the right gastric vein by the scene recognition or the organ recognition, and reads out the information indicating that the root of the right gastric vein is the inverted Y shape, with reference to the structure table. The control unit 201 is capable of displaying the character information indicating that the root of the right gastric vein is in the inverted Y shape or the prediction of the running of the blood vessel that has not yet been checked on the display device 130, based on the information read out from the structure table.

FIG. 26B illustrates a display example of a lesion site that does not appear in the operative field image. In a case where the information of the lesion site obtained in advance for a specific patient is registered in the structure table, and the scene and the organ are recognized, the control unit 201 reads out the information of the lesion site that does not appear in the operative field image, with reference to the structure table for each patient. The control unit 201 is capable of displaying an image of the lesion site that does not appear in the operative field image or the character information indicating that the lesion site exists inside the organ on the display device 130, based on the information read out from the structure table.

The control unit 201 may display the structure as a three-dimensional image. The control unit 201 reconstructs a plurality of tomographic images obtained in advance by CT, MRI, or the like using a method such as surface rendering or volume rendering, and thus, is capable of displaying the structure as the three-dimensional image. By superimposing the three-dimensional image on the operative field image, the control unit 201 may display the structure as an object in augmented reality (AR), or may display the structure as an object in virtual reality (VR) different from the operative field image. The object in the augmented reality or the virtual reality may be presented to the operator through a head mounted display that is not illustrated. The information processing device 200 according to this embodiment is capable of recognizing and displaying the structure such as the organ that appears in the operative field image by using the first learning model 310 or the like, and is capable of displaying the structure that does not appear in the operative field image by using an AR technology or a VR technology. The operator is capable of visually recognizing the structure such as the organ that appears in the operative field image or an internal structure that does not appear in the operative field image, and is capable of easily grasping the entire image.

Modification Example 4-7

The control unit 201 of the information processing device 200 may predict an event that may occur, based on the information of the scene recognized by the scene recognition, and the information of the organ recognized by the organ recognition. In the prediction of the event, a case table obtained by collecting cases that occurred in the past surgery is used. FIG. 27 is a conceptual diagram illustrating an example of the case table. In the case table, information of the case that occurred in the surgery is registered in association with the scene recognized by the scene recognition and the organ recognized by the organ recognition. The table in FIG. 27 illustrates an example in which a plurality of cases of bleeding from the inferior mesenteric artery in the sigmoid colon cancer surgery scene are registered.

Figure 28:
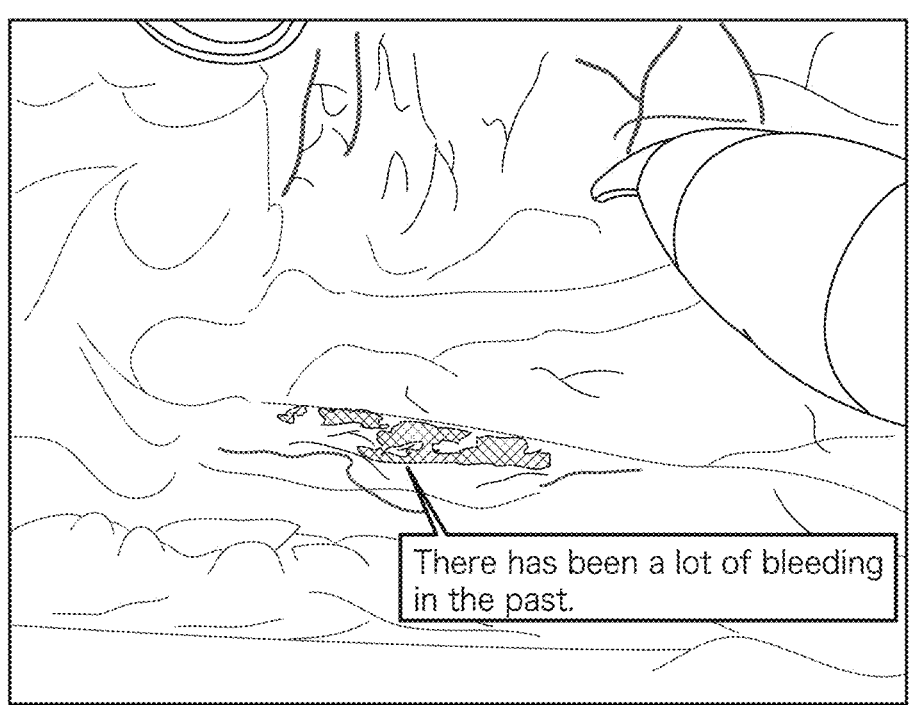
FIG. 28 is a schematic view illustrating a display example of an event.

FIG. 28 is a schematic view illustrating a display example of the event. In a case where the sigmoid colon cancer surgery scene is recognized by the scene recognition, and the inferior mesenteric artery is recognized by the organ recognition, the control unit 201 is capable of grasping that the bleeding occurred frequently in the past, with reference to the case table, and thus, is capable of displaying the effect on the display device 130 as the character information. Note that, the control unit 201 may display not only the case that occurred in the past, but also a special case that occurred in the past or a case to be reported to the operator on the display device 130 as the preliminary information.

As described above, in Embodiment 4, it is possible to derive the integrative recognition result regarding the operative field image, based on the computation result obtained from the first learning model 310 for the organ recognition and the computation result obtained from the fifth learning model 350 for the scene recognition, and to provide the information based on the derived recognition result to the operator.

Embodiment 5

In Embodiment 5, a configuration will be described in which the integrative recognition result is derived by combining the event recognition with the scene recognition.

The information processing device 200 according to Embodiment 5 derives information of the characteristic scene in the event, in accordance with the recognition result of the event. As a specific example, a configuration will be described in which when the information processing device 200 recognizes the organ damage as an event, a damage occurrence scene and a damage restoration scene are derived as the characteristic scene. The information processing device 200 includes the third learning model 330 trained to output information relevant to the organ damage, in accordance with the input of the operative field image, and the fifth learning model 350 trained to output information relevant to the damage occurrence scene and the damage restoration scene, in accordance with the input of the operative field image. The information processing device 200 executes the computation by the third learning model 330 in the first computation unit 205, and executes the computation by the fifth learning model 350 in the second computation unit 206, each time when the operative field image is acquired. In addition, the information processing device 200 transitorily records the operative field image (video) input by the input unit 204 in the storage unit 202.

Figure 29:
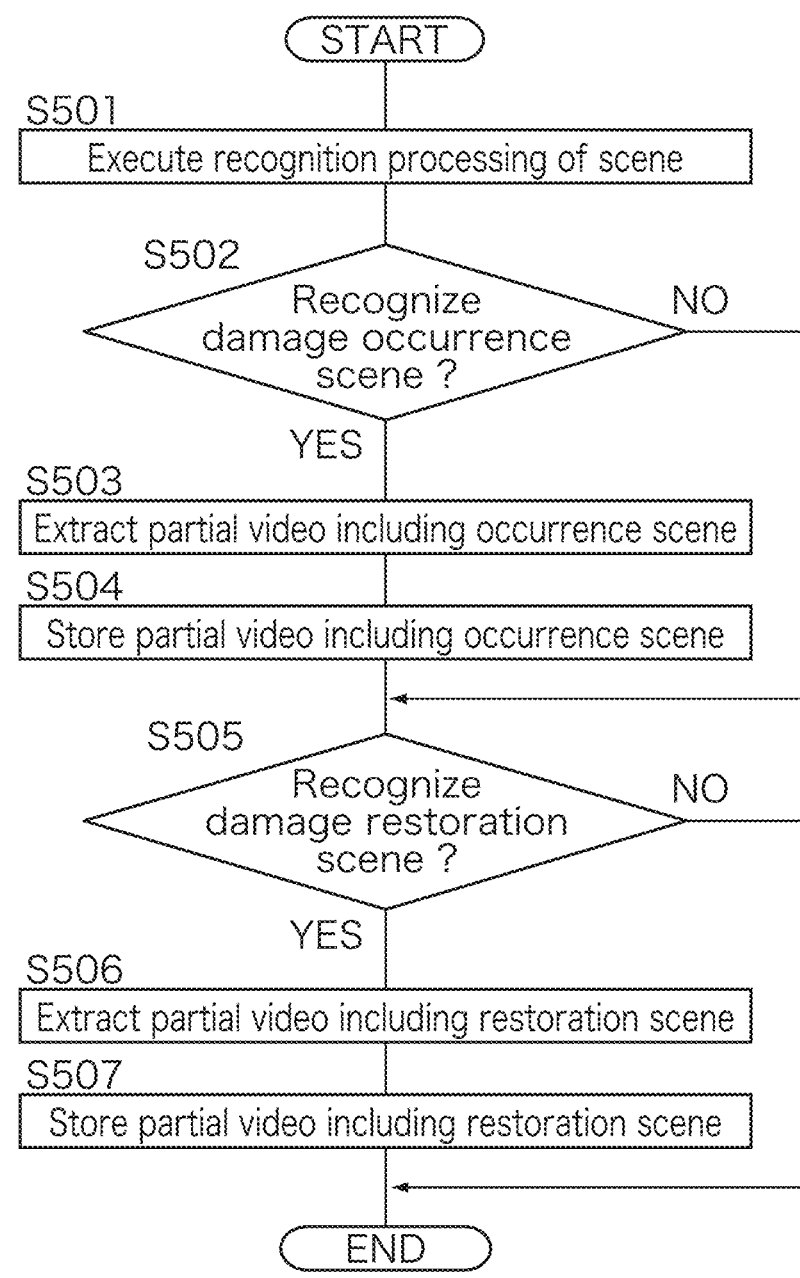
FIG. 29 is a flowchart illustrating a procedure of processing executed by an information processing device according to Embodiment 5.

FIG. 29 is a flowchart illustrating the procedure of the processing executed by the information processing device 200 according to Embodiment 5. The control unit 201 executes the recognition processing of the event (the organ damage) with reference to the computation result by the third learning model 330, each time when the operative field image is acquired, and determines whether there is the organ damage, based on the recognition result. In a case where it is determined that there is an organ damage, the control unit 201 executes the following processing.

The control unit 201 executes the scene recognition processing with reference to the computation result by the fifth learning model 350, each time when the operative field image is acquired (step S501), and determines whether the damage occurrence scene is recognized based on an execution result of the scene recognition processing (step S502). In a case where the scene of the previous frame is compared with the scene of the current frame, and a scene in which the organ is not damaged is switched to a scene in which the organ is damaged, the control unit 201 determines that the damage occurrence scene is recognized. In a case where it is determined that the damage occurrence scene is not recognized (S502: NO), the control unit 201 allows the processing to proceed to step S505.

In a case where it is determined that the damage occurrence scene is recognized (S502: YES), the control unit 201 extracts a partial video including the occurrence scene (step S503). The control unit 201, for example, designates a time point before a damage occurrence time point (for example, a time point before a few seconds) as a start point of the partial video, and the damage occurrence time point as an end point of the partial video, for the operative field image (video) transitorily recorded in the storage unit 202, and thus, extracts the partial video including the occurrence scene. Alternatively, the control unit 201 may further record the operative field image (video), and may designate the time point before the damage occurrence time point as the start point of the partial video, and a time point after the damage occurrence (for example, a time point after a few seconds) as the end point of the partial video, and thus, may extract the partial video including the occurrence scene.

The control unit 201 stores the extracted partial video in the storage unit 202 (step S504). The control unit 201 cuts out the partial video between the start point and the end point designated in step S503 from the video recording video, and separately stores the partial video in the storage unit 202 as a moving image file.

The control unit 201 determines whether the damage restoration scene is recognized based on the execution result of the scene recognition processing in step S501 (step S505). In a case where the scene of the previous frame is compared with the scene of the current frame, and the scene in which the organ is damaged is switched to the scene in which the organ is not damaged, the control unit 201 determines that the damage restoration scene is recognized. In a case where it is determined that the damage restoration scene is not recognized (S505: NO), the control unit 201 ends the processing according to this flowchart.

In a case where it is determined that the damage restoration scene is recognized (S505: YES), the control unit 201 extracts a partial video including the restoration scene (step S506). The control unit 201, for example, designates a time point before a restoration time point (for example, a time point before a few seconds) as the start point of the partial video, and the restoration time point as the end point of the partial video, for the operative field image (video) transitorily recorded in the storage unit 202, and thus, extracts the partial video including the restoration scene. Alternatively, the control unit 201 may further record the operative field image (video), and may designate the time point before the restoration time point as the start point of the partial video, and a time point after the restoration (for example, a time point after a few seconds) as the end point of the partial video, and thus, may extract the partial video including the restoration scene.

The control unit 201 stores the extracted partial video in the storage unit 202 (step S507). The control unit 201 curs out the partial video between the start point and the end point designated in step S506 from the video recording video, and separately stores the partial video in the storage unit 202 as a moving image file.

The control unit 201 registers information of the recognized scene in a scene recording table, each time when the scene is recognized. The scene recording table is prepared in the storage unit 202. FIG. 30 is a conceptual diagram illustrating an example of the scene recording table. In the scene recording table, for example, a date and time when the scene is recognized, a name for identifying the recognized scene, and the moving image file of the partial video extracted when the scene is recognized are stored in association with each other. The example of FIG. 30 illustrates a state in which the moving image file indicating the damage occurrence scene and the moving image file indicating the damage restoration scene are registered in the scene recording table, in association with the date and time, regarding the damage occurrence scene and the restoration scene recognized from the start to the end of the surgery.

The control unit 201 may display information of the scene registered in the scene recording table on the display device 130. The control unit 201, for example, may display the information of the scene on the display device 130 in a table format such that the operator or the like is capable of selecting any scene. Alternatively, the control unit 201 may arrange an object (UI) such as a thumbnail and an icon indicating each scene on the display screen, and may receive the selection of the scene by the operator or the like. In a case where the selection of the scene by the operator or the like is received, the control unit 201 reads out the moving image file of the corresponding scene from the storage unit 202, and playbacks the read moving image file. The moving image file is displayed on the display device 130.

In addition, the control unit 201 may be configured to playback the moving image file of the selected scene. In a case where the damage occurrence scene is registered, but the restoration scene with respect to the damage is not registered, with reference to the scene recording table, the control unit 201 may playback the damage occurrence scene to report the effect that the restoration is not performed to the operator.

In this embodiment, the damage occurrence scene and the restoration scene are recognized, and the partial video is extracted for each of the recognized scenes and is stored in the storage unit 202 as the moving image file, but the scene to be recognized is not limited to the damage occurrence scene and the restoration scene. Regarding various events that may occur during the surgery, the control unit 201 may recognize the characteristic scene in the event, may extract the partial video of the recognized characteristic scene, and may store the partial video in the storage unit 202 as the moving image file.

For example, the control unit 201 may recognize a bleeding occurrence scene and a hemostasis scene, in accordance with the recognition of a bleeding event, may extract the partial video for each of the recognized scenes, and may store the partial image in the storage unit 202 as the moving image file. In addition, in a case where the bleeding event is recognized, the control unit 201 may recognize a scene in which an artifact such as gauze is framed in the operative field image and a scene in which the artifact is framed out from the operative field image, may extract the partial video for each of the recognized scenes, and may store the partial video in the storage unit 202 as the moving image file. Note that, the introduction of the gauze into the body of the patient is not limited to the case of bleeding, and thus, in a case where the scene in which the gauze is framed in the operative field image and the scene in which the gauze is framed out from the operative field image are recognized during the surgery, regardless of the recognition of the bleeding event, the control unit 201 may extract the partial video for each of the scenes, and may store the partial video in the storage unit 202 as the moving image file. In addition, the control unit 201 may recognize the scene in which the artifact such as not only the gauze but also a hemostasis clip, a restraint band, and a suture needle is framed in the operative field image and the scene in which the artifact is framed out from the operative field image, and may store the moving image file corresponding to the partial video of such a scene in the storage unit 202.

As described above, in Embodiment 5, the partial video (the moving image file) indicating the characteristic scene is stored in the storage unit 202, regarding the event that occurs during the surgery, and thus, it is possible to easily review the event.

Embodiment 6

The control unit 201 of the information processing device 200 may allow both of the first computation unit 205 and the second computation unit 206 to execute the computation by the first learning model 310 for the same operative field image, and may evaluate the computation result by the first computation unit 205 and the computation result by the second computation unit 206, and thus, may derive error information in the first computation unit 205 or the second computation unit 206.

Figure 31:
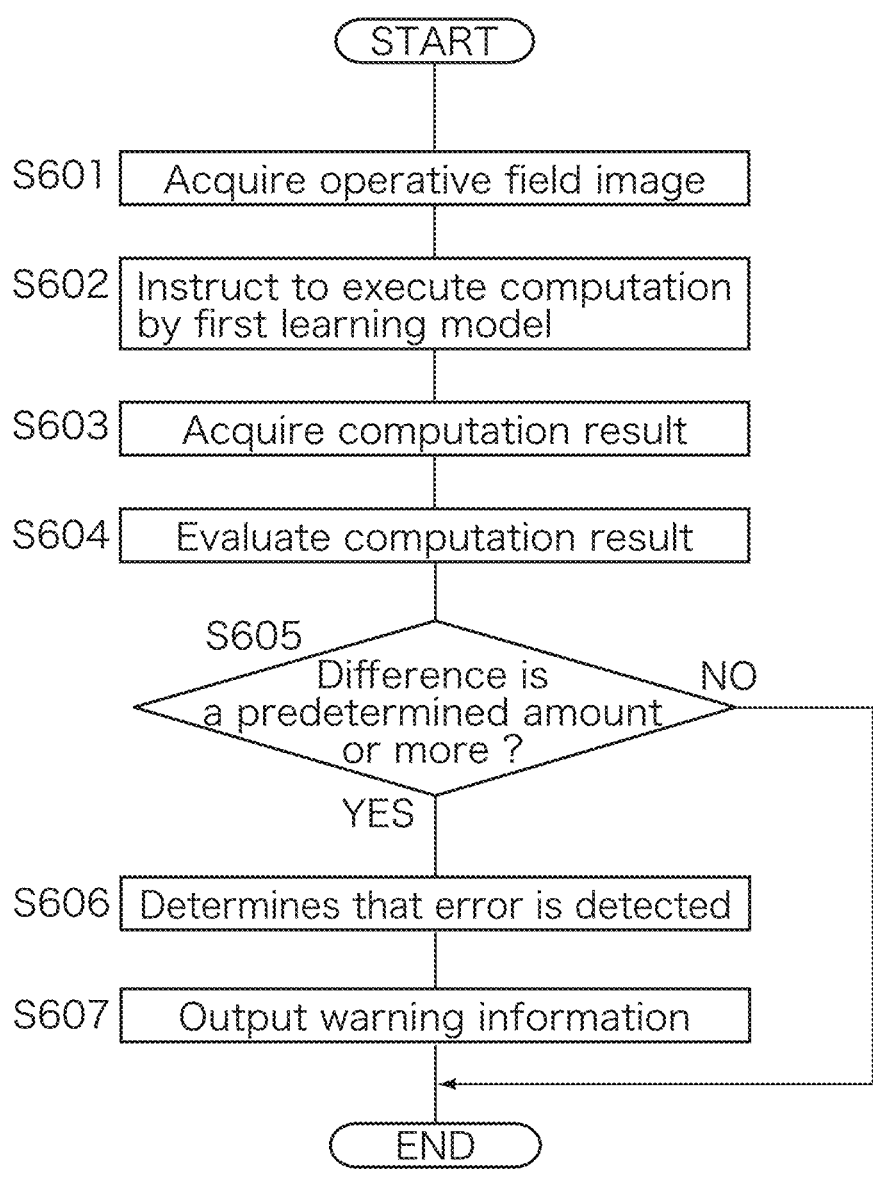
FIG. 31 is a flowchart illustrating a procedure of processing executed by an information processing device according to Embodiment 6.

FIG. 31 is a flowchart illustrating the procedure of the processing executed by the information processing device 200 according to Embodiment 6. In a case where the operative field image is acquired (step S601), the control unit 201 allows both of the first computation unit 205 and the second computation unit 206 to execute the computation by the first learning model 310 (step S602).

The control unit 201 acquires the computation result of the first computation unit 205 and the computation result of the second computation unit 206 (step S603), and evaluates the computation result (step S604). The control unit 201 determines whether a difference between the computation result by the first computation unit 205 and the computation result by the second computation unit 206 is a predetermined amount or more (step S605). In a case where the difference is less than the predetermined amount (S605: NO), the control unit 201 ends the processing according to this flowchart. In a case where it is determined that the difference is the predetermined amount or more (S605: YES), the control unit 201 determines that an error is detected (step S606), and outputs the warning information (step S607). The warning information may be displayed on the display device 130, or may be output by a sound or a voice.

Embodiment 7

In Embodiment 7, a configuration will be described in which the usage state of the surgical tool is estimated by combining recognition results by a plurality of learning models.

The information processing device 200 according to Embodiment 7 includes the first learning model 310 for recognizing the organ, the fourth learning model 340 for recognizing the device, and the fifth learning model 350 for recognizing the scene.

The first learning model 310 is a learning model trained to output a probability indicating whether each pixel configuring the operative field image corresponds to the organ that is the recognition target, in accordance with the input of the operative field image. The control unit 201 of the information processing device 200 continually acquires the computation result from the first learning model 310, and analyzes the computation result on a time-series basis to estimate the influence of the surgical tool on the organ. For example, the control unit 201 calculates a change in a pixel number or an area recognized as the organ by the first learning model 310, the amount of loss of the pixels recognized as the organ, or the like, and in a case where it is determined that a predetermined amount of pixels is lost, estimates that the surgical tool is moved on the organ.

The fourth learning model 340 is a learning model trained to output information relevant to a device that appears in the operative field image, in accordance with the input of the operative field image. The fourth learning model 340 in Embodiment 7 is trained to include information according to an opening and closing state of the forceps 13, as the information relevant to the device.

In a case where the operative field image is input, the fifth learning model 350 is a learning model trained to output information relevant to a scene indicated by the operative field. The fifth learning model 350 in Embodiment 7 is trained to include information of a scene in which the organ is grasped, as the information relevant to the scene.

Figure 32:
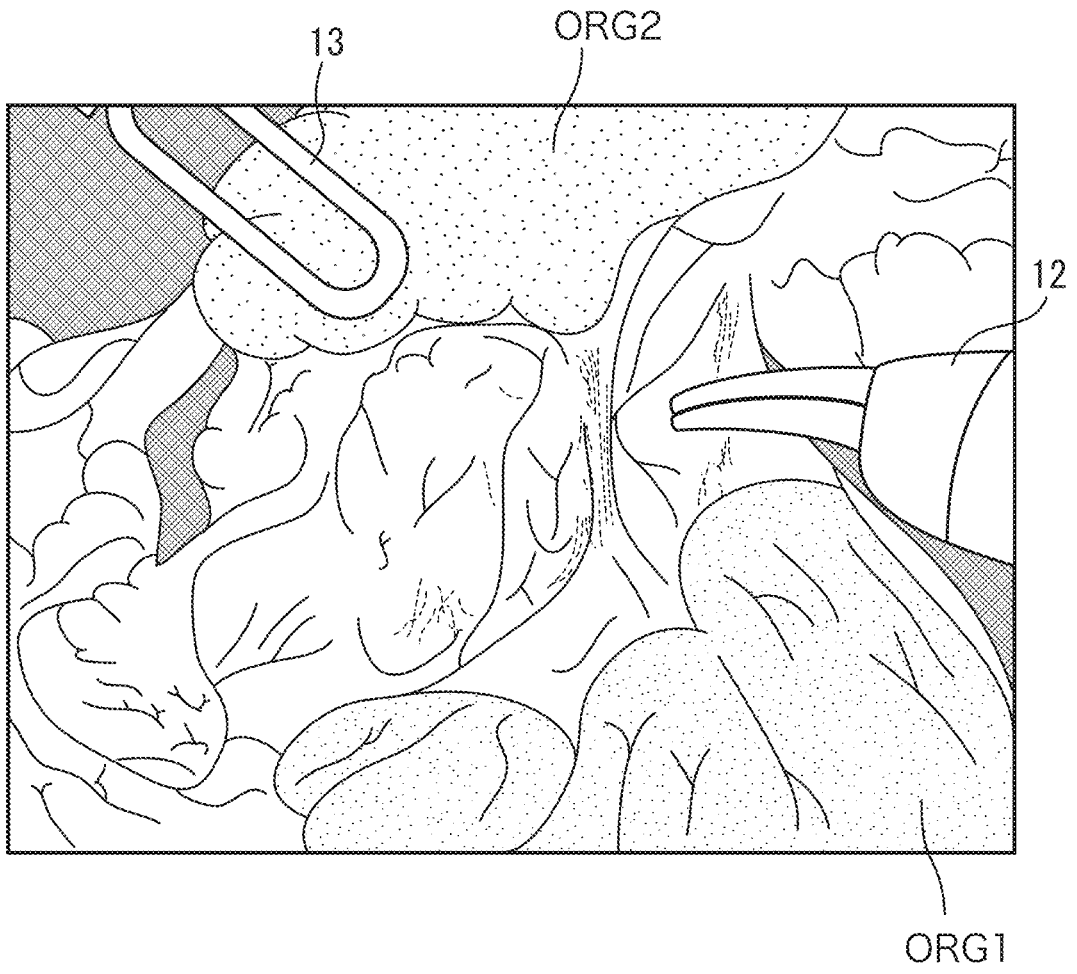
FIG. 32 is an explanatory diagram illustrating an estimation method in Embodiment 7.

FIG. 32 is an explanatory diagram illustrating an estimation method in Embodiment 7. The operative field image illustrated in FIG. 32 illustrates a scene in which a connective tissue filling between a tissue ORG1 configuring an organ and a tissue ORG2 including a lesion site such as a malignant tumor is excised. In this case, the operator grasps the tissue ORG2 including the lesion site with the forceps 13, and expands the tissue in a suitable direction to expose the connective tissue existing between the tissue ORG2 including the lesion site and the tissue ORG1 to remain. The operator excises the exposed connective tissue by using the energy treatment tool 12 to peel off the tissue ORG2 including the lesion site from the tissue ORG1 to be remained.

The control unit 201 of the information processing device 200 acquires computation result obtained by inputting the operative field image as illustrated in FIG. 32 to the fourth learning model 340, and recognizes that the forceps 13 are closed. However, it is not possible for the control unit 201 to grasp whether the forceps 13 are closed in the state of grasping the organ or the forceps 13 are closed without grasping the organ, only by the computation result of the fourth learning model 340.

Therefore, in Embodiment 7, the usage state of the forceps 13 is estimated by further combining the computation results of the first learning model 310 and the fifth learning model 350. That is, in a case where the control unit 201 recognizes that the forceps 13 are closed by the computation result of the fourth learning model 340, recognizes that the forceps 13 exist on the organ by the computation result of the first learning model 310, and recognizes that it is a scene in which the organ is grasped by the computation result of the fifth learning model 350, it is possible to recognize that the forceps 13 are closed in the state of grasping the organ.

Figure 33:
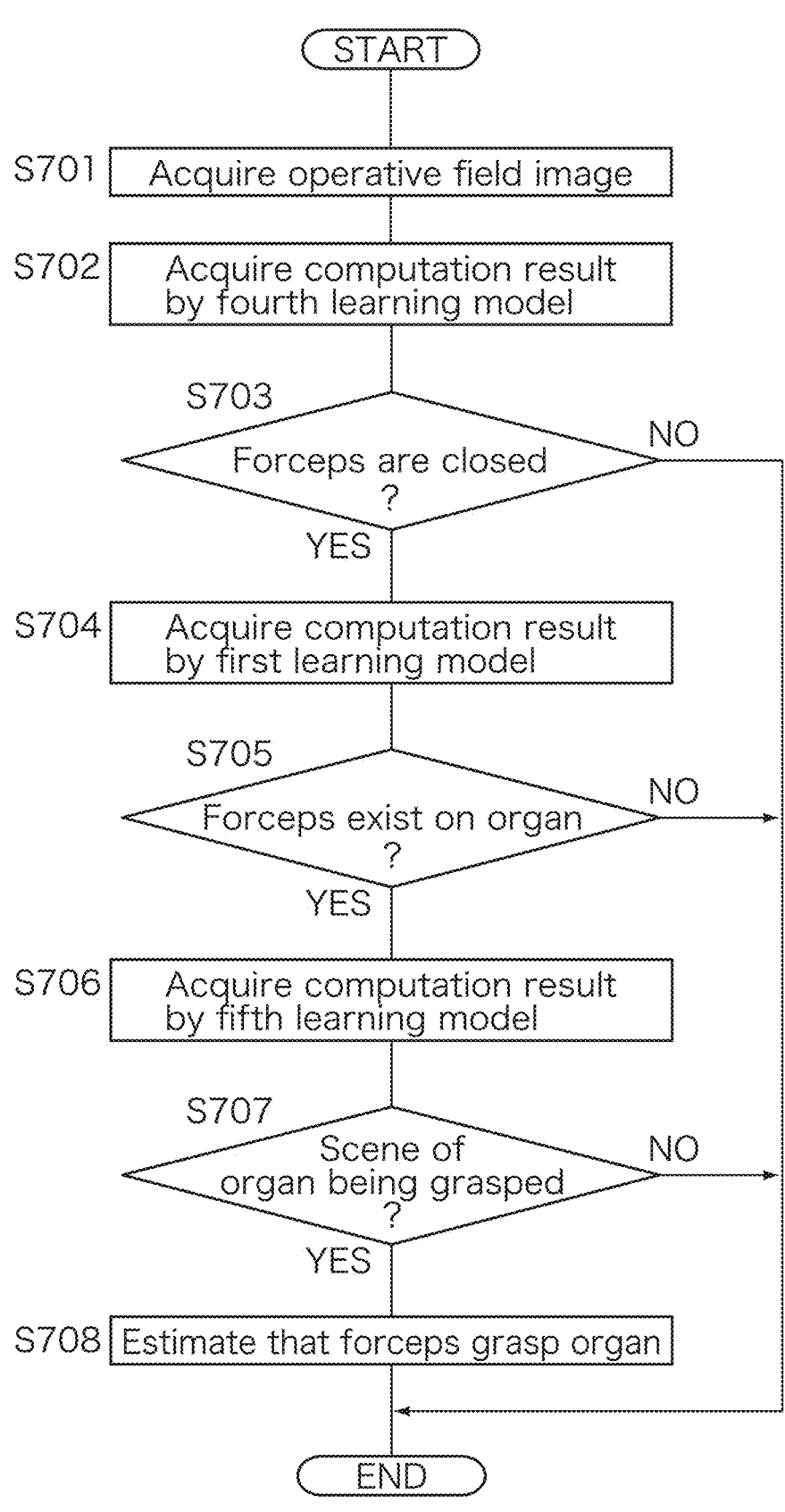
FIG. 33 is a flowchart illustrating an estimation procedure in Embodiment 7.

FIG. 33 is a flowchart illustrating an estimation procedure in Embodiment 7. The control unit 201 of the information processing device 200 acquires the operative field image in the frame unit that is output from the CCU 110 by the input unit 204 (step S701). The control unit 201 executes the following processing, each time when the operative field image in the frame unit is acquired.

The control unit 201 acquires the computation result by the fourth learning model 340 (step S702), and determines whether the forceps 13 are closed (step S703). The computation by the fourth learning model 340, for example, is executed by the second computation unit 206. The control unit 201 may acquire the computation result by the fourth learning model 340 from the second computation unit 206. In a case where it is determined that the forceps 13 are not closed (S703: NO), the control unit 201 ends the processing according to this flowchart.

In a case where it is determined that the forceps 13 are closed (S703: YES), the control unit 201 acquires the computation result by the first learning model 310 (step S704), and determines whether the forceps 13 exist on the organ (step S705). The computation by the first learning model 310, for example, is executed by the first computation unit 205. The control unit 201 may acquire the computation result by the first learning model 310 from the first computation unit 205. In a case where it is determined that the forceps 13 do not exist on the organ (S705: NO), the control unit 201 ends the processing according to this flowchart.

In a case where it is determined that the forceps 13 exist on the organ (S705: YES), the control unit 201 acquires the computation result by the fifth learning model 350 (step S706), and determines whether it is the scene in which the organ is grasped (step S707). The computation by the fifth learning model 350, for example, is executed by the second computation unit 206 while the computation by the fourth learning model 340 is not executed. The control unit 201 may acquire the computation result by the fifth learning model 350 from the second computation unit 206. In a case where it is determined that it is not the scene in which the organ is grasped (S707: NO), the control unit 201 ends the processing according to this flowchart.

In a case where it is determined that it is the scene in which the organ is grasped (step S707: YES), the control unit 201 estimates that the forceps grasp the organ (step S708). An estimation result may be displayed on the operative field image. For example, display such as making the color of the forceps 13 bright may be performed at a timing when the grasping of the organ by the forceps 13 is completed.

In this embodiment, a configuration has been described in which the state of grasping the organ with the forceps 13 is estimated, but by combining the recognition results of the plurality of learning models, it is possible to estimate the grasping by the forceps 13, but also treatments (grasping, interruption, peeling, or the like) using various surgery devices.

Embodiment 8

In Embodiment 8, a configuration will be described in which the optimal learning model is selected in accordance with the operative field image to be input.

The information processing device 200 according to Embodiment 8 includes a plurality of learning models for recognizing the same recognition target. As an example, a configuration will be described in which the same organ is recognized by using the first learning model 310 and the second learning model 320. The organ recognized by the first learning model 310 and the second learning model 320 is not limited to the loose connective tissue or the nerve tissue, and may be an organ set in advance.

In an example, the first learning model 310 and the second learning model 320 are constructed by using different neural networks. For example, the first learning model 310 is constructed by SegNet, and the second learning model 320 is constructed by U-Net. The combination of the neural networks constructing the first learning model 310 and the second learning model 320 is not limited to the above, and any neural network may be used.

Alternatively, the first learning model 310 and the second learning model 320 may be learning models having different internal configurations. For example, the first learning model 310 and the second learning model 320 are learning models constructed by using the same neural network, and may be learning models having different types of layers, different numbers of layers, different numbers of nodes, different connection relationships in the nodes, or the like.

In addition, the first learning model 310 and the second learning model 320 may be learning models trained by using different training data pieces. For example, the first learning model 310 may be a learning model trained by using training data including ground truth data annotated by a first specialist, and the second learning model 320 may be a learning model trained by using training data including ground truth data annotated by a second specialist different from the first specialist. In addition, the first learning model 310 may be a learning model trained by using training data including an operative field image imaged in a certain health institute and annotation data (ground truth data) with respect to the operative field image, and the second learning model 320 may be a learning model trained by using training data including an operative field image imaged in another health institute and annotation data (ground truth data) with respect to the operative field image.

In a case where the operative field image is input, the information processing device 200 executes the computation of the first learning model 310 by the first computation unit 205, and executes the computation of the second learning model 320 by the second computation unit 206. The control unit 201 of the information processing device 200 analyzes the computation result by the first computation unit 205 and the computation result by the second computation unit 206, and selects a learning model optimal for the organ recognition, based on an analysis result (in this embodiment, either the first learning model 310 or the second learning model).

Figures 34A, 34B, 34C:
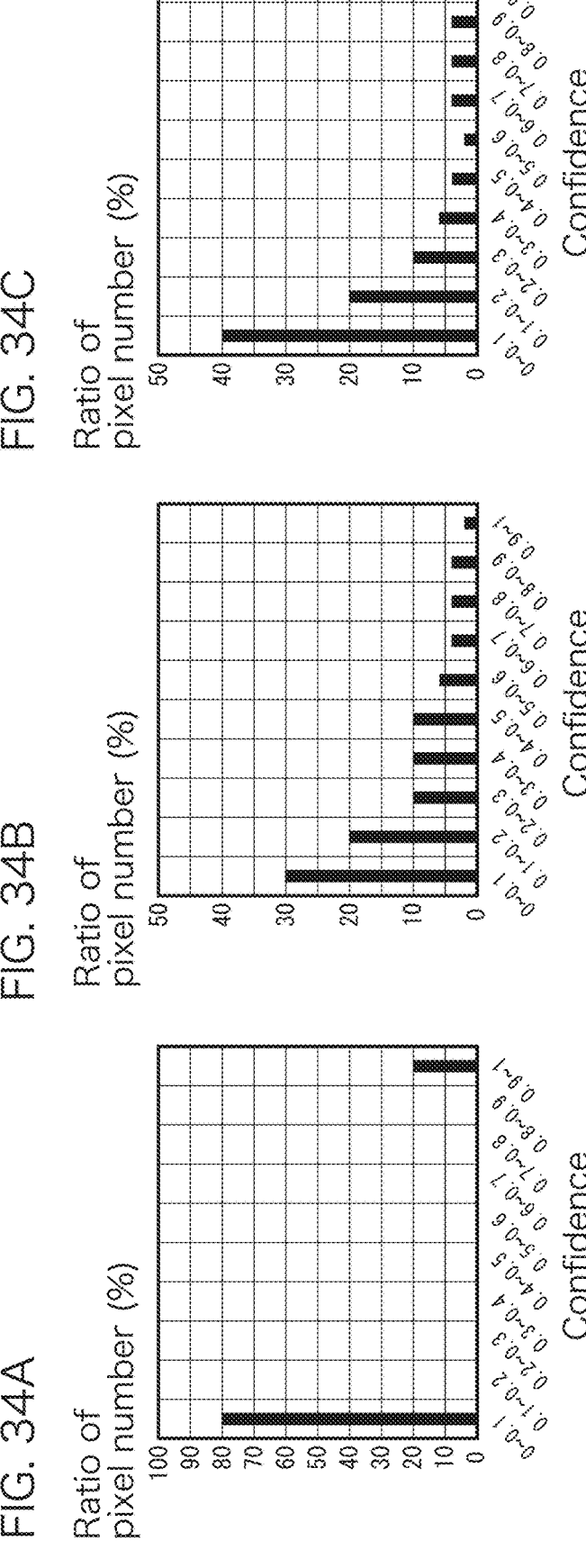
FIGS. 34A to 34C are an explanatory diagram illustrating an analysis method of a computation result.

FIGS. 34A to 34C are an explanatory diagram illustrating an analysis method of the computation result. A probability (a confidence) indicating whether each pixel corresponds to the organ that is the recognition target is output from each of the learning models for recognizing the organ, as each of the computation results. In a case where the pixel number is added up for each confidence, for example, a distribution as illustrated in FIGS. 34A to 34C is obtained. In each graph illustrated in FIGS. 34A to 34C, a horizontal axis indicates the confidence, and a vertical axis indicates the pixel number (a ratio to the entire image). Ideally, each pixel is classified into a case where the confidence is 1 (a probability that it is the organ is 100%) or a case where the confidence is 0 (the probability that it is the organ is 0), and thus, in a case where the distribution of the confidence is examined based on the computation result obtained from an ideal learning model, a polarized distribution as illustrated in FIG. 34A is obtained.

In a case where the computation result is acquired from the first learning model 310 and the second learning model 320, the control unit 201 of the information processing device 200 adds up the pixel number for each confidence, and selects a learning model having a distribution close to the ideal distribution. For example, in a case where the distribution obtained from the computation result of the first learning model 310 is a distribution illustrated in FIG. 34B, and the distribution obtained from the computation result of the second learning model 320 is a distribution illustrated in FIG. 34C, the latter case is close to the ideal distribution, and thus, the control unit 201 selects the second learning model 320.

The control unit 201, for example, evaluates each distribution by using an evaluation coefficient in which an evaluation value increases as the confidence approaches 1 or 0 to determine whether the distribution is close to the ideal distribution. FIG. 35 is a diagram illustrating an example of an evaluation coefficient table. Such an evaluation coefficient table is prepared in advance in the storage unit 202. In the example of FIG. 35, the evaluation coefficient is set to have a higher value as the confidence approaches 1 or 0.

In a case where a result of adding up the pixel number for each confidence is obtained, the control unit 201 calculates a score indicating the quality of the distribution by multiplying the result and the evaluation coefficient together. FIGS. 36A to 36C are a diagram illustrating an example of a score calculation result. FIGS. 36A to 36C illustrate a result of calculating the score for each of the distributions illustrated in FIGS. 34A to 34C. A score calculated from the ideal distribution is the highest score. In the case of calculating the score for the distribution obtained from the computation result of the first learning model 310, the total score is 84, and in the case of calculating the score for the distribution obtained from the computation result of the second learning model 320, the total score is 188. That is, since the second learning model 320 has a higher score than the first learning model 310, the control unit 201 selects the second learning model 320, as a suitable learning model.

Figure 37:
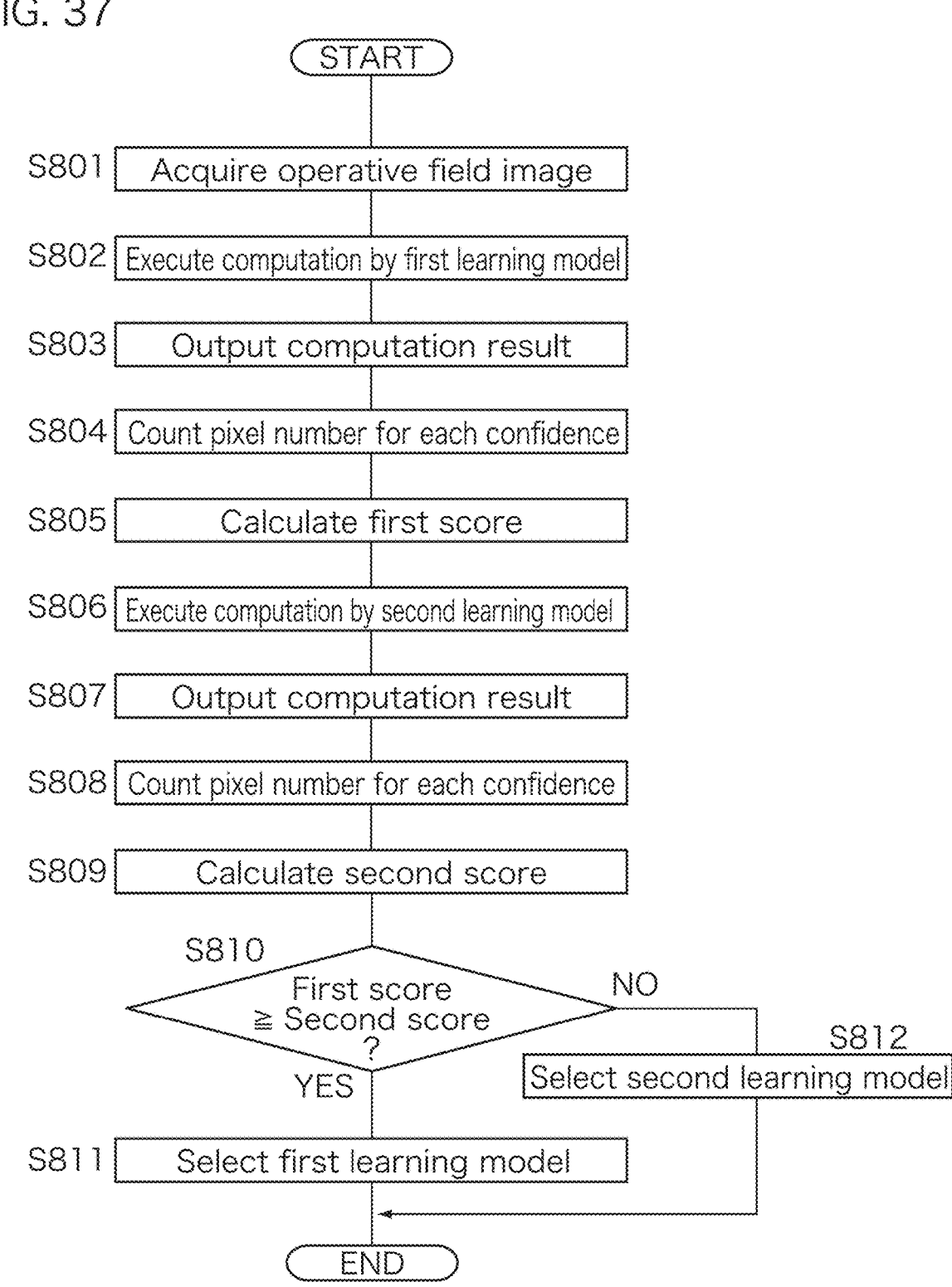
FIG. 37 is a flowchart illustrating a procedure of processing executed by an information processing device according to Embodiment 8.

FIG. 37 is a flowchart illustrating the procedure of the processing executed by the information processing device 200 according to Embodiment 8. In a case where the operative field image is acquired (step S801), the control unit 201 allows the first computation unit 205 to execute the computation by the first learning model 310 (step S802), and acquires the computation result by the first learning model 310 (step S803). The control unit 201 counts the pixel number for each confidence, with respect to the first learning model 310 (step S804), and calculates the score (a first score) of the distribution by multiplying each of the added pixel numbers and the evaluation coefficient together (step S805).

Similarly, the control unit 201 allows the second computation unit 206 to execute the computation by the second learning model 320 for the operative field image acquired in step S801 (step S806), and acquires the computation result by the second learning model 320 (step S807). The control unit 201 counts the pixel number for each confidence, with respect to the second learning model 320 (step S808), and calculates the score (a second score) of the distribution by multiplying each of the added pixel numbers and the evaluation coefficient together (step S809).

In this flowchart, for convenience, the computation (S802 to S805) for the first learning model 310 is executed, and then, the computation (S806 to S809) for the second learning model 320 is executed, but such a procedure may be reversed, or may be executed in a simultaneous and parallel manner.

The control unit 201 compares the first score with the second score, and determines whether the first score is greater than or equal to the second score (step S810).

In a case where it is determined that the first score is greater than or equal to the second score (S810: YES), the control unit 201 selects the first learning model 310, as a suitable learning model (step S811). Thereafter, the control unit 201 executes the organ recognition processing by using the selected first learning model 310.

In a case where it is determined that the first score is less than the second score (S810: NO), the control unit 201 selects the second learning model 320, as a suitable learning model (step S812). Thereafter, the control unit 201 executes the organ recognition processing by using the selected second learning model 320.

As described above, in Embodiment 8, it is possible to execute the organ recognition processing by selecting a more suitable learning model.

The information processing device 200 may execute the organ recognition processing using the computation result of the first learning model 310 in the foreground, and may execute the computation by the second learning model 320 in the background. The control unit 201 may evaluate the first learning model 310 and the second learning model 320 at a periodic timing, and may switch the learning model used in the organ recognition, in accordance with the evaluation result. In addition, the control unit 201 may evaluate the first learning model 310 and second learning model 320 at a timing when the instruction is applied from the operator or the like, and may switch the learning model used in the organ recognition, in accordance with the evaluation result. Further, in a case where the characteristic scene is recognized in combination with the scene recognition described in Embodiment 4, the first learning model 310 and the second learning model 320 may be evaluated, and the learning model used in the organ recognition may be switched, in accordance with the evaluation result.

In Embodiment 8, an application example for the learning models 310 and 320 for the organ recognition has been described, but a default model and an optional model may be also prepared for the learning model 330 for the event recognition, the learning model 340 for the device recognition, and the learning model 350 for the scene recognition, the computation results may be evaluated, and the model used in the recognition may be switched.

In Embodiment 8, a method using the evaluation coefficient has been described as an evaluation method of the first learning model 310 and the second learning model 320, but the evaluation method is not limited to the method using the evaluation coefficient, and the evaluation can be performed by using various statistical indices. For example, the control unit 201 may obtain a dispersion or a standard deviation regarding the distribution, and in a case where the dispersion or the standard deviation is high, may determine that the distribution is polarized. In addition, the control unit 201 may evaluate the computation result of each model by taking the value of a 100-pixel ratio (%) as the value of a vertical axis of a graph, and obtaining the peakedness or the skewness of the graph. Further, the control unit 201 may evaluate the computation result of each model by using a mode value, a percentile, or the like.

Embodiment 9

In Embodiment 9, a configuration will be described in which the organ recognition is performed in the foreground, and the recognition of the bleeding event is performed in the background.

Figure 38:
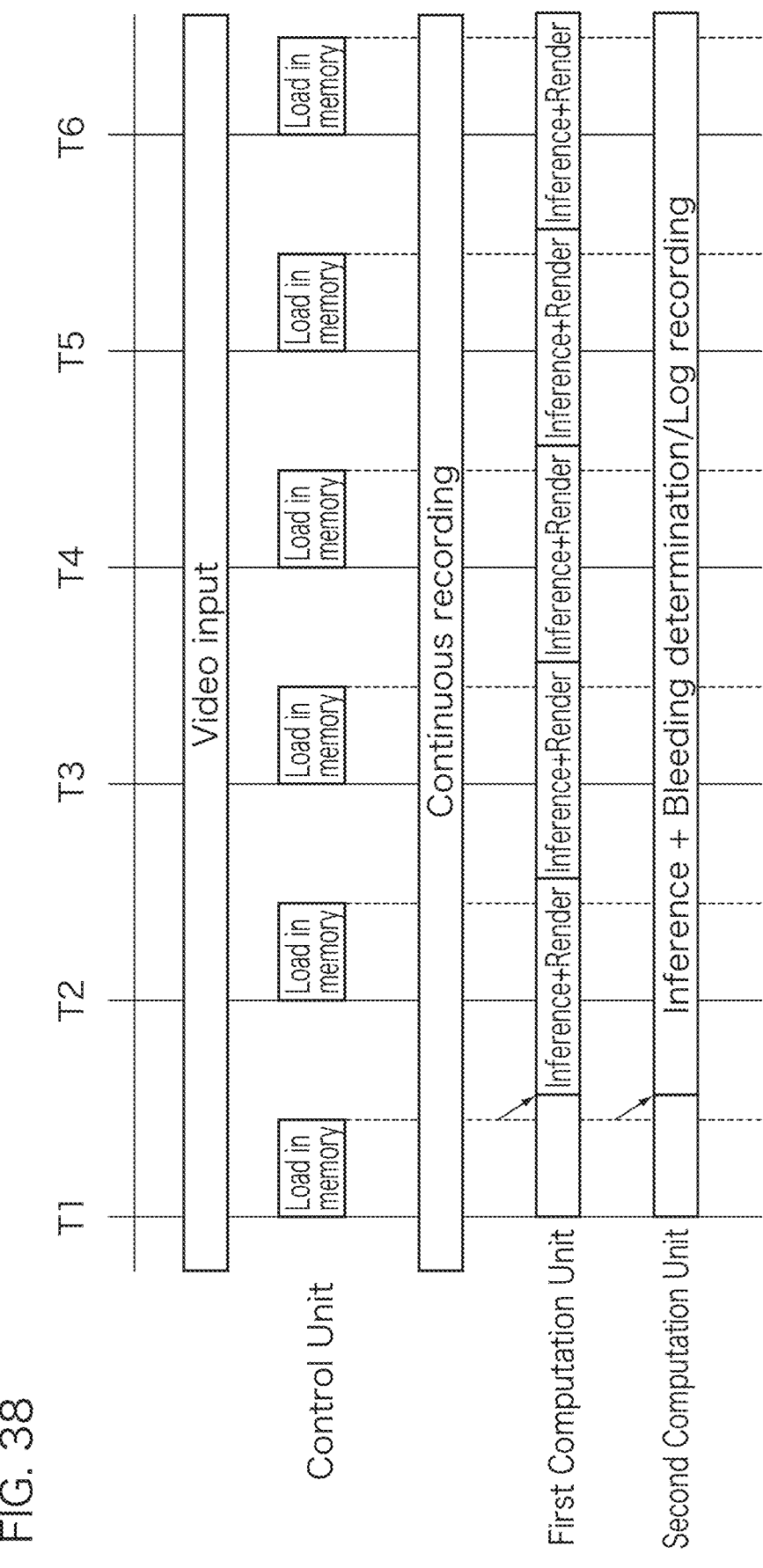
FIG. 38 is a sequence diagram illustrating an example of processing executed by an information processing device according to Embodiment 9.

FIG. 38 is a sequence diagram illustrating an example of the processing executed by the information processing device 200 according to Embodiment 9. The image data of the operative field image output from the CCU 110 is continually input (video input) to the information processing device 200 through the input unit 204. The input operative field image, for example, is continuously recorded in the storage unit 202. The control unit 201 loads the operative field image in the frame unit into the memory, and instructs the first computation unit 205 and the second computation unit 206 to execute the computation. In a case where the first computation unit 205 has computation capability of processing the operative field image of 30 FPS, the control unit 201 may instruct the first computation unit 205 to execute the computation, each time when the operative field image is loaded into the memory at a frame rate of 30 FPS. In accordance with the instruction from the control unit 201, the first computation unit 205 executes the computation (inference processing) based on the first learning model 310, and executes the processing of rendering the recognition image of the organ recognized based on the computation result on the built-in VRAM. The recognition image of the organ that is rendered on the VRAM is output through the output unit 207 and displayed on the display device 130. The information processing device 200 according to Embodiment 9 executes the organ recognition (inference) processing and the rendering processing by the first computation unit 205 in the foreground, and thus, is capable of continuously displaying the recognition image of the organ included in the operative field image.

The second computation unit 206 executes the recognition processing of an event that is not required to be continuously recognized, in the background. In Embodiment 9, as an example, a configuration will be described in which the bleeding event is recognized, but an organ damage event or a scene may be recognized, instead of the bleeding event. The computation capability of the second computation unit 206 may be lower than the computation capability of the first computation unit 205. For example, in a case where the second computation unit 206 has computation capability of processing the operative field image of 6 FPS, as illustrated in FIG. 38, the second computation unit 206 may process the operative field image input at 30 FPS with a frequency of once in five times.

Note that, in a case where the second computation unit 206 has higher computation capability, the recognition processing of a plurality of events may be executed in the background. For example, in a case where the second computation unit 206 has the same computation capability as that of the first computation unit 205, the recognition processing of up to five types of events can be executed, and the event such as the bleeding and the organ damage may be sequentially executed.

FIG. 39 is a flowchart illustrating the procedure of the processing executed by the first computation unit 205. The first computation unit 205 determines whether the current time point is an inference mode (step S901). In the case of the inference mode (S901: YES), the first computation unit 205 acquires the latest frame loaded in the memory by the control unit 201 (step S902), and executes the inference processing (step S903). In the inference processing, the first computation unit 205 executes the computation by the first learning model 310 for the organ recognition. By the computation using the first learning model 310, the recognition image of the organ is obtained. The first computation unit 205 executes the rendering processing of rendering the recognition image of the organ on the built-in VRAM (step S904). The recognition image of the organ that is rendered on the VRAM is output to the display device 130 through the output unit 207 and displayed on the display device 130. After the rendering processing is ended, the first computation unit 205 returns the processing to step S901.

In a case where the current time point is not the inference mode (S901: NO), the first computation unit 205 determines whether the current time point is a playback mode (step S905). In a case where the current time point is not the playback mode (S905: NO), the first computation unit 205 returns the processing to step S901.

In a case where the current time point is the playback mode (S905: YES), the first computation unit 205 acquires a bleeding log created by the second computation unit 206 (step S906), and acquires a designated frame from the stored partial video (step S907). Here, the partial video is a video of the operative field including a frame in a time range from a bleeding start time point to a bleeding end time point. Alternatively, the partial video may be a video of the operative field that includes the bleeding start time point and includes a frame from a time point before the start of the bleeding to a time point after a predetermined time range has elapsed. The second computation unit 206 executes the rendering processing of rendering the partial video on the built-in VRAM (step S908). The partial video that is rendered on the VRAM is output to the display device 130 through the output unit 207 and displayed on the display device 130. After the rendering processing is ended, the first computation unit 205 returns the processing to step S905.

Figure 40:
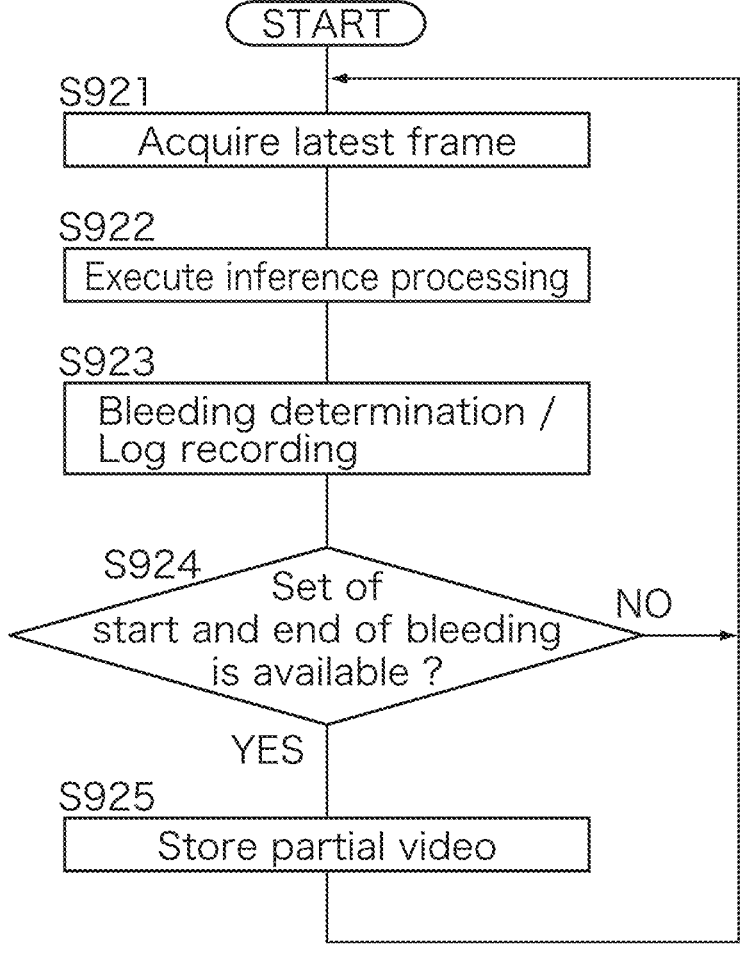
FIG. 40 is a flowchart illustrating a procedure of processing executed by a second computation unit.

FIG. 40 is a flowchart illustrating the procedure of the processing executed by the second computation unit 206. The second computation unit 206 acquires the latest frame loaded in the memory by the control unit 201 (step S921), and executes the inference processing (step S922). In the inference processing, the second computation unit 206 executes the computation by the third learning model 330 for the event recognition.

The second computation unit 206 executes bleeding determination processing and log recording processing, based on the computation result by the third learning model 330 (step S923). In a case where the number (or a ratio in the operative field image) of pixels recognized as the bleeding is a threshold value or more, the second computation unit 206 determines that the start of the bleeding is recognized, based on the computation result of the third learning model 330. In addition, after the start of the bleeding is recognized, in a case where the number (or the ratio in the operative field image) of pixels recognized as the bleeding is less than the threshold value, the second computation unit 206 determines that the end of the bleeding is recognized. In a case where the start of the bleeding or the end of the bleeding is recognized, the second computation unit 206 records the start of the bleeding or the end of the bleeding in the log.

The second computation unit 206 determines whether a set of the start of the bleeding and the end of the bleeding is available (step S924). In a case where the set is not available (S924: NO), the second computation unit 206 returns the processing to step S921. In a case where the set is available, the second computation unit 206 stores the partial video (step S925). That is, the second computation unit 206 may store the video of the operative field including the frame in the time range from the bleeding start time point to the bleeding end time point in the storage unit 202. In addition, the second computation unit 206 may store the video of the operative field that includes the bleeding start time point and includes the frame from the time point before the start of the bleeding to the time point after the predetermined time range has elapsed in the storage unit 202, as the partial video.

As described above, in Embodiment 9, the organ recognition is executed in the foreground, and the event recognition is executed in the background. In a case where the event such as the bleeding is recognized in the second computation unit 206, the first computation unit 205 is capable of executing the rendering processing of the event recorded as the log, instead of the organ recognition processing and the rendering processing.

Note that, the control unit 201 may continuously monitor a load on the first computation unit 205 and the second computation unit 206, and may execute the computation to be executed by the second computation unit 206 in the first computation unit 205, in accordance with the load of each of the computation units.

The embodiments disclosed herein are illustrative in all respects, and should not be considered restrictive. The scope of the present application is indicated by the claims, but not the meaning described above, and is intended to include meanings equivalent to the claims and all changes within the scope.

For example, the information processing devices 200 according to Embodiments 1 to 8 derive the integrative recognition result from the computation results by two types of learning models, but may derive the integrative recognition result from the computation results by three or more types of learning models. For example, by combining Embodiment 1 with Embodiment 2, the information processing device 200 may derive the integrative recognition result, based on the computation results of two types of learning models 310 and 320 for the organ recognition, and the computation result of the learning model 330 for the event recognition. In addition, by combining Embodiment 2 with Embodiment 3, the information processing device 200 may derive the integrative recognition result, based on the computation result of the learning model 310 for the organ recognition, the computation result of the learning model 330 for the event recognition, and the computation result of the learning model 340 for the device recognition. The information processing device 200 is not limited to such combinations, and may derive the integrative recognition result by suitably combining Embodiments 1 to 8.

In addition, in this embodiment, the computation by one learning model is executed in the first computation unit 205, and the computation by the other learning model is executed in the second computation unit 206, but hardware for executing the computation by the learning model is not limited to the first computation unit 205 and the second computation unit 206. For example, the computation by two or more types of learning models may be executed in the control unit 201, or the computation by two or more types of learning models may be executed on a virtual machine by preparing the virtual machine.

In addition, in this embodiment, the order of the processing is defined by the flowchart, but some of the processing may be executed in a simultaneous and parallel manner, or the order of the processing may be changed.

The respects described in each of the embodiments can be combined with each other. In addition, the independent claims and the dependent claims described in the claims can be combined with each other in all combinations, regardless of a citation format. Further, in the claims, a format is used in which a claim refers to two or more other claims (multiple dependent claim format), but the present application is not limited thereto. A format may be used in which a multiple dependent claim refers to at least one of the multiple dependent claims (Multi-Multi Claim).

It is noted that, as used herein and in the appended claims, the singular forms "a", "an", and "the" include plural referents unless the context clearly dictates otherwise.

The invention claimed is:

1. An information processing device, comprising:
one or more processors; and
a storage storing instructions causing any of the one or more processors to execute processing of:
executing computation by a first learning model trained to output information regarding organs, in accordance with input of an operative field image;
executing computation by a second learning model trained to output information regarding an event that occurs in the operative field image, a surgical tool included in the operative field image or a scene represented by the operative field image, in accordance with the input of the operative field image;

deriving an integrative recognition result for the operative field image based on a computation result based on the first learning model and the second learning model; and
outputting information based on the derived recognition result.

2. The information processing device according to claim 1,
wherein the information output from the second learning model includes information relevant to bleeding or a damage, and
wherein the instructions causing the any of the one or more processors to execute processing of:
deriving information of an organ in which bleeding or a damage occurs based on the computation result of the first learning model and the computation result of the second learning model.

3. The information processing device according to claim 1,
wherein the information output from the second learning model includes information relevant to a pulsation, and
wherein the instructions causing the any of the one or more processors to execute processing of:
deriving information of a pulsating organ based on the computation result of the first learning model and the computation result of the second learning model;
generating display information of the organ to display the organ in synchronization with the pulsation; and
outputting the generated display information of the organ.

4. The information processing device according to claim 1,
wherein the instructions causing the any of the one or more processors to execute processing of:
deriving information indicating whether a surgical tool recognized by the computation result of the second learning model is moved on an organ recognized by the computation result of the first learning model;
generating display information of the organ to change a display mode of the organ, in accordance with whether the surgical tool is moved on the organ; and
outputting the generated display information of the organ.

5. The information processing device according to claim 1,
wherein the instructions causing the any of the one or more processors to execute processing of:
determining whether a surgical tool recognized by the computation result of the second learning model is stopped;
performing recognition processing of the organ based on the computation result of the first learning model, when it is determined that the surgical tool is stopped; and
stopping the recognition processing, when it is determined that the surgical tool is not stopped.

6. The information processing device according to claim 1,
wherein the instructions causing the any of the one or more processors to execute processing of:
stopping the output of the information based on the recognition result of the organ, when determines that a surgical tool recognized by the computation result of the second learning model is not stopped.

7. The information processing device according to claim 1,
wherein the instructions causing the any of the one or more processors to execute processing of:

deriving information of the organ that is processed by the surgical tool based on the computation result of the first learning model and the computation result of the second learning model.

8. The information processing device according to claim 1, wherein the instructions causing the any of the one or more processors to execute processing of:

acquiring dimensional information of the surgical tool recognized by the computation result of the second learning model; and deriving dimensional information of the organ recognized by the computation result of the first learning model based on the acquired dimensional information.

9. The information processing device according to claim 1, wherein the instructions causing the any of the one or more processors to execute processing of:

outputting manipulation assistance information of the surgical tool recognized by the computation result of the second learning model.

10. The information processing device according to claim 1, wherein the instructions causing the any of the one or more processors to execute processing of:

determining whether a scene recognized by the computation result of the second learning model is a characteristic scene; and executing recognition processing of the organ based on the computation result of the first learning model when it is determined that the scene is the characteristic scene.

11. The information processing device according to claim 1, wherein the instructions causing the any of the one or more processors to execute processing of:

acquiring preliminary information, in accordance with the scene recognized by the computation result of the second learning model; and executing the recognition processing of the organ based on the computation result of the first learning model, with reference to the acquired preliminary information.

12. The information processing device according to claim 1, wherein the instructions causing the any of the one or more processors to execute processing of:

determining consistency between the recognition result of the organ based on the computation result of the first learning model and the preliminary information; and deriving warning information indicating that the recognition result is not consistent with the preliminary information, when it is determined that there is no consistency.

13. The information processing device according to claim 1, wherein the instructions causing the any of the one or more processors to execute processing of:

determining the consistency between the recognition result of the organ based on the computation result of the first learning model and the preliminary information; and stopping the recognition processing of the organ, when it is determined that there is no consistency.

14. The information processing device according to claim 1, wherein the instructions causing the any of the one or more processors to execute processing of:

stopping the output of the information based on the recognition result of the organ, when derives a recognition result that the recognition result of the organ based on the computation result of the first learning model is not consistent with the preliminary information.

15. The information processing device according to claim 1, wherein the first learning model includes a plurality of learning models corresponding to each of a plurality of types of organs, and wherein the instructions causing the any of the one or more processors to execute processing of:

selecting one learning model from the plurality of learning models included as the first learning model, in accordance with the scene recognized by the computation result of the second learning model; and instructing to execute computation using the selected learning model.

16. The information processing device according to claim 1, wherein the instructions causing the any of the one or more processors to execute processing of:

changing a threshold value used when recognizing the organ based on the computation result of the first learning model, in accordance with the scene recognized by the computation result of the second learning model.

17. The information processing device according to claim 16, wherein the instructions causing the any of the one or more processors to execute processing of:

setting the threshold value to a first threshold value in a scene including an organ to be detected; and setting the threshold value to a second threshold value greater than the first threshold value in a scene not including the organ to be detected.

18. The information processing device according to claim 17, wherein the instructions causing the any of the one or more processors to execute processing of:

setting the threshold value to a third threshold value less than the first threshold value until the organ to be detected is recognized; and setting the threshold value to the first threshold value when the organ to be detected is recognized.

19. The information processing device according to claim 1, wherein the instructions causing the any of the one or more processors to execute processing of:

deriving a proper name of the organ recognized by the computation result of the first learning model based on information of the scene recognized by the computation result of the second learning model.

20. The information processing device according to claim 1, wherein the instructions causing the any of the one or more processors to execute processing of:

deriving information of a structure that is not recognized by the computation result of the first learning model, with reference to the preliminary information including information of a known structure, based on the information of the organ recognized by the computation result of the first learning model, and the information of the scene recognized by the computation result of the second learning model.

21. The information processing device according to claim 1, wherein the instructions causing the any of the one or more processors to execute processing of:

deriving information of an event that may occur, with reference to the preliminary information including a case that occurred in the past, based on the information of the organ recognized by the computation result of the first learning model, and the information of the scene recognized by the computation result of the second learning model.

22. The information processing device according to claim 1, wherein the instructions causing the any of the one or more processors to execute processing of:

combining computation results of a plurality of learning models including the first learning model and the second learning model, and estimating a usage state of the surgical tool appearing in the operative field image.

23. The information processing device according to claim 1, wherein the instructions causing the any of the one or more processors to execute processing of:

acquiring computation results by the first learning model and the second learning model for operative field images including the same target, and evaluating the acquired computation results to further derive error information in the first learning model or the second learning model.

24. An information processing method for allowing a computer to execute processing of:

executing computation by a first learning model trained to output information regarding organs, in accordance with input of an operative field image;

executing computation by a second learning model trained to output information regarding an event that occurs in the operative field image, a surgical tool included in the operative field image or a scene represented by the operative field image, in accordance with the input of the operative field image;

deriving an integrative recognition result for the operative field image based on a computation result by the first learning model and a computation result by the second learning model; and outputting information based on the derived recognition result.

25. A non-transitory computer readable recording medium storing a computer program that causes a computer to execute processing comprising:

executing computation by a first learning model trained to output information regarding organs, in accordance with input of an operative field image;

executing computation by a second learning model trained to output information regarding an event that occurs in the operative field image, a surgical tool included in the operative field image or a scene represented by the operative field image, in accordance with the input of the operative field image;

deriving an integrative recognition result for the operative field image based on a computation result by the first learning model and a computation result by the second learning model; and outputting information based on the derived recognition result.

\* \* \* \* \*